(12) United States Patent
Flynn et al.

(10) Patent No.: US 8,309,545 B2
(45) Date of Patent: Nov. 13, 2012

(54) BENZOFURAN POTASSIUM CHANNEL BLOCKERS AND USES THEREOF

(75) Inventors: Bernard Luke Flynn, Vermont (AU); Jonathan B. Baell, Parkville (AU); Andrew J. Harvey, Goodwood (AU); Jason Hugh Chaplin, Doubleview (AU); Dharam Paul, Bellfield (AU); Jorgen Alvar Mould, Exeter (AU)

(73) Assignee: Bionomics Limited, Thebarton, South Australia (AU)

( * ) Notice: Subject to any disclaimer, the term of this patent is extended or adjusted under 35 U.S.C. 154(b) by 366 days.

(21) Appl. No.: 12/444,211

(22) PCT Filed: Oct. 4, 2007

(86) PCT No.: PCT/AU2007/001475
§ 371 (c)(1),
(2), (4) Date: Nov. 30, 2009

(87) PCT Pub. No.: WO2008/040057
PCT Pub. Date: Apr. 10, 2008

(65) Prior Publication Data
US 2010/0087430 A1  Apr. 8, 2010

Related U.S. Application Data

(60) Provisional application No. 60/849,488, filed on Oct. 4, 2006.

(51) Int. Cl.
*A61K 31/5377* (2006.01)
*A61K 31/343* (2006.01)
*C07D 413/12* (2006.01)
*C07D 307/78* (2006.01)

(52) U.S. Cl. .............. 514/233.5; 514/469; 544/153; 549/471

(58) Field of Classification Search ............. 514/233.5, 514/469; 549/469; 544/153
See application file for complete search history.

(56) References Cited

U.S. PATENT DOCUMENTS

| 4,845,096 A | 7/1989 | Schlecker et al. |
| 5,494,895 A | 2/1996 | Garcia et al. |
| 6,051,590 A | 4/2000 | Bao et al. |
| 6,077,680 A | 6/2000 | Kem et al. |
| 2006/0079535 A1 | 4/2006 | Wulff et al. |

FOREIGN PATENT DOCUMENTS

| DE | 37 10 469 A1 | 10/1998 |
| EP | 0 074 138 A1 | 3/1983 |
| EP | 0 094 769 B1 | 11/1986 |
| EP | 0 303 920 B1 | 3/1992 |
| WO | 97/16437 | 5/1997 |
| WO | 97/16438 | 5/1997 |
| WO | WO 2006096911 A1 * | 9/2006 |

OTHER PUBLICATIONS

Cahalan, M.D. et al., "Ion Channels in the Immune System as Targets for Immunosuppression" *Current Opinion in Biotechnology* (1997) pp. 749-756, vol. 8.
Cahalan, M.D. et al., "A Voltage-Gated Potassium Channel in Human T Lymphocytes" *Journal of Physiology* (1985) pp. 197-237, vol. 358.
Grissmer, S. et al., "Expression and Chromosomal Localization of a Lymphocyte $K^+$ Channel Gene" *Proc. National Academy of Science* (1990) pp. 9411-9415, vol. 87.
Verheugen, J. et al., "Voltage-Gated and $Ca^{2+}$-activated $K^+$ Channels in Intact Human T Lymphocytes" *Journal of Gen. Physiology* (1995) pp. 765-794, vol. 105.
Aiyar, J. et al., "The Signature Sequence of Voltage-Gated Potassium Channels Projects into the External Vestibule" *The Journal of Biological Chemistry* (1996) pp. 31013-31016, vol. 271(49).
Grissmer, S. et al., "Calcium-Activated Potassium Channels in resting and Activated Human T Lymphocytes" *Journal of Gen. Physiology* (1993) pp. 601-630, vol. 102.
Fanger, C.M. et al., "Ca;modulin Mediates Calcium-dependent Activation of the Intermediate Conudctance $K_{Ca}$ Channel, *IKCa1*" *The Journal of Biological Chemistry* (1999) pp. 5746-5754, vol. 274(9).
Rauer, H. et al., "Structural Conservation of the Pores of Calcium-Activated and Voltage-Gated Potassium Channels Determined by a Sea Anemone Toxin" *The Journal of Biological Chemistry* (1999) pp. 21885-21892, vol. 274(31).
Vandorpe, D.H. et al., "cDNA Cloning and Functional Characterization of the Mouse $Ca^{2+}$-gated $K^+$ Channel, mIK1" *The Journal of Biological Chemistry* (1998) pp. 21542-21553, vol. 273(34).
Joiner, W.J. et al., "hSK4, a Member of a Novel Subfamily of Calcium-Activated Potassium Channels" *Proc. National Academy of Science* (1997) pp. 11013-11018, vol. 94.
Khanna, R. et al., "hSK4/hIk1, a Calmodulin-binding $K_{ca}$ Channel in Human T Lymphocytes" *The Journal of Biological Chemistry* (1999) pp. 14838-14849, vol. 274(21).
Logsdon, N. J. et al., "A Novel Gene, *hKCa4*, Encodes the Calcium-Activated Potassium Channel in Human T Lymphocytes" *The Journal of Biological Chemistry* (1997) pp. 32723-32726, vol. 272(52).
Ghanshani, S. et al., "Human Calcium-Activated Potassium Channel Gene *KCNN4* Maps to Chromosomes 19q13.2 in the Region Deleted in Diamond-Blackfan Anemia" *Genomics* (1998) pp. 160-161, vol. 51.
Wulff, H. et al., "The Voltage-Gated Kv1.3K+ Channel in Effector Memory T Cells as New Target for MS" *The Journal of Clinical Investigation* (2003) pp. 1703-1713, vol. 11.
Beeton, C. et al., "Selective Blockade of T Lymphocyte $K^+$ Channels Ameliorates Experimental Autoimmune Encephalomyelitis, a Model for Multiple Sclerosis" *PNAS* (2001) pp. 13942-13947, vol. 98(24).
Vennekamp, J. et al., "Kv1.3-Blocking 5-Phenylalkoxypsoralens: A new Class of Immunomodulators" *Molecular Pharmacology* (2004) pp. 1364-1374, vol. 65(6).

(Continued)

*Primary Examiner* — Kristin Bianchi
(74) *Attorney, Agent, or Firm* — Scully, Scott, Murphy & Presser, P.C.

(57) ABSTRACT

The present invention relates to compounds useful in the modulation of potassium channel activity in cells, in particular the activity of $K_v1.3$ channels found in T cells. The invention also relates to the use of these compounds in the treatment or prevention of autoimmune and inflammatory diseases, including multiple sclerosis, pharmaceutical compositions containing these compounds and methods for their preparation.

9 Claims, No Drawings

OTHER PUBLICATIONS

Xu, J. et al., "The Voltage-Gated Potassium Channel Kv1.3 Regulates Peripheral Insulin Sensitivity" *PNAS* (2004) pp. 3112-3117, vol. 101(9).

Wulff, H. et al., "Potassium Channels as Therapeutic Targets for Autoimmune Disorders" *Current Opinion in Drug Discovery & Development* (2003) pp. 640-647, vol. 6(5).

Beeton, C. et al., "Targeting Effector Memory T Cells with a Selective Peptide Inhibitor of Kv1.3 Channels for Therapy of Autoimmune Diseases" *Molecular Pharmacology* (2005) pp. 1369-1381, vol. 67.

Schmalhofer, W.A. et al., "Identification of a New Class of Inhibitors of the Voltage-Gated Potassium Channel, $K_v1.3$, with Immunosuppressant Properties" *Biochemistry* (2002) pp. 7781-7794, vol. 41.

Schmalhofer, W.A. et al., "Di-Substituted Cyclohexyl Derivatives Bind to Two Identical Sites with Positive Cooperatively on the Voltage-Gated Potassium Channel, $K_v1.3$" *Biochemistry* (2003) pp. 4733-4743, vol. 42.

Poster Abstract No. 1078 (1999) Meeting of the American Physiological Society in Snowmass, Colorado, *The Physiologist* vol. 42, A12.

Musante, C., "Trasformazione di Composti del Furan-Cro-mone in Derivati del Benzo-Difurano" *Annali de Chimica* (1959) pp. 768-781, vol. 46.

Bourgery, G. et al., "Synthesis and Antiarrhythmic Activity of New Bensofuran Derivatives" *Journal of Medical Chemistry* (1981) pp. 159-167, vol. 24.

Musante, C. et al., "Glucosidi Sintetici Del Furo-Cromone" *Farmaco Eduzione Scientifics* (1961) pp. 343-350, vol. 16.

Abdel Hafez, O.M. et al., "Synthesis of Some Potentially Bioactive Compounds from Visnaginone" *Molecules* (2001) pp. 396-405, vol. 6(4).

Abdel-Hafez, O.M. et al., "Synthesis of Some Benzo[b]Furan Derivatives with Expected Biological Activity" *Bulletin of the Faculty of Pharmacy* (1996) pp. 111-117, vol. 34(2).

Ragab, F.A. et al., "Synthesis, Inotropic, Anti-Arrhythmic and Hypotensive Activities of Some New Benzofuran Derivatives" *European Journal of Medical Chemistry* (1987) pp. 265-267, vol. 22.

Ranu, B. C. et al., "Selective Reductive Cleavage of 2,3-epoxybromides by the $InCl_3$-$NaBH_4$ Reagent System" *Tetrahedron Letters* (2004) pp. 8579-8581, vol. 45.

S Chmitz, A. et al., "Design of PAP-1, a Selective Small Molecule Kv1.3 Blocker, for the Suppression of Effector Memory T Cells in Autoimmune Diseases" *Molecular Pharmacology* (2005) pp. 1254-1270, vol. 68.

* cited by examiner

BENZOFURAN POTASSIUM CHANNEL BLOCKERS AND USES THEREOF

CROSS-REFERENCE TO RELATED APPLICATIONS

This application claims the benefit of U.S. Provisional Application No. 60/849,488 filed on Oct. 4, 2006.

FIELD OF THE INVENTION

The present invention relates to compounds useful in the modulation of potassium channel activity in cells, in particular the activity of Kv1.3 channels found in T cells. The invention also relates to the use of these compounds in the treatment or prevention of autoimmune and inflammatory diseases, including multiple sclerosis, pharmaceutical compositions containing these compounds and methods for their preparation.

BACKGROUND

Many autoimmune and chronic inflammatory diseases are related to immunoregulatory abnormalities. Diseases such as systemic lupus erythematosis, chronic rheumatoid arthritis, multiple sclerosis and psoriasis have in common the appearance of autoantibodies and self-reactive lymphocytes.

Multiple sclerosis is the most common neurological disease of young people. It is believed to cost more in medical care and lost income than any other neurological disease of young adults.

Multiple sclerosis affects the myelin sheaths of nerves. Myelin is an insulating material that coats most axons and allows rapid signal conduction over long distances by saltatory conduction. It is thought that antibodies and specialised cells of the immune system attack the myelin coating. This process leads to inflammation and scarring (sclerosis) which damages blood vessels in the area by the formation of a lesion known as a plaque. These plaques are characterised by being infiltrated by macrophages and T cells. This results in demyelination with the consequential loss of the rapid signal conduction.

A possible method of treating these autoimmune and inflammatory diseases is by suppressing T-cell proliferation and modulating their activation.

The early stages of T-cell activation may be conceptually separated into pre-$Ca^{2+}$ and post-$Ca^{2+}$ events (Cahalan and Chandy 1997, *Curr. Opin. Biotechnol.* 8 749). Following engagement of the T-cell receptor by an antigen, activation of tyrosine kinases and the generation of inositol 1,4,5-triphosphate lead to the influx of $Ca^{2+}$ and a rise in the cytoplasmic $Ca^{2+}$ concentration. The rise in $Ca^{2+}$ activates the phosphatase calcineurin, which then dephosphorylates a cytoplasmically localized transcription factor (N-FAT) enabling it to accumulate in the nucleus and bind to a promoter element of the interleukin-2 gene. Along with parallel events involving the activation of protein kinase C and ras, gene transcription leads to lymphokine secretion and to lymphocyte proliferation. Some genes require long-lasting $Ca^{2+}$ signals while others require only a transient rise of $Ca^{2+}$.

Ion channels underlie the $Ca^{2+}$ signal of T-lymphocytes. $Ca^{2+}$ ions move across the plasma membrane through a channel termed the store-operated $Ca^{2+}$ channel or the calcium release-activated $Ca^{2+}$ channel. Two distinct types of potassium channels indirectly determine the driving force of calcium entry. The first is the voltage-gated Kv1.3 channel (Cahalan 1985, *J. Physiol.* 385: 197; Grissmer 1990, *Proc. Natl. Acad. Sci. USA* 87 9411; Verheugen 1995, *J. Gen. Physiol.* 105 765; Aiyar 1996, *J. Biol. Chem.* 271 31013; Cahalan and Chandy 1997, *Curr. Opin. Biotechnol.* 8 749) and the second is the intermediate-conductance calcium-activated potassium channel, IKCa1 (Grissmer 1993, *J. Gen. Physiol.* 102 601; Fanger 1999 *J. Biol. Chem.* 274 5746; Rauer 1999, *J. Biol. Chem.* 274 21885; VanDorpe 1998, *J. Biol. Chem.* 273 21542; Joiner 1997, *Proc. Natl. Acad. Sci. USA* 94 11013; Khanna 1999, *J. Biol. Chem.* 274 14838; Lodgson 1997, *J. Biol. Chem.* 272 32723; Ghanshani 1998, *Genomics* 51 160). When these potassium channels open, the resulting efflux of $K^+$ hyperpolarizes the membrane, which in turn accentuates the entry of $Ca^{2+}$, which is absolutely required for downstream activation events (Cahalan and Chandy 1997, *Curr. Opin. Biotechnol.* 8: 749).

The predominant voltage-gated channel in human T-lymphocytes is encoded by Kv1.3, a Shaker-related gene. Kv1.3 has been characterised extensively at the molecular and physiological level and plays a vital role in controlling T-lymphocyte proliferation, mainly by maintaining the resting membrane potential of resting T-lymphocytes. Inhibition of this channel depolarizes the cell membrane sufficiently to decrease the influx of $Ca^{2+}$ and thereby prevents downstream activation events. Advantageously the Kv1.3 channel is almost exclusively located in T-lymphocytes.

Accordingly, compounds which are selective Kv1.3 blockers are potential therapeutic agents as immunosuppressants for the prevention of graft rejection, and the treatment of autoimmune and inflammatory disorders. They could be used alone or in conjunction with other immunosuppressants, such as selective IKCa1 blockers or cyclosporin, in order to achieve synergism and/or to reduce toxicity, especially of cyclosporin.

Developments in the field of voltage-gated K-channel electrophysiology have strengthened the case for treating of multiple sclerosis and also diabetes mellitus by inhibiting the Kv1.3 channel. It was found that autoreactive T-cells from multiple sclerosis patients exhibit highly elevated levels of Kv1.3 (Wulff, H et al (2003) *J. Clin Invest.* 111 (11) 1703-1713). ShK-K22Dap, a selective peptide blocker of Kv1.3, potently inhibited the proliferation of T-cells with this high-Kv1.3 phenotype. (Beeton, C. et al (2001) *PNAS* 98 13942-13947). The connection between T-cell replication and Kv1.3 blockade has also been shown through the use of a small molecule, a psoralen derivative, that is an active and relatively specific inhibitor of the Kv1.3 channel. The derivative showed specificity in inhibiting the proliferation of the high Kv1.3 T-cells over peripheral blood T-cells (Vennekamp et al (2004) Mol. Pharm. 65 1364-1374).

The Kv1.3 channel has also been associated with diabetes. Studies of Kv1.3 knockout mice found that the mice have increased insulin sensitivity. The selective blockage of the Kv1.3 channel also led to increased insulin sensitivity (Xu, J. et al. (2004) *PNAS* 101 (9), 3122-3117). It has been suggested by Wulff, who was involved in the electrophysiology on multiple sclerosis that diabetes also involves autoreactive T-cells that express very high levels of Kv1.3 (Wulff, H. et al. (2003) *Curr. Op.DDD.* 6 640-647).

At present there exist a number of non-selective potassium channel blockers that will inhibit lymphocyte proliferation, but have adverse side effects. Other potassium channels exist in a wide range of tissues including the heart and brain, and generally blocking these channels is undesirable. Accordingly it would be advantageous to provide or identify compounds, which are selective inhibitors of the Kv1.3 channel.

U.S. Pat. No. 5,494,895 discloses the use of a thirty-nine amino acid peptide, scorpion peptide margatoxin, as a selective inhibitor and probe of Kv1.3 channels present in human lymphocytes, and also as an immunosuppressant. However the use of this compound is limited by its potent toxicity.

International Patent Application publication No's WO 97/16438 and WO 09/716,437, and U.S. Pat. No. 6,051,590 describe the use of the triterpene, correolide and related compounds as immunosuppressants. The potential for these compounds to become immunosuppressants was illustrated by experiments showing their attenuation of the delayed-type hypersensitivity (DTH) response in mini-swine.

U.S. Pat. No. 6,077,680 describes DNA segments and proteins derived from sea anemone species, more particularly ShK toxin from *Stichodactyla helianthus*. The ShK toxin was found to block Kv1.1, Kv1.3, Kv1.4 and Kv1.6, but a mutant ShK-K22DAP was found to selectively block Kv1.3. Unfortunately the mutant did not exhibit the requisite pharmacokinetic profile for clinical use. A recently reported ShK analog, ShK(L5), was at least 100-fold more active against Kv1.3 ($K_d$=69 pM) than Kv1.1 and furthermore it showed at least 250-fold selectivity over every other relevant member of the Kv1 family (Beeton at al. (2005) *Mol. Pharm. In press*).

Both ShK toxin and ShK(L5) were shown to both prevent and treat experimental autoimmune encephalomyelitis in Lewis rats, an animal model for human multiple sclerosis (Beeton, et al. (2001) *Proc. Natl. Acad. Sci. USA* 98 13942), by selectively targeting T-cells chronically activated by the myelin antigen, MBP (myelin basic protein). The same study also indicated that chronically activated encephalitogenic rat T-cells express a unique channel phenotype characterised by high expression of Kv1.3 channels (approximately 1500 per cell) and low numbers of IKCa1 channels (approximately 120 per cell). This channel phenotype is distinct from that seen in quiescent and acutely activated cells and may be a functionally relevant marker for chronically activated rat T lymphocytes.

Other compounds which are blockers of Kv1.3 include psoralens (Vennekamp et al. (2004) *Mol. Pharm.* 65, 1365-1374 and Wulff et al., US 2006/0079535) and selected benzamides (Schalhofer et al. (2002) *Biochem.* 41, 7781-7794 and Schalhofer et al (2003) *Biochem.* 42, 4733-4743.

Khellinone, a substituted benzofuran and natural product from certain plants, and 8-Methoxypsoralen (8-MOP), both commercially available products, have been found to exhibit blocking activity on the Kv1.3 channel.

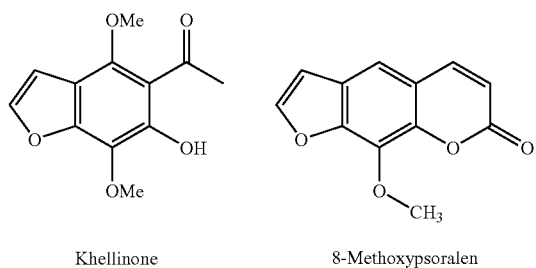

Khellinone      8-Methoxypsoralen

Khellinone, 8-MOP and four dimeric variants thereof were described in a Poster (abstract. No. 1078) at a meeting of the American Physiological Society in Snowmass, Colo. (*The Physiologist* 42: A12 (1999)). The authors were testing whether linking two active units with a spacer, improved activity. Some of the bivalent derivatives were said to be ineffective, and others were said to block the Kv1.3 channel, but lack therapeutic utility due to their extreme sensitivity to hydrolysis (very poor stability) and high lipophilicity (poor solubility in clinical conditions).

European Patent Application 82201051 describes furanochromone derivatives for use as anti-inflammatory agents amongst other suggested uses. An intermediate compound used in the manufacture of the chromone derivatives was 5-(benzoylacetyl)-4,7-dimethoxy-6-hydroxy-benzofuran.

European Patent Application 83302551 describes a process for preparing di-4,7-loweralkoxybenzofurans for use as intermediates in the preparation of khellin and related compounds.

German patent DE 3710469 and European patent publication number EP303920 describe the synthesis of 5-acetyl-4-benzyloxy-7-methoxy-6-hydroxy-benzofuran by alkaline ring cleavage of a pyrone ring of a fused system. This is also described in an article by Musante in Annali de Chimica (1959) 46, 768-781 together with the compound where the benzyloxy group is replaced with the residue of 2-hydroxyacetophenone.

An article by Bougery, G et al in J. Med. Chem. (1981) 24, 159-167 described 4-alkoxy (ethoxy and iso-propoxy) khellinone derivatives for use as intermediates in the manufacture of other compounds.

An article by Musante, C and Fatutta, S in Farmaco Eduzione Scientifics (1961) 16, 343-350 described a 7-glucosylkhellinone compound for use as a coronary dilator.

Articles by Abdel Hafez, O et al in Molecules (online computer file) (2001), 6(4), 396-405, by El-Hafez, O, in Bulletin of the Faculty of Pharmacy (Cairo University) (1996), 34(2), 111-117 and by Ragab, F. A. and Tawfeek, H in Eur. J. Med. Chem. (1987) 22(3), 265-267 describe assorted khellinone derivatives with assorted alkylamines at the 7 position.

SUMMARY OF THE INVENTION

The invention provides compounds of formula (I) or salts thereof,

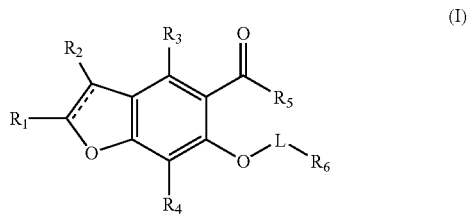

(I)

wherein
----- is an optional double bond;
$R_1$ and $R_2$ are independently selected from hydrogen, halo, optionally substituted lower alkyl, optionally substituted aryl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl);
$R_3$ and $R_4$ are independently selected from hydrogen, cyano, halo, nitro, optionally substituted alkyl, optionally substituted alkenyl, optionally substituted aryl, optionally substituted alkynyl, optionally substituted $C_{3-7}$ cycloalkyl, optionally substituted $C_{4-7}$ cycloalkenyl, —OR, —C(O)R, —C(O)

OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl);

$R_5$ is selected from optionally substituted alkyl, —OR, —C(O)R, —C(O)OR, —OC(O)R, SR, (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl);

L is a divalent linker group of 1-6 atoms in length selected from optionally substituted alkylene, optionally substituted alkenylene, optionally substituted alkynylene; and $R_6$ is selected from halo, CN, optionally substituted $C_{3-7}$ cycloalkyl, optionally substituted aryl, optionally substituted heteroaryl, optionally substituted heterocyclyl, —C(O)-heterocyclyl, —C(O)NR'''R''', —NR'''R''', —OR''', SR''', —S(O)R''', —S(O)$_2$R''', —Se(O)R''', and Se(O)$_2$R''' (where each R''' is independently selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl).

In an aspect of the invention there is provided a method for the treatment or prevention of autoimmune or chronic inflammatory diseases, or the prevention of rejection of foreign organ transplants and/or related afflictions, by the administration of a compound of formula I or a pharmaceutically acceptable salt thereof, or a composition containing a compound of formula I or pharmaceutically acceptable salt thereof.

In another aspect the invention provides the use of a compound of formula I or a salt thereof in the manufacture of a medicament for the treatment or prevention of autoimmune or chronic inflammatory diseases, or the prevention of rejection of foreign organ transplants and/or related afflictions.

In another aspect of the invention there is provided a method of intentionally modulating potassium ion channel activity of T-cells by the application of a compound of Formula I, or a pharmaceutically acceptable salt thereof, to said T-cells.

In a further aspect of the invention there is provided a pharmaceutical composition for use as an immunosuppressant, the composition comprising an effective amount of a compound of Formula I or pharmaceutically acceptable salt thereof and optionally a carrier or diluent.

In another aspect of the invention there is provided a process for the preparation of compounds of formula I or salts thereof.

DETAILED DESCRIPTION OF THE INVENTION

The invention is based on the discovery that compounds of the general formula I, as described in the above Summary of the Invention can have useful properties as inhibitors of potassium cell channels, and particularly the Kv1.3 channel. Such compounds have significant potential as immunosuppressants for the treatment of autoimmune disorders such as multiple sclerosis and rheumatoid arthritis. They may also be useful in the treatment or prevention of graft rejection.

The term "alkyl" as used alone or in combination herein refers to a straight or branched chain saturated hydrocarbon group. The term "$C_{1-12}$ alkyl" refers to such a group containing from one to twelve carbon atoms and the terms "$C_{1-6}$ alkyl" and "lower alkyl" refer to such groups containing from one to six carbon atoms, such as methyl ("Me"), ethyl ("Et"), n-propyl, isopropyl, n-butyl, isobutyl, sec-butyl, tert-butyl and the like.

The term "alkylene" refers to divalent alkyl groups preferably having from 1 to 10 carbon atoms and more preferably 1 to 6 carbon atoms. Examples of such alkylene groups include methylene (—CH$_2$—), ethylene (—CH$_2$CH$_2$—), and the propylene isomers (e.g., —CH$_2$CH$_2$CH$_2$— and CH(CH$_3$)CH$_2$—), and the like.

The term "$C_{3-7}$ cycloalkyl" refers to non-aromatic, saturated non-aromatic carbocycles having from 3 to 7 carbon atoms. Examples include cyclopentyl and cyclohexyl.

The term "alkenyl" refers to a straight or branched hydrocarbon containing one or more double bonds, preferably one or two double bonds. The term "$C_{2-12}$ alkenyl" refers to such a group containing from two to twelve carbon atoms. Examples of alkenyl include allyl, 1-methylvinyl, butenyl, iso-butenyl, 1,3-butadienyl, 3-methyl-2-butenyl, 1,3-butadienyl, 1,4-pentadienyl, 1-pentenyl, 1-hexenyl, 3-hexenyl, 1,3-hexadienyl, 1,4-hexadienyl and 1,3,5-hexatrienyl.

The term "alkenylene" refers to divalent alkenyl groups preferably having from 2 to 8 carbon atoms and more preferably 2 to 6 carbon atoms. Examples include ethenylene (—CH=CH—), and the propenylene isomers (e.g., —CH$_2$CH=CH— and —C(CH$_3$)=CH—), and the like.

The term "$C_{4-7}$ cycloalkenyl" refers to non aromatic carbocycles having 4 to 7 carbon atoms and having one or more double bonds. Examples include cyclopentenyl, 1-methylcyclopentenyl, cyclohexenyl, 1,3-cyclopentadienyl, 1,3-cyclohexadienyl and 1,4-cyclohexadienyl.

The term "alkynyl" refers to a straight or branched hydrocarbon containing one or more triple bonds, preferably one or two triple bonds. The term "$C_{2-12}$ alkynyl" refers to such a group containing from two to twelve carbon atoms. Examples include 2-propynyl and 2- or 3-butynyl.

The term "alkynylene" refers to the divalent alkynyl groups preferably having from 2 to 8 carbon atoms and more preferably 2 to 6 carbon atoms. Examples include ethynylene (—C≡C—), propynylene (—CH$_2$—C≡C—), and the like.

The term "alkoxy" as used alone or in combination refers to a straight or branched chain alkyl group covalently bound via an oxygen linkage (—O—) and the terms "$C_{1-6}$ alkoxy" and "lower alkoxy" refer to such groups containing from one to six carbon atoms, such as methoxy, ethoxy, propoxy, isopropoxy, butoxy, t-butoxy and the like.

The terms "alkenyloxy" and "alkynyloxy" as used alone or in combination respectively refer to an alkenyl and alkynyl group as earlier described linked via an oxygen linkage (—O—).

The term "aromatic" when used alone or in combination refers to monocyclic or bicyclic aryl rings and ring systems (aromatic hydrocarbon rings or ring systems) and also aromatic heterocyclic rings or ring systems, as known as heteroaryl or heteroaromatic rings. Preferred aromatic rings are optionally substituted phenyl ("Ph") rings.

The term "aryl" refers to carbocyclic (non-heterocyclic) aromatic rings or ring systems. The aromatic rings may be mono- or bi-cyclic ring systems. The aromatic rings or ring systems are generally composed of 5 to 10 carbon atoms. Examples of suitable aryl groups include but are not limited to phenyl, biphenyl, naphthyl, tetrahydronaphthyl, and the like.

Preferred aryl groups include phenyl, naphthyl, indenyl, azulenyl, fluorenyl or anthracenyl.

The term "heteroaryl" refers to a monovalent aromatic carbocyclic group, preferably of from 2 to 10 carbon atoms and 1 to 4 heteroatoms selected from oxygen, nitrogen and sulfur within the ring. Preferably the heteroatom is nitrogen. Such heteroaryl groups can have a single ring (e.g., pyridyl, pyrrolyl or furyl) or multiple condensed rings (e.g., indolizinyl or benzothienyl).

The term "heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring.

Examples of 5-membered monocyclic heterocyclyl and heteroaryl groups include furyl, thienyl, pyrrolyl, H-pyrrolyl, pyrrolinyl, pyrrolidinyl, oxazolyl, oxadiazolyl, (including 1,2,3 and 1,2,4 oxadiazolyls) thiazolyl, isoxazolyl, furazanyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls).

Examples of 6-membered monocyclic heterocyclyl and heteroaryl groups include pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl and triazinyl.

The above heterocycles may be optionally substituted with a broad range of substituents, such as $C_{1-6}$ alkyl, $C_{1-6}$ alkoxy, $C_{2-6}$ alkenyl, $C_{2-6}$ alkynyl, halo, hydroxy, mercapto, trifluoromethyl, phenyl, phenyloxy, phenylalkyl, phenylalkyloxy, amino, cyano or mono or di($C_{1-6}$alkyl)amino.

As referred to above heterocycle or heteroaryl may be fused to a carbocyclic ring such as phenyl, naphthyl, indenyl, azulenyl, fluorenyl, and anthracenyl.

Examples of 8, 9 and 10-membered bicyclic heterocyclyl and heteroaryl groups include 1H thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl, pteridinyl and the like. These heterocycles may be optionally substituted, for example with $C_{1-6}$alkyl, $C_{1-6}$alkoxy, $C_{2-6}$alkenyl, $C_{2-6}$alkynyl, halo, hydroxy, mercapto, trifluoromethyl, cyano, phenyl, phenyloxy, phenylalkyl, phenylalkyloxy, amino and mono or di($C_{1-6}$alkyl) amino.

Examples of some preferred heterocyclic and heteroaromatic radicals include (optionally substituted) isoxazoles, isothiazoles, 1,3,4-oxadiazoles, 1,3,4-thiadiazoles, 1,2,4-oxadiazoles, 1,2,4-thiadiazoles, oxazoles, thiazoles, pyridines, pyridazines, pyrimidines, pyrazines, 1,2,4-triazines, 1,3,5-triazines, benzoxazoles, benzothiazoles, benzisoxazoles, benzisothiazoles, quinolines, quinoxalines, furyl, thienyl, pyridyl, pyrrolyl, oxazolyl, thiazolyl, imidazolyl, pyrazolyl, isoxazolyl, isothiazolyl, 1,2,3-oxadiazolyl, 1,2,4-oxadiazolyl, 1,2,4-oxadiazol-5-one, 1,2,3-triazolyl, 1,3,4-thiadiazolyl, pyridazinyl, pyrimidinyl, pyrazinyl, 1,3,5-triazinyl, 1H thieno[2,3-c]pyrazolyl, thieno[2,3-b]furyl, indolizinyl, indolyl, isoindolyl, 3H-indolyl, indolinyl, benzo[b]furanyl, benzo[b]thiophenyl, 1H-indazolyl, benzimidazolyl, tetrazolyl, uridinyl, and cytosinyl. These radicals can be optionally substituted with, by example, $C_{1-6}$alkyl, $C_{1-6}$alkoxy, $C_{2-6}$alkenyl, $C_{2-6}$alkynyl, halo, hydroxy, mercapto, trifluoromethyl, amino, phenyl, phenyloxy, phenylalkyl, phenylalkyloxy, cyano or mono or di($C_{1-6}$alkyl)amino.

Heteroaryl or heteroaromatic rings may preferably be selected from isoxazolyl, oxazolyl, imidazolyl, thiazolyl, thiadiazolyl, isothiazolyl, furazanyl, triazolyl, pyridyl, pyrimidinyl, furyl, pyrazolyl, pyridazinyl, thienyl and aryl fused heteroaromatic rings such as benzfuranyl, benzothiophenyl and benzoisoxazolyl.

Heterocyclyl or heterocyclic rings may preferably be selected from pyrrolidine, imidazoline, 2-imidazolidone, 2-pyrrolidone, pyrrolin-2-one, tetrahydrofuran, 1,3-dioxolane, piperidine, tetrahydropyran, oxazoline, 1,3-dioxane, 1,4-piperazine, morpholine and thiomorpholine.

The term "arylalkyl" refers to carbocyclic aromatic rings or ring systems as previously described and substituted by an alkyl group, also as previously described. Unless otherwise indicated the aryl substituent is attached by the alkyl part of the substituent. Likewise the terms "aryl $C_{1-12}$ alkyl", "aryl $C_{2-12}$ alkenyl" and "aryl $C_{2-12}$ alkynyl" refer to carbocyclic aromatic rings or ring systems as previously described and substituted by a $C_{1-12}$ alkyl, $C_{2-12}$ alkenyl or $C_{2-12}$ alkynyl group, as previously described.

The terms "halo" and "halogen" refers to fluoro, chloro, bromo and iodo groups.

The term "halo alkyl" group has one or more of the hydrogen atoms on an alkyl group replaced with halogens. A notable example is —$CF_3$.

The term "aryloxy" refers to an aryl group as earlier described linked to the parent structure via an oxygen linkage (—O—). A notable example is phenoxy. Similarly the term "heteroaryloxy" refers to a heteroaryl group as earlier described linked to the parent structure via an oxygen group. A notable example is a 4, 6 or 7-benzo[b]furanyloxy group.

"Divalent linker group" is taken to mean a divalent group capable of forming a stable bridge between the core structure of formula (I) or formula (Ia) and the radical $R_6$. Examples of divalent linker groups include alkylene, alkenylene, alkynylene, arylene, heteroarylene, heterocyclylene, alkylenearylene, alkylenearylenealkylene, alkyleneheteroarylenealkylene, alkyleneheterocyclylenealkylene, and the like.

The term "optionally substituted" means that a group may include one or more substituents. One or more hydrogen atoms on the group may be replaced by substituent groups independently selected from halogens, $C_{1-6}$ alkyl, $C_{2-6}$ alkenyl, $C_{2-6}$ alkynyl, —$(CH_2)_p C_{3-7}$ cycloalkyl, —$(CH_2)_p C_{4-7}$ cycloalkenyl, —$(CH_2)_p$ aryl, —$(CH_2)_p$ heterocyclyl, —$(CH_2)_p$ heteroaryl, —$C_6H_4S(O)_q C_{1-6}$ alkyl, $C(Ph)_3$, —CN, —OR, —O—$(CH_2)_{1-6}$—R, —O—$(CH_2)_{1-6}$—OR, —OC(O), —C(O), —C(O)OR, —OC(O)NR'R", NR'R", —NRC(O)R', —NRC(O)NR'R", —NRC(S)NR'R", —NRS(O)$_2$R', —NRC(O)OR', —C(NR)NR'R", —C(=NOR'), —C(=NOH)NR'R", —C(O)NR'R", —C(=NCN)—NR'R", —C(=NR)NR'R", —C(=NR')SR", —NR'C(=NCN)SR", —CONRSO$_2$R', —C(S)NR'R", —S(O)$_q$R, —SO$_2$NR'R", —SO$_2$NRC(O)R', —OS(O)$_2$R, —PO(OR)$_2$ and —NO$_2$; where p is 0-6, q is 0-2 and each R, R' and R" is independently selected from H, $C_{1-6}$ alkyl, $C_{2-6}$ alkenyl, $C_{2-6}$ alkynyl, $C_{3-7}$ cycloalkyl, $C_{4-7}$ cycloalkenyl, aryl, heterocyclyl, heteroaryl, $C_{1-6}$ alkylaryl, $C_{1-6}$ alkylheteroaryl, and $C_{1-6}$ alkylheterocyclyl, wherein the alkyl, alkenyl, alkynyl, cycloalkyl, cycloalkenyl, aryl, heterocyclyl, heteroaryl, $C_{1-6}$ alkylaryl, $C_{1-6}$ alkylheteroaryl, or $C_{1-6}$ alkylheterocyclyl, may be optionally substituted with one to six of same or different groups selected from halogen, hydroxy, lower alkyl, lower alkoxy, —$CO_2H$, $CF_3$, CN, phenyl, $NH_2$ and $NO_2$; or when R' and R" are attached to the same nitrogen atom, they may, together with the atom to which they are attached, form a 5 to 7 membered nitrogen containing heterocyclic ring.

In the case of the divalent linker group, the term "optionally substituted" also indicates that one or more saturated carbon atoms may be substituted for a heteroatom or heterogroup, such as O, S, NH and the like. For example an optionally substituted alkylene group could be represented by a group such as —$CH_2CH_2OCH_2$—, —$CH_2$—O—$CH_2$—, —$CH_2CH_2OCH_2CH_2OCH_2CH_2$—, —$CH_2CH_2NH$—$CH_2$—, —$CH_2NHCH_2$—, and the like.

Unless otherwise defined and only in respect of the ring atoms of non-aromatic carbocyclic or heterocyclic compounds, the ring atoms of such compounds may also be optionally substituted with one or two =O groups, instead of or in addition to the above described optional substituents.

When the optional substituent is or contains an alkyl, alkenyl, alkynyl, cycloalkyl, cycloalkenyl, aryl, heteroaryl or heterocyclyl group, the group may itself be optionally substituted with one to six of the same or different substituents selected from halogens, $C_{1-6}$ alkyl, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, $C_{1-6}$ alkylcarbonyl, $C_{1-6}$ alkoxycarbonyl and $CO_2H$.

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts.

It will be appreciated that the compounds of formula I, and the salts thereof, can be presented in the form of pharmaceutically acceptable derivatives. The term "pharmaceutically acceptable derivative" includes pharmaceutically acceptable esters, prodrugs, solvates and hydrates of the compounds of formula I or salts thereof. Pharmaceutically acceptable derivatives may include any pharmaceutically acceptable hydrate or any other compound or prodrug which, upon administration to a subject, is capable of providing (directly or indirectly) a compound of formula I or an active metabolite or residue thereof.

The pharmaceutically acceptable salts include acid addition salts, base addition salts, and the salts of quaternary amines and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, or tartaric acids. The counter ion of quaternary amines and pyridiniums include chloride, bromide, iodide, sulfate, phosphate, methanesulfonate, citrate, acetate, malonate, fumarate, sulfamate, and tartrate. The base addition salts include but are not limited to salts such as sodium, potassium, calcium, lithium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others. The salts may be made in a known manner, for example by treating the compound with an appropriate acid or base in the presence of a suitable solvent.

The compounds of the invention may be in crystalline form or as solvates (e.g. hydrates) and it is intended that both forms be within the scope of the present invention. The term "solvate" is a complex of variable stoichiometry formed by a solute (in this invention, a compound of the invention) and a solvent. Such solvents should not interfere with the biological activity of the solute. Solvents may be, by way of example, water, ethanol or acetic acid. Methods of solvation are generally known within the art.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine. Any compound that is a prodrug of a compound of the invention is within the scope and spirit of the invention.

The term "pharmaceutically acceptable ester" includes biologically acceptable esters of compound of the invention such as sulphonic, phosphonic and carboxylic acid derivatives.

Thus, in another aspect of the invention, there is provided a prodrug or pharmaceutically acceptable ester of a compound of formula I of salt thereof.

It will be appreciated that the compounds of formula I and some derivatives thereof may have at least one asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms with all isomeric forms of the compounds being included in the present invention.

In some preferred embodiments of the invention, and with reference to the general formula I, one or more of the following preferred definitions apply:

a) $R_1$ and $R_2$ are independently selected from hydrogen, lower alkyl or halo, and are preferably hydrogen or one of $R_1$ and $R_2$ is halo (preferably chloro) and the other hydrogen.

b) $R_5$ is an optionally substituted $C_{1-6}$ alkyl for example, preferably —$CH_2C(O)$ loweralkyl and $CH_2C(O)O$-loweralkyl, more preferably an unsubstituted $C_{1-6}$ alkyl and most preferably methyl.

Preferably, $R_1$ and $R_2$ are both hydrogen and $R_5$ is methyl, or $R_1$ is chloro, $R_2$ is hydrogen and $R_5$ is methyl.

c) One of $R_3$ and $R_4$ is optionally substituted $C_{1-10}$ alkyl, optionally substituted $C_{2-10}$ alkenyl, optionally substituted $C_{2-10}$ alkynyl, optionally substituted $C_{1-10}$ alkoxy, optionally substituted $C_{2-10}$ alkenyloxy, optionally substituted $C_{2-10}$ alkynyloxy. Preferably it is hydrogen, optionally substituted $C_{1-10}$ alkyl or optionally substituted $C_{1-10}$ alkoxy. More preferably $C_{1-2}$ alkoxy or $C_{1-3}$ alkyl. Most preferably methyl or methoxy.

d) The other of $R_3$ and $R_4$ is a substituted $C_{1-10}$ alkyl, substituted $C_{1-10}$ alkoxy group (preferably a lower alkyl or alkoxy group), substituted $C_{2-6}$ alkenyl, substituted $C_{2-6}$ alkenyloxy, substituted $C_{2-6}$ alkynyl or substituted $C_{2-6}$ alkynyloxy. More preferably a substituted methyl/methoxy, substituted ethyl/ethoxy, substituted propyl/propyloxy, substituted ethenyl/ethenyloxy, substituted propenyl/propenyloxy, substituted ethynyl/ethynyloxy, or substituted propynyl/propynyloxy group. In an embodiment the aforementioned groups are terminally substituted. Preferred substituents include optionally substituted aryl, optionally substituted aryloxy, optionally substituted heteroaryl, optionally substituted heteroaryloxy, optionally substituted heterocyclyl, optionally substituted heterocyclyloxy, and NR'R" where R' and R" independently represents hydrogen and lower alkyl.

Preferably $R_3$ is selected from the groups listed in c) and $R_4$ is selected from the groups listed in d).

Accordingly, in a preferred embodiment the present invention provides compounds of formula (Ia) or salts thereof,

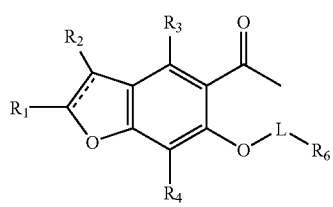

(Ia)

wherein
----- is an optional double bond;
$R_1$ is chloro or hydrogen;
$R_2$ is hydrogen;
$R_3$ is methyl or methoxy;
$R_4$ is selected from lower alkyl, lower alkoxy, $C_{2-6}$ alkenyl, $C_{2-6}$ alkenyloxy, $C_{2-6}$ alkynyl, or $C_{2-6}$ alkynyloxy, each substituted by optionally substituted aryl, optionally substituted aryloxy, optionally substituted heteroaryl, optionally substituted heteroaryloxy, optionally substituted heterocyclyl, optionally substituted heterocyclyloxy, or NR'R" (where R' and R" are independently selected from hydrogen and lower alkyl);
L is a divalent linker group of 1-6 atoms in length selected from optionally substituted alkylene, optionally substituted alkenylene, optionally substituted alkynylene; and
$R_6$ is selected from halo, CN, optionally substituted $C_{3-7}$ cycloalkyl, optionally substituted aryl, optionally substituted heteroaryl, optionally substituted heterocyclyl, —C(O)-heterocyclyl, —C(O)NR'''R''', —NR'''R''', —OR''', —SR''', —S(O)R''', —S(O)$_2$R''', —Se(O)R''', and —Se(O)$_2$R''' (where each R''' is independently selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl).

In other preferred embodiments of the invention, and with reference to the general formulae I and Ia, one or more of the following preferred definitions apply:
e) L is an optionally substituted alkylene (including for instance preferably CH$_2$OCH$_2$— and CH$_2$CH$_2$OCH$_2$CH$_2$—) and more preferably an unsubstituted alkylene group. Also, preferably L is a divalent linker group of from 2-4 atoms in length. Thus, most preferably L is an unsubstituted ethylene, propylene, or butylene group.
f) $R_6$ is halo, CN, optionally substituted aryl, optionally substituted heteroaryl, optionally substituted heterocyclyl, —C(O)-heterocyclyl, —C(O)NR'''R''', —NR'''R''', —OR''', —SR''', —S(O)R''', —S(O)$_2$R''', —Se(O)R''', and —Se(O)$_2$R''' (where R''' is selected from optionally substituted alkyl, optionally substituted $C_{3-7}$ cycloalkyl, optionally substituted heterocyclyl, optionally substituted heteroaryl and optionally substituted aryl). More preferably $R_6$ is CN, optionally substituted aryl, optionally substituted heteroaryl, optionally substituted heterocyclyl, —C(O)-heterocyclyl, —C(O)NR'''R''', —NR'''R''', —OR''', —SR''', —S(O)R''', or —S(O)$_2$R''' (where each R''' is independently selected from optionally substituted alkyl, optionally substituted $C_{3-7}$ cycloalkyl, optionally substituted heterocyclyl, optionally substituted heteroaryl and optionally substituted aryl).

Accordingly, in an even more preferred embodiment the present invention provides compounds of formula (Ia) or salts thereof wherein
----- is a double bond;
$R_3$ is methyl or methoxy;
$R_4$ is a lower alkyl or lower alkoxy terminally substituted by optionally substituted aryl, optionally substituted aryloxy, optionally substituted heteroaryl, optionally substituted heteroaryloxy, optionally substituted heterocyclyl, optionally substituted heterocyclyloxy, or NR'R" (where R' and R" are independently selected from hydrogen and lower alkyl);
L is a divalent linker group of 2-4 atoms in length selected from a ethylene, propylene or butylene; and
$R_6$ is CN, optionally substituted aryl, optionally substituted heteroaryl, optionally substituted heterocyclyl, —C(O)-heterocyclyl, —C(O)NR'''R''', —NR'''R''', —OR''', —SR''', —S(O)R''', or —S(O)$_2$R''' (where R''' is selected from optionally substituted alkyl, optionally substituted $C_{3-7}$ cycloalkyl, optionally substituted heterocyclyl, optionally substituted heteroaryl and optionally substituted aryl).

For the preferred groups listed in d) and f) above (in respect of $R_3$, $R_4$ and $R_6$) the optionally substituted alkyl, optionally substituted aryl, optionally substituted cycloalkyl, optionally substituted heteroaryl, optionally substituted heterocyclyl groups may be substituted with from 1 to 4 substituents. Preferably the substituents may be independently selected from fluoro, chloro, bromo, lower alkyl, lower haloalkyl, lower alkoxy, lower haloalkoxy, nitro, hydroxyl, carboxyl, phenyl, naphthyl, benzyl and benzoyl.

The invention also includes where possible a salt or pharmaceutically acceptable derivative such as a pharmaceutically acceptable ester, solvate and/or prodrug of the above mentioned embodiments of the invention.

In another aspect of the invention, there is provided a pharmaceutical composition that comprises a therapeutically effective amount of one or more of the aforementioned compounds of formulae I/Ia or pharmaceutically acceptable salts thereof, including pharmaceutically acceptable derivatives thereof, and optionally a pharmaceutically acceptable carrier or diluent.

In another aspect, the present invention provides pharmaceutical compositions for use as a Kv1.3 ion channel blocker, more particularly as an immunosuppressant, the composition comprising an effective amount of a compound of Formulae I/Ia or a pharmaceutically acceptable salt thereof, including a pharmaceutically acceptable derivative thereof, and optionally a pharmaceutically acceptable carrier or diluent.

The term "composition" is intended to include the formulation of an active ingredient with encapsulating material as carrier, to give a capsule in which the active ingredient (with or without other carrier) is surrounded by carriers.

The pharmaceutical compositions or formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomizing spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The invention also includes the compounds in the absence of carrier where the compounds are in unit dosage form.

The amount of compound of Formulae I/Ia administered may be in the range from about 10 mg to 2000 mg per day, depending on the activity of the compound and the disease to be treated.

Liquids or powders for intranasal administration, tablets or capsules for oral administration and liquids for intravenous administration are the preferred compositions.

The compositions may further contain one or more other immunosuppressive compounds. For example the compositions may contain a second immunosuppressive agent such as azathioprine, brequinar sodium, deoxyspergualin, mizoribine, mycophenolic acid morpholino ester, cyclosporin, FK-506 and rapamycin.

The compounds of the present invention may be useful in the therapeutic or prophylactic treatment of the resistance to transplantation of organs or tissue (such as heart, kidney, liver, lung, bone marrow, cornea, pancreas, intestinum tenue, limb, muscle, nervous, medulla ossium, duodenum, small-bowel, medulla ossium, skin, pancreatic islet-cell, etc. including xeno transplantation), graft-versus-host diseases; rheumatoid arthritis, systemic lupus erythematosus, nephrotic syndrome lupus, Palmo-planter pustulosis, Hashimoto's thyroiditis, multiple sclerosis, Guillain-Barre syndrome, myasthenia gravis, type I diabetes uveitis, juvenile-onset or recent-onset diabetes mellitus, diabetic neuropathy, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Meniere's disease, polyneuritis, multiple neuritis, mononeuritis, radiculopathy, hyperthyroidism, Basedow's disease, pure red cell aplasia, aplastic anaemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T-cell lymphoma, arteriosclerosis, atherosclerosis, aortitis syndrome, polyarteritis nodosa, myocardosis, scleroderma, Wegener's granuloma, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Sjoegren's syndrome, Addison's disease, ischemia-reperfusion injury of organs which occurs upon preservation, transplantation or ischemic disease, for example, thrombosis and cardiac infarction, endotoxin-shock, pseudomembranous colitis, colitis caused by drug or radiation, ischemic acute renal insufficiency, chronic renal insufficiency, toxinosis caused by lung-oxygen or drug, for example, paracort and bleomycins, lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-$C_4$ release; Berger's disease, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, preventing or treating activity of cytomegalovirus infection, HCMV infection, and antiinflammatory activity.

For certain of the abovementioned conditions it is clear that the compounds may be used prophylactically as well as for the alleviation of acute symptoms.

References herein to "treatment" or the like are to be understood to include such prophylactic treatment, as well as therapeutic treatments.

It is envisaged that the compounds may be particularly useful in the treatment of multiple sclerosis. This chronic neurological disorder affects the nerves of the central nervous system. As discussed earlier most nerves in the body are normally insulated by a protective sheath of fatty substance called myelin. Multiple sclerosis causes demyelination, in which this protective sheath becomes inflamed and ultimately destroyed.

By modulating or changing the immune system response that is thought to be responsible for the attack on the central nervous system it should be possible to attack the cause of the disease itself, rather than the more traditional method of controlling the symptoms.

The nature of the disease is such that it may be possible to control multiple sclerosis without unduly suppressing the patient's immune system. Based on the earlier discussed chronically activated human T-lymphocytes study, it is speculated that multiple sclerosis may be a product of chronically activated T-cells having a channel phenotype characterised by high expression of Kv1.3 channels and low numbers of IKCa1 channels. As this channel phenotype is distinct from that seen in quiescent and acutely activated cells it may provide a useful means for controlling multiple sclerosis without the significant side effects of less specific drugs.

Furthermore, in demyelinating diseases such as multiple sclerosis or diabetic neuropathy, the destruction of the myelin sheath evokes an internodal potassium current in myelinated nerve fibers by uncovering normally silent potassium channels. These abnormal potassium currents contribute to the conduction failure observed in demyelinated neurons. Blockers of axonal potassium channels such as the unselective compound 4-aminopyridine (4-AP) have been demonstrated to overcome conduction failure in vitro and to improve disability in certain multiple sclerosis patients. 4-AP (Fampridine) is currently in clinical trials for multiple sclerosis. Compounds that block both the Kv1.3 channel in autoreactive T-cells and the Kv1.1-Kv1.2 heteromultimeric channels present in the Ranvier Nodes of myelinated nerves might be ideally suited for the treatment of multiple sclerosis. Such compounds could simultaneously enhance impulse propagation in demyelinated neurons and modify the immune response.

Thus in another aspect of the invention there is provided a method of preventing or treating autoimmune or chronic inflammatory diseases, the prevention of rejection of foreign organ transplants and/or related afflictions, said method including the step of administrating a compound of formula I or Ia, or salt thereof, or a composition comprising the compound or salt thereof.

Accordingly in a preferred form of the invention, there is provided a means for controlling multiple sclerosis by the application of a blocker of the Kv1.3 channel, preferably a selective channel blocker of the Kv1.3 channel, and optionally also a blocker of Kv1.1 and/or Kv1.2 channels, by the application of a compound of formulae I/Ia or salt thereof, including a pharmaceutically acceptable derivative thereof, or a composition comprising the compound of formula I or salt thereof, or a pharmaceutically acceptable derivative thereof.

In another preferred form of the invention there is provided a method for preventing or treating diabetes including the step of administrating a compound of formulae I/Ia or a pharmaceutically acceptable salt thereof, including a pharmaceutically acceptable derivative thereof, or a composition comprising the compound or pharmaceutically acceptable salt thereof, or pharmaceutically acceptable derivative thereof.

In a further aspect, the invention provides a method of modulating potassium ion channel activity of T-cells by the application of a compound of Formulae I/Ia or a pharmaceutically acceptable salt thereof, including a pharmaceutically acceptable derivative thereof, or a composition comprising the same, to said T cells. Preferably the compounds of the invention inhibit the potassium ion channel activity of T-cells.

Preferably the potassium channel activity inhibited by the compound of Formulae I/Ia is a voltage-gated potassium channel, for example, Kv1.1-Kv1.7. More preferably the potassium ion channel activity is the voltage-gated potassium channel, Kv1.3 of a T-cell. Preferably the compound selectively inhibits the Kv1.3 channel, and optionally also the Kv1.1 and/or Kv1.2 channels.

In a further aspect of the present invention, there is provided the use of a compound of formulae I/Ia or salt thereof, in the preparation of a medicament for the treatment (therapeutic or prophylactic) of disease states mediated by potassium channels, and in particular by blocking the Kv1.3 channel.

In a further aspect of the invention there is provided a process for the production of the compounds of Formulae I/Ia or salts thereof, including pharmaceutically acceptable derivatives thereof.

The compounds of the invention can be made from khellin, a natural product from plants which is cheap and commercially available. A general synthetic scheme is set out below for those compounds where $R_5$ is methyl, and $R_3$ and $R_4$ includes an oxygen atom linking it to the parent structure:—

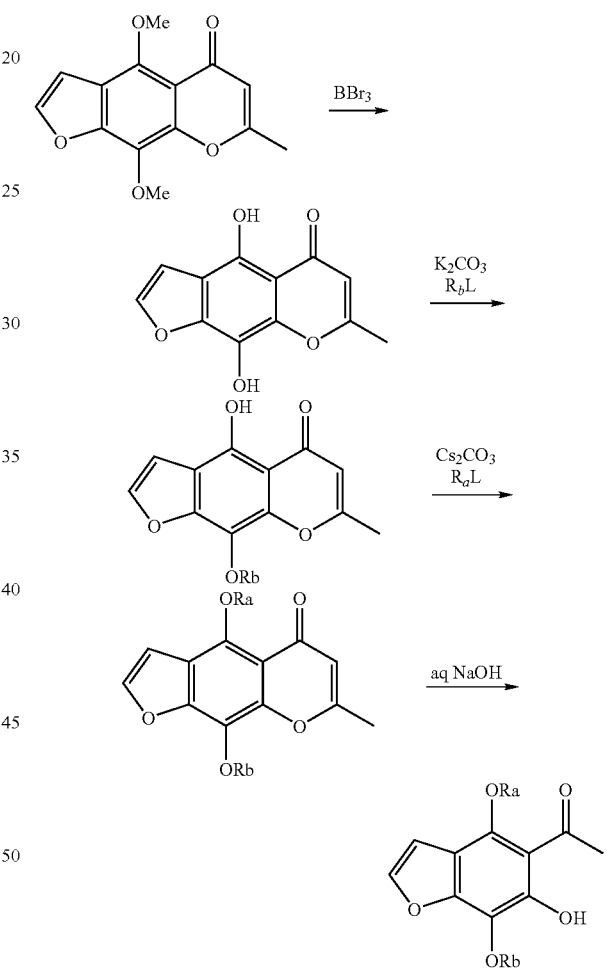

Where L is a halide leaving group and $R_a$ and $R_b$ are independently selected from optionally substituted alkyl, optionally substituted alkenyl, optionally substituted $C_{3-7}$ cycloalkyl, optionally substituted $C_{4-7}$ cycloalkenyl, optionally substituted alkynyl, i.e., where $R_3$ and $R_4$ are optionally substituted alkoxy, optionally substituted alkenyloxy, optionally substituted alkynyloxy, $C_{3-7}$ cycloalkyloxy, and $C_{4-7}$ cycloalkenyloxy.

The vinylogous ester containing six-membered ring of khellin acts as a protecting group for the ultimate phenol and acetyl functionalities during the manipulations of the ethers.

An alternate synthesis from khellinone can be envisaged where the phenol at the 6-position is capped with a suitable protecting group.

Compounds of the invention where $R_b$ is other than Me may be synthesised in accordance with the following scheme. This scheme is preferred when the reaction with the alkyl halide is facile.

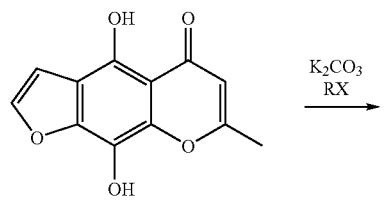

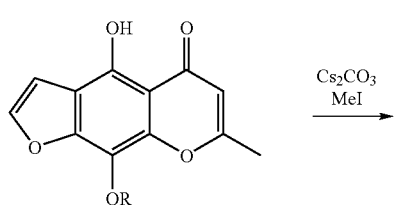

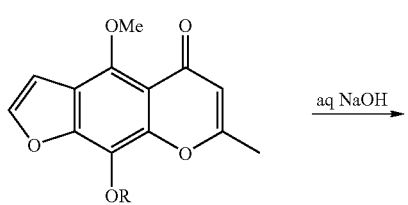

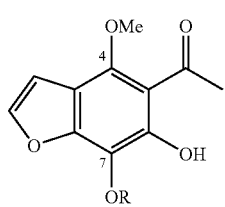

The alternative reaction scheme is preferred when the reaction with an alkyl halide is slow, due to, for instance, the low reactivity of alkyl halides such as alkyl chlorides. The scheme begins with the preparation of 7-desmethylkhellin, which can then be used to prepare the compounds of the invention.

Synthesis of intermediate 7-desmethylkhellin

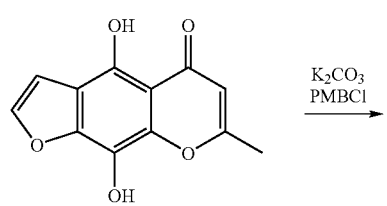

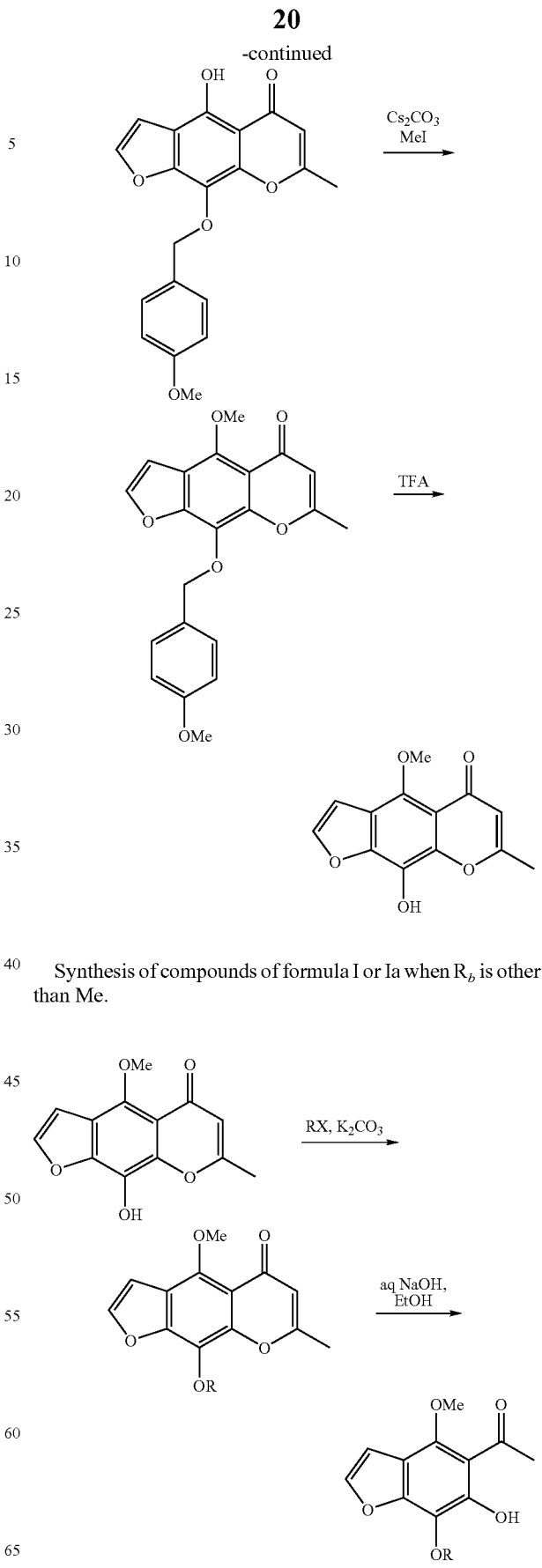

Synthesis of compounds of formula I or Ia when $R_b$ is other than Me.

A preferred embodiment of the compounds of the present invention are compounds where $R_4$ is an aryl-$(CH_2)_n$—O— substituted example (i.e., where $R_b$ is Ar—$(CH_2)_n$—, where n is 1 to 6). An alternative synthesis for this subset of compounds is shown below. Sonogashira coupling of 7-alkynyl khellin with an aryl iodide may furnish an aryl alkyne, which upon hydrogenation, reoxidation of the benzofuran, and hydrolysis may afford the desired aryl-$(CH_2)_n$—O— khellin. Heck coupling of 7-allyl khellin offers an alternate pathway to this class of compounds. Suitable coupling agents are known in the art and include Pd(PPh$_3$)$_2$Cl$_2$, Pd(PPh$_3$)$_4$, Pd(dibenzylideneacetone), and PdCl$_2$(CH$_3$CN)$_2$. Preferably the palladium catalysed coupling reactions include a co-catalyst, for instance, CuI, in the presence of a suitable base such as a trialkylamine base.

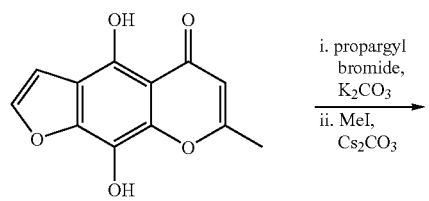

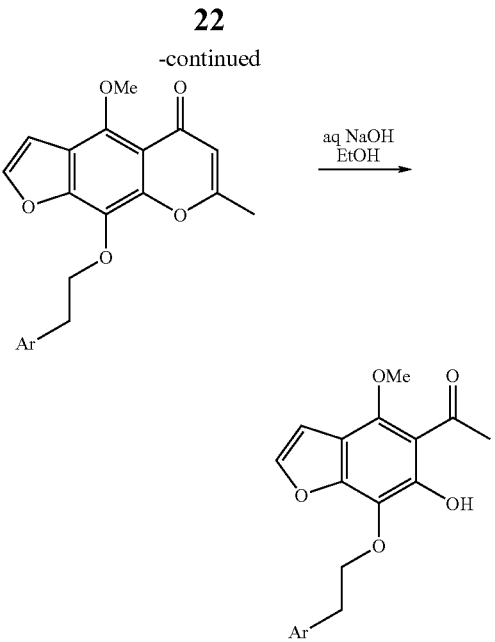

4-alkyl or 7-alkyl khellinones may be synthesised by the following prophetic schemes.

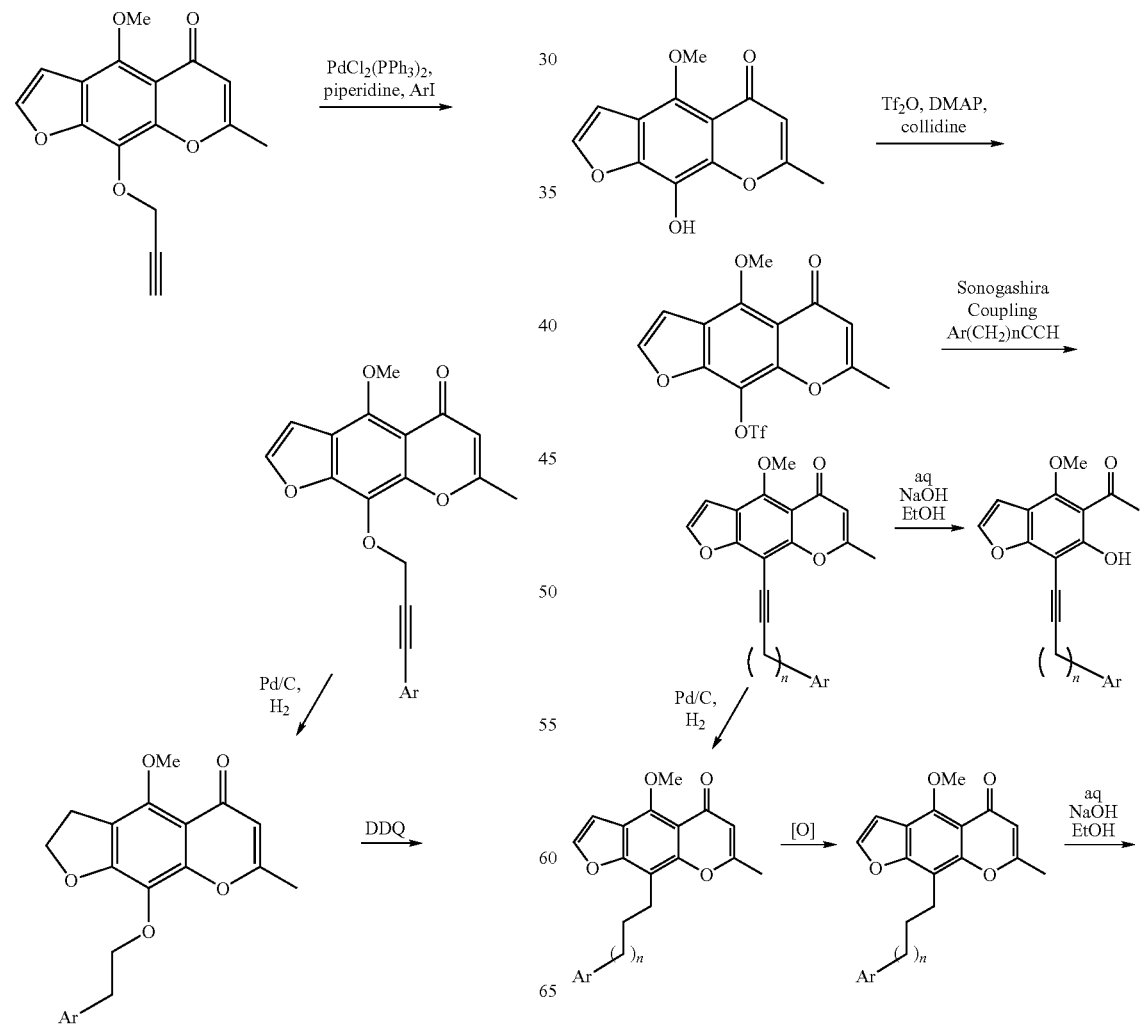

-continued

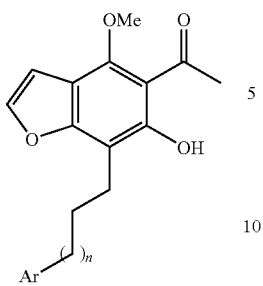

Starting with 7-triflyl khellin (or the 7-bromo visnagin (not shown)) Sonogashira coupling with an alkyne may provide the disubstituted alkyne. Reduction of the alkyne, followed by selective oxidation and alkaline hydrolysis, may give the 7-alkyl khellinone. Note that an analogous preparation could be envisaged for the generation of 4-alkyl khellinones starting from 4-triflyl khellin.

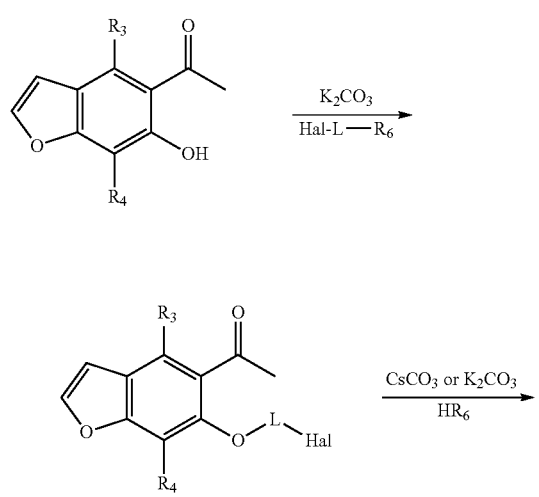

The L-$R_6$ group of the compounds of the present invention may be introduced according to the above scheme, where Hal represents a halogen.

As an alternative to the above Hal-L-$R_6$ could be a group Hal-L-Hal, as shown below:

-continued

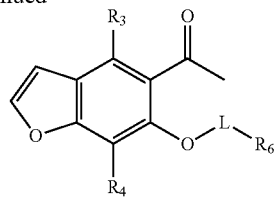

In the above scheme $HR_6$ is preferably a phenol, thiol or selenol.

Substituted benzofurans can be prepared by electrophilic aromatic substitution of the furan ring, including halogenation followed by palladium mediated coupling. Alternatively, the ring can be deprotonated using a base and an electrophile added or a palladium mediated coupling performed. Other approaches include ring opening the furan to give an ortho-formylphenols or salicilates that can be ring closed again introducing substituents.

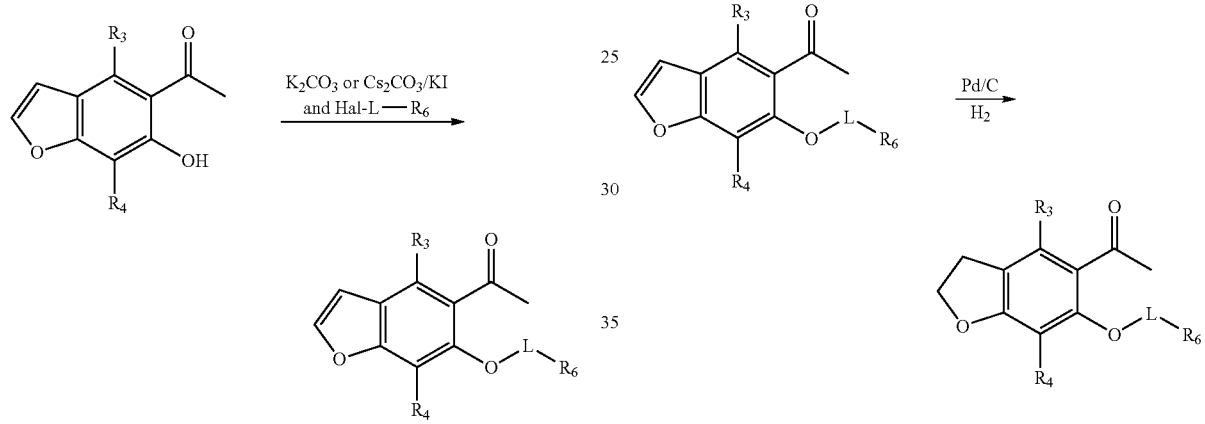

The above scheme illustrates that the reduced compounds (i.e., those where ≡≡≡ is a single bond) can be prepared by standard hydrogenation techniques, for instance, in the presence of 5% palladium on charcoal.

Compounds of formulae I/Ia where $R_5$ is other than Me may be prepared by transformation of the C-5 acetyl group in the kellinones referred to above. For instance the reaction of this group with an α-haloester in the presence of zinc (i.e. under Reformatsky conditions) may afford a βhydroxyester which may then be suitably oxidized to form a 3-carbonylester (i.e. where —C(O)—$R_5$ is —C(O)—CR'R"-$CO_2$R (where R' and R" are independently selected from H and lower alkyl, and R is lower alkyl, optionally substituted alkyl, optionally substituted aryl or optionally substituted arylalkyl).

Also, further substituents for $R_5$ can be added by initially halogenating the C-5 acetyl group with, for instance, $Br_2$ to form —C(O)$CH_2$Br. Substitution of the halogen with a suitable nucleophilic group may afford —C(O)$R_5$ where $R_5$ is —$CH_2$OR, and —$CH_2$SR, (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), or $CH_2$NR'R" (where R' and R" are independently selected from hydrogen or lower alkyl).

Furthermore, with the use of excess base and a halogen, the acetyl methyl group can be trihalogenated and cleaved via the haloform reaction to form a carboxylic acid (i.e. where $R_5$ is OH). Further transformation of the carboxylic acid, under conditions known in the art may produce esters (where $R_5$ is OR) and amides (where $R_5$ is —NR'R").

Also, the methyl or methylene groups a to the carbonyl (e.g. where $R_5$ is $CH_3$ or $CH_2CH_3$) can be oxidized with selenium dioxide to give respectively, α ketoaldehydes (i.e. $R_5$ is —C(O)H) and α-diketones (i.e. $R_5$ is —C(O)$CH_3$). In addition reacting the C-5 acetyl with an appropriate base and reacting the formed enolate with suitable acyl halides or dialkylcarbonates may afford compounds where $R_5$ is —$CH_2$C(O)R and —$CH_2$C(O)OR respectively, where R is preferably lower alkyl.

In the above schemes the following abbreviations were used:—
TFA trifluoroacetic acid
PMBCl para methoxybenzyl chloride
DMAP dimethylaminopyridine
Aq aqueous
$Tf_2O$ triflic anhydride Another variation is to add, remove or modify the substituents of the product to form new derivatives. This could be achieved by using standard techniques for functional group inter-conversion, well known in the industry such as those described in Comprehensive organic transformations: a guide to functional group preparations by Larock R C, New York, VCH Publishers, Inc. 1989.

Examples of possible functional group inter-conversions are: —C(O)NRR' from —$CO_2CH_3$ by heating with or without catalytic metal cyanide, e.g. NaCN, and HNRR' in $CH_3OH$; —OC(O)R from —OH with e.g., ClC(O)R' in pyridine; —NR—C(S)NR'R" from —NHR with an alkylisothiocyanate or thiocyanic acid; —NRC(O)OR from —NHR with alkyl chloroformate; —NRC(O)NR'R" from —NHR by treatment with an isocyanate, e.g. HN=C=O or RN=C=O; —NRC(O)R' from —NHR by treatment with ClC(O)R' in pyridine; —C(=NR)NR'R" from —C(NR'R")SR'" with $H_3NR^+OAc^-$ by heating in alcohol; —C(NR'R")SR from —C(S)NR'R" with R—I in an inert solvent, e.g. acetone; —C(S)NR'R" (where R' or R" is not hydrogen) from —C(S)$NH_2$ with HNR'R"; —C(=NCN)—NR'R" from —C(=NR'R")—SR with $NH_2CN$ by heating in anhydrous alcohol, alternatively from —C(=NH)—NR'R" by treatment with BrCN and NaOEt in EtOH; —NR—C(=NCN)SR from —NHR' by treatment with (RS)$_2$C=NCN; —NR"$SO_2R$ from —NHR' by treatment with Cl$SO_2R$ by heating in pyridine; —NR'C(S)R from —NR'C(O)R by treatment with Lawesson's reagent [2,4-bis(4-methoxyphenyl)-1,3,2,4-dithiadiphosphetane-2,4-disulfide]; —NR$SO_2CF_3$ from —NHR with triflic anhydride and base, —CH($NH_2$)CHO from —CH($NH_2$)C(O)OR' with Na(Hg) and HCl/EtOH; —$CH_2$C(O)OH from —C(O)OH by treatment with $SOCl_2$ then $CH_2N_2$ then $H_2O/Ag_2O$; —C(O)OH from —$CH_2$C(O)O$CH_3$ by treatment with PhMgX/HX then acetic anhydride then $CrO_3$; R—OC(O)R' from RC(O)R' by R"$CO_3H$; —$CCH_2OH$ from —C(O)OR' with Na/R'OH; —CHCH$_2$ from $CH_2CH_2OH$ by the Chugaev reaction; —$NH_2$ from —C(O)OH by the Curtius reaction; —$NH_2$ from —C(O)NHOH with TsCl/base then $H_2O$; —CHC(O)CHR from —CHCHOHCHR by using the Dess-Martin Periodinane regent or $CrO_3$/aq$H_2SO_4$/acetone; —$C_6H_5$CHO from —$C_6H_5CH_3$ with $CrO_2Cl_2$; —CHO from —CN with $SnCl_2$/HCl; —CN from —C(O)NHR with $PCl_5$; —$CH_2R$ from —C(O)R with $N_2H_4$/KOH; —S(O)$_2R$ from —SR with mCPBA.

In order that the present invention may be more readily understood, we provide the following non-limiting examples.

EXAMPLES

General Procedure

Synthetic Experimental
General Procedures
General Procedure A: Alkylation of Phenols and thiophenols:

A suspension of the phenol (1.0 equiv., 0.2 M), $Cs_2CO_3$ or $K_2CO_3$ (1.5 equiv.) and alkyl or benzyl halide (generally 1.2 equiv.) in anhydrous dimethylformamide was stirred under $N_2$ at 60° C. until completion as determined by TLC (3-5 h). The reaction mixture was then diluted with ethyl acetate and washed twice with either 10% citric acid or 2M HCl and then brine, dried over $MgSO_4$, and concentrated in vacuo. The crude product was purified by flash chromatography.

General Procedure B: Hydrolysis of Chromenones

To a solution of the chromenone (0.1-0.2 M) in ethanol (2 parts) at reflux was added slowly 3M NaOH (1 part) and the resulting solution was stirred at 90° C. for 3 h. The reaction mixture was acidified with 2M HCl and then extracted twice with ethyl acetate. The pooled organics were washed with brine, dried over $MgSO_4$ and concentrated in vacuo. If necessary the crude product was purified by silica-gel flash chromatography.

General Procedure C: Alkylations of Aniline

To a solution of the alkyl bromide (1 eq, 0.3-0.4 M) in N-methylpyrrolidinone was added aniline (3 eqs) and the reaction stirred at 90-95° C. for 16 h. The reaction was cooled, quenched with 10% citric acid and extracted with ethyl acetate or dichloromethane. The organic layer was washed with water and brine, dried over $MgSO_4$ and concentrated in vacuo. The crude residue was purified by silica-gel flash chromatography.

General Procedure D: Demethylation of 9-Methoxy Analogues

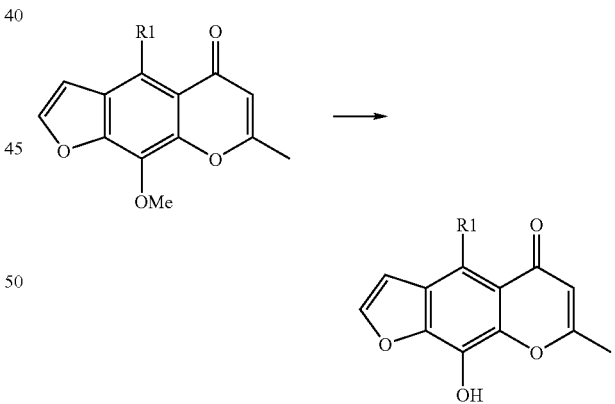

A solution of the methyl ether (1.0 eq.) in dichloromethane (0.2 M) was cooled to −78° C. and a solution of $BBr_3$ in dichloromethane (1M, 1.5 eq.) was added over 2 min. The reaction mixture was stirred at −78° C. for 10 min then at rt overnight. The reaction vessel was placed into an ice-bath and water was added to quench the reaction. The dichloromethane was removed in vacuo and the resulting suspension was acidified with dilute citric acid to give a final concentration of 2% citric acid. The suspension was heated at 70° C. for 1 h then filtered, washing with water. The resulting solid was dried under high vacuum to give the product.

General Procedure E: Alkylations of Amines and N-Heterocycles

To a solution of the bromide (0.2-0.5 M) in anhydrous dimethylformamide was added the amine or N-heterocycle (3-6 eqs) and the reaction was stirred at 80-90° C. under a $N_2$ atmosphere until the reaction was complete by TLC (~5 h). The reaction was quenched with saturated aqueous $NH_4Cl$ solution and extracted with ethyl acetate. The organic layer was washed with water then brine, dried over $MgSO_4$ and concentrated under vacuum. The crude residue was purified by silica gel flash chromatography.

General Procedure F: Hydrogenation of Benzofuran Derivatives

A suspension of the benzofuran (1.0 eq.), and 10% palladium on carbon (20% by weight) in methanol (0.1 M) was stirred under $H_2$ at it for 16 h. The reaction mixture was filtered through a Celite pad, washing with methanol and dichloromethane. The solvent was concentrated in vacuo and the crude product was purified by flash chromatography when required.

General Procedure G: 4-Alkylation of Khellin Derivatives

The khellin and khellinone derivatives which were alkylated at the 4-position were generally synthesised in accordance with the following general reaction scheme.

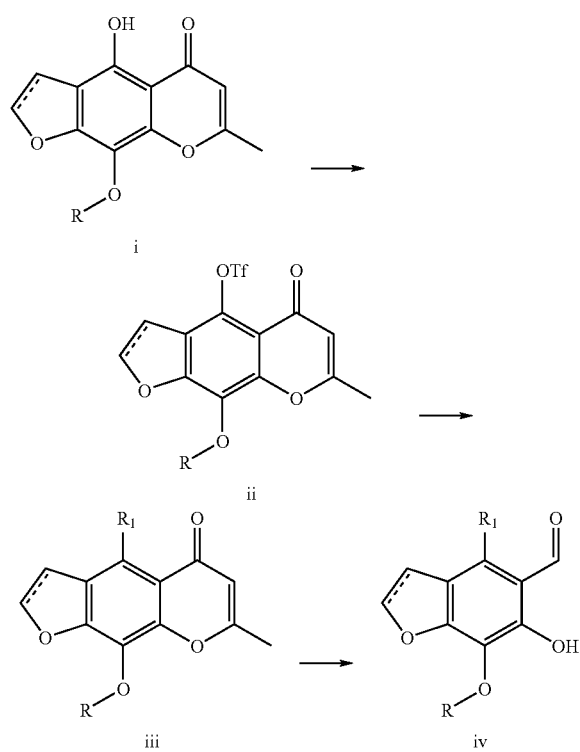

Step 1: Phenol derivative i (1.0 eq., 0.2 M) was dissolved in dry DCM and cooled to 0° C. under $N_2$. Anhydrous pyridine (4.0 eq.) was added to it, followed by triflic anhydride (1.5 eq.) slowly under $N_2$. The reaction temperature was slowly raised to it and stirred overnight under $N_2$. The reaction was cooled and quenched by addition of aqueous $NH_4Cl$ (saturated) solution and extracted with DCM. The organic layer was separated, dried over $MgSO_4$ (anhydrous), filtered and concentrated under vacuum. The dark brownish residue was subjected to flash column chromatography to give crude triflate ii as a solid, which was used as such without further purification.

Step 2: $ZnBr_2.2H_2O$ (4.0 eq.) was dried at 115-120° C. for 2.0 h in RB flask with occasional mixing under high vacuum. After drying, the flask was cooled to rt under $N_2$ and then dissolved in dry tetrahydrofuran (6 ml for 800 mg of $ZnBr_2$). The clear solution was cooled to −78° C. under $N_2$ atmosphere and then 4.0 mmol of RLi (MeLi was 1.6 M in diethylether and EtLi was 0.5 M in benzene/cyclohexane 9/1) was added slowly by syringe. The reaction temperature was allowed to warm to it slowly and stirred for 15 min and then again cooled to −78° C. under $N_2$ atmosphere. CuI (0.15 eq.) and $PdCl_2(PPh_3)_2$ (0.12 eq.) were added to the reaction mixture and the reaction vessel was evacuated and back-filled with $N_2$. The triflate derivative ii ($R_1$=Me or 3-phenylpropyl) (1.0 eq.), dissolved in the minimum amount of dry tetrahydrofuran, was added and again flushed with $N_2$. The reaction mixture was stirred at room temperature for 48 hours. After this the reaction was cooled to 0° C. and quenched by addition of aqueous $NH_4Cl$ solution and extracted with ethyl acetate. The organic layer was dried over $MgSO_4$, evaporated and the crude residue was purified by flash chromatography using dichloromethane as eluent to afford iii.

Step 3: Khellin derivative iii (0.22 mmol) was dissolved in a mixture of 2 ml of ethanol (2 mL) and 3 M NaOH (1 mL). The reaction mixture was heated at 85-95° C. for 3 hours and then cooled to rt. The reaction was diluted with 10% citric acid (10 mL) and then extracted with ethyl acetate (20 mL) and washed with water. The organic layer was separated, dried over $MgSO_4$ and evaporated under vacuum. The residue was purified by flash chromatography using dichloromethane as eluent to afford iv.

General Procedure H:

A suspension of the phenol (1.0 eq.), $Cs_2CO_3$ (2.0 eq.), KI (2.0 eq.) and the alkyl chloride (1.5 eq.) in anhydrous dimethylformamide (2 ml) was stirred under $N_2$ at a temperature between 60° C. and 85° C. for between 16 h and 48 h. After this time the reaction was cooled, quenched with water (20 ml) and extracted with ethyl acetate (20 ml). The organic layer was washed with water (2×20 ml) and brine (10 ml), dried over $MgSO_4$ and concentrated in vacuo. The crude residue was purified by flash chromatography.

General Procedure I:

To a stirred suspension the phenol (1.0 eq.), $K_2CO_3$ (2.0 eq.) and NaI (0.30 eq.), predried under vacuum at 100° C. for 5 h) in dry dimethylformamide or dimethylsulfoxide (0.1 M of phenol) was added the alkyl chloride (2.0 eq.) and the reaction was heated at 60° C. for 16 h. After this time the reaction was cooled, diluted with ethyl acetate and washed thrice with water. The organic layer was dried over $MgSO_4$, concentrated in vacuo and the crude residue was purified by silica-gel flash chromatography Example 1

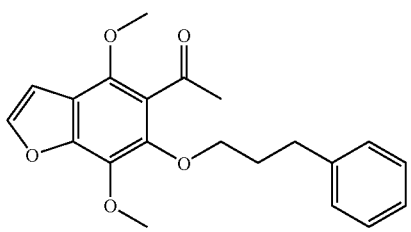

5-Acetyl-4,7-dimethoxy-6-(3-(phenyl)propoxy)benzofuran

Khellinone (59 mg, 0.25 mmol) and 3-(phenyl)propylbromide (46 µL, 0.30 mmol) were treated as described under General Procedure A to afford the title compound (76 mg, 85%) as a colourless solid: $^1$H NMR (300 MHz, CDCl$_3$): δ 2.03 (m, 2H), 2.53 (s, 3H), 2.76 (t, J=7.8 Hz, 2H), 3.97 (s, 3H), 4.03 (s, 3H), 4.08 (t, J=6.3 Hz, 2H), 6.86 (d, J=2.4 Hz, 1H), 7.14-7.30 (m, 5H), 7.56 (d, J=2.4 Hz, 1H). MS (ES$^+$) m/z 355.1 (M+H$^+$).

Example 2

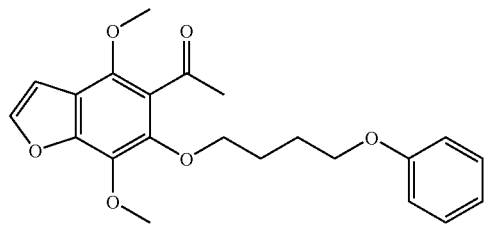

5-Acetyl-4,7-dimethoxy-6-(4-(phenoxy)butoxy))benzofuran

Khellinone (55 mg, 0.25 mmol) and 4-(phenoxy)butylbromide (69 mg, 0.30 mmol) were treated as described under General Procedure A to afford the title compound (73 mg, 78%) as a brown oil: $^1$H NMR (300 MHz, CDCl$_3$): δ 1.90 (m, 4H), 2.51 (s, 3H), 3.97 (s, 3H), 3.98-4.04 (m, 5H), 4.11 (t, J=5.9 Hz, 2H), 6.85 (d, J=2.3 Hz, 1H), 6.92 (m, 3H), 7.26 (t, J=8.5 Hz, 2H), 7.56 (d, J=2.3 Hz, 1H). MS (ES$^+$) m/z 385.0 (M+H$^+$).

Example 3

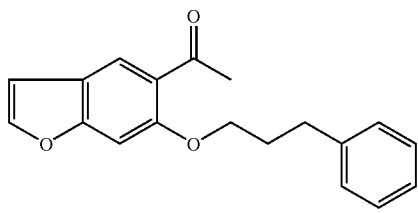

5-Acetyl-6-(3-phenylpropoxy)benzofuran

5-Acetyl-6-hydroxybenzofuran (60 mg, 0.34 mmol) and 1-bromo-3-phenylpropane were reacted according to General Procedure A. The crude residue was purified by flash chromatography, eluting with diethyl ether:petroleum ether (1:9) to afford the title compound as a white solid (81 mg, 81%). $^1$H NMR (300 MHz, CDCl$_3$): δ 2.26-2.16 (m, 2H), 2.69 (s, 3H), 2.85 (t, J=7.3 Hz, 2H), 4.07 (t, J=6.3 Hz, 2H), 6.72 (d, J=1.7 Hz, 1H), 6.99 (s, 1H), 7.32-7.19 (m, 5H), 7.54 (d, J=2.2 Hz, 1H), 7.99 (s, 1H). MS (ES$^+$) m/z 294.9 (M+H$^+$).

Example 4

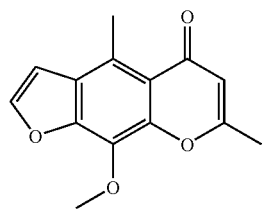

4a) 9-methoxy-4,7-dimethyl-5H-furo[3,2-g]chromen-5-one

9-Methoxy-7-methyl-4-trifluoromethanesulfonyl-5H-furo[3,2-g]chromen-5-one (324 mg, 1.0 mmol), ZnBr$_2$.H$_2$O (1.04 g, 4.0 mmol), CuI (28 mg, 0.15 mmol), PdCl$_2$(PPh$_3$)$_2$ (84 mg, 0.12 mmol) and MeLi (2.5 ml of 1.6 M in diethyl-ether, 4.0 mmol) were treated as described under General Procedure G (Step 2) to afford the title compound (Yield 70%). $^1$H NMR (300 MHz, CDCl$_3$): δ 2.38 (s, 3H, Me), 2.94 (s, 3H, Me), 4.21 (s, 3H, OMe), 6.05 (s, 1H), 6.91 (d, J=2.4, 1H), 7.65 (d, J=2.4, 1H). MS (ES) m/z: 244.9 (M+H$^+$).

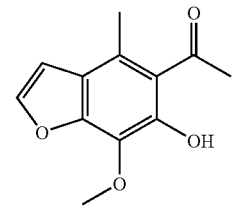

4b) 5-Acetyl-6-hydroxy-7-methoxy-4-methylbenzofuran

The title compound was prepared from Example 4a) utilising General Procedure G (Step 3) in 65% yield. $^1$H NMR (300 MHz, CDCl$_3$): δ 2.53 (s, 3H, Me), 2.64 (s, 3H, Me), 4.13 (s, 3H, OCH3), 6.74 (d, J=2.4, 1H), 7.52 (d, J=2.4, 1H), 9.27 (s, 1H, OH). MS (ES) m/z: 220.9 (M+H$^+$).

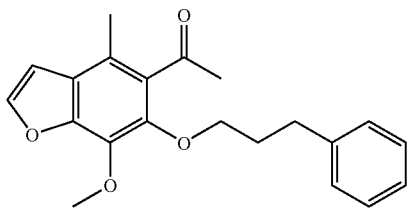

4c) 5-Acetyl-4-methyl-7-methoxy-6-(3-(phenyl)propoxy)benzofuran

Compound from Example 4b) (40 mg, 0.18 mmol), anhydrous K$_2$CO$_3$ (50 mg, 0.36 mmol) and 1-bromo-3-(phenyl)- propane (43 mg, 0.22 mmol) were treated according to General Procedure A. The residue was purified by flash column chromatography to offer the title compound in 80% yield. $^1$H NMR (300 MHz, CDCl$_3$) δ: 1.98-2.08 (m, 2H), 2.31 (s, 3H, CH$_3$), 2.53 (s, 3H, OCH$_3$), 2.76 (t, J=7.6, 2H), 4.04 (t, J=6.3, 2H), 4.10 (s, 3H, OCH$_3$), 6.739d, J=2.1, 1H), 7.15-7.30 (m, 5H), 7.58 (d, J=2.1, 1H). MS (ES) m/z: 338.9 (M+H$^+$).

Example 5

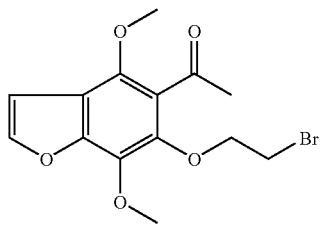

5a)
5-Acetyl-6-(2-bromoethoxy)-4,7-dimethoxybenzofuran

Khellinone (850 mg, 3.6 mmol, 0.4 M), K$_2$CO$_3$ (3 eqs) and 1,2-dibromoethane (3 eqs) were reacted according to General Procedure A. The crude product was purified by flash chromatography, eluting with ethyl acetate:petroleum ether (15:85) to afford the title compound as a clear oil (1.02 g, 83%). $^1$H NMR (300 MHz, CDCl$_3$): δ 2.53 (s, 3H), 3.57 (t, J=6.3 Hz, 2H), 3.98 (s, 3H), 4.07 (s, 3H), 4.35 (t, J=6.3 Hz, 2H), 6.86 (d, J=2.2 Hz, 1H), 7.57 (d, J=2.2 Hz, 1H). MS (ES$^+$) m/z 342.8/344.8 (M+H$^+$).

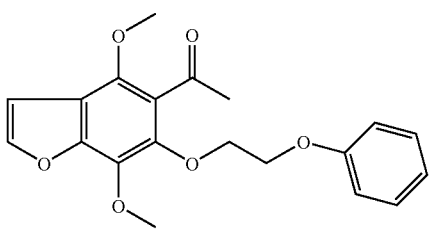

5b) 5-Acetyl-4,7-dimethoxy-6-(2-(phenoxy)ethoxy)
benzofuran

Example 5a) (55 mg, 0.16 mmol, 0.1 M), Cs$_2$CO$_3$ (2 eqs) and phenol (1.5 eqs) were reacted according to General Procedure A. The crude product was purified by flash chromatography, eluting with ethyl acetate:petroleum ether (1:9) to afford the title compound as a clear oil (48 mg, 84%). $^1$H NMR (300 MHz, CDCl$_3$): δ 2.52 (s, 3H), 3.97 (s, 3H), 4.07 (s, 3H), 4.22 (m$_c$, 2H), 4.42 (m$_c$, 2H), 6.86 (d, J=2.1 Hz, 1H), 6.91-6.96 (m, 3H), 7.24-7.30 (m, 2H), 7.57 (d, J=2.1 Hz, 1H). MS (ES$^+$) m/z 356.9 (M+H$^+$).

Example 6

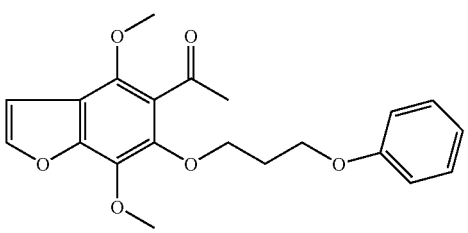

6a) 5-Acetyl-6-(3-bromopropoxy)-4,7-dimethoxy-
benzofuran

Khellinone (400 mg, 1.7 mmol, 0.3 M), K$_2$CO$_3$ (3 eqs) and 1,3-dibromopropane (3 eqs) were reacted according to General Procedure A. The crude product was purified by flash chromatography, eluting with ethyl acetate:petroleum ether (15:85) to afford the title compound as a clear oil (530 mg, 88%). $^1$H NMR (300 MHz, CDCl$_3$): δ 2.24 (quintet, J=6.2 Hz, 2H), 2.51 (s, 3H), 3.57 (t, J=6.6 Hz, 2H), 3.97 (s, 3H), 4.07 (s, 3H), 4.19 (t, J=6.4 Hz, 2H), 6.86 (d, J=2.2 Hz, 1H), 7.56 (d, J=2.2 Hz, 1H). MS (ES$^+$) m/z 356.8/358.8 (M+H$^+$).

6b) 5-Acetyl-4,7-dimethoxy-6-(3-(phenoxy)pro-
poxy)benzofuran

Example 6a) (50 mg, 0.14 mmol, 0.1 M), Cs$_2$CO$_3$ (2.5 eqs) and phenol (1.5 eqs) were reacted according to General Procedure A. The crude product was purified by flash chromatography, eluting with ethyl acetate:petroleum ether (1:9) to afford the title compound as a clear oil (40 mg, 77%). $^1$H NMR (300 MHz, CDCl$_3$): δ 2.18 (quintet, J=6.2 Hz, 2H), 2.48 (s, 3H), 3.96 (s, 3H), 4.00 (s, 3H), 4.13 (t, J=6.2 Hz, 2H), 4.24 (t, J=6.1 Hz, 2H), 6.85 (d, J=2.2 Hz, 1H), 6.90-6.94 (m, 3H), 7.24-7.29 (m, 2H), 7.55 (d, J=2.2 Hz, 1H). MS (ES$^+$) m/z 370.9 (M+H$^+$).

Example 7

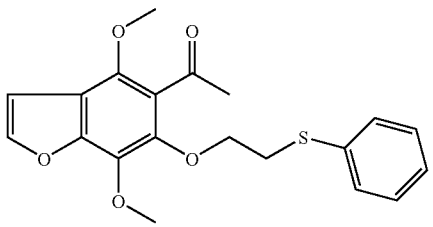

5-Acetyl-4,7-dimethoxy-6-(2-(thiophenoxy)ethoxy)benzofuran

Example 5a) (55 mg, 0.16 mmol, 0.1 M), K$_2$CO$_3$ (2.5 eqs) and thiophenol (1.5 eqs) were reacted according to General Procedure A. The crude product was purified by flash chromatography, eluting with ethyl acetate:petroleum ether (1:9) to afford the title compound as a clear oil (55 mg, 92%). $^1$H NMR (300 MHz, CDCl$_3$): δ 2.51 (s, 3H), 3.23 (t, J=7.2 Hz, 2H), 3.96 (s, 3H), 4.01 (s, 3H), 4.21 (t, J=7.1 Hz, 2H), 6.85 (d, J=2.2 Hz, 1H), 7.14-7.20 (m, 1H), 7.24-7.29 (m, 2H), 7.36-7.39 (m, 2H), 7.55 (d, J=2.2 Hz, 1H). MS (ES$^+$) m/z 372.9 (M+H$^+$).

Example 8

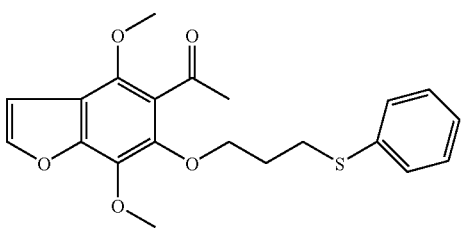

5-Acetyl-4,7-dimethoxy-6-(3-(phenylthio)propoxy)benzofuran

Example 6a) (50 mg, 0.14 mmol, 0.1 M), K$_2$CO$_3$ (2.5 eqs) and thiophenol (1.5 eqs) were reacted according to General Procedure A. The crude product was purified by flash chromatography, eluting with ethyl acetate:petroleum ether (1:9) to afford the title compound as a clear oil (50 mg, 92%). $^1$H NMR (300 MHz, CDCl$_3$): δ 1.98-2.07 (m, 2H), 2.50 (s, 3H), 3.08 (t, J=7.1 Hz, 2H), 3.97 (s, 3H), 4.04 (s, 3H), 4.15 (t, J=6.0 Hz, 2H), 6.85 (d, J=2.2 Hz, 1H), 7.13-7.20 (m, 1H), 7.24-7.29 (m, 2H), 7.33-7.36 (m, 2H), 7.56 (d, J=2.2 Hz, 1H). MS (ES$^+$) m/z 386.9 (M+H$^+$).

Example 9

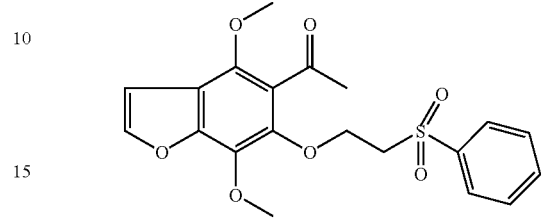

5-Acetyl-4,7-dimethoxy-6-(2-(benzenesulfonyl)ethoxy)benzofuran

To a solution of the sulfide of Example 7 (25 mg, 0.067 mmol) in dichloromethane (1.5 mL) was added meta-chloroperbenzoic acid (50 mg, ~70% purity, 3 eqs) and the reaction was stirred for 16 h at room temperature. During this time formation of a precipitate was observed. The reaction was diluted with dichloromethane (20 mL) and quenched with saturated aqueous NaHCO$_3$ (20 mL). The organic layer was washed with another portion of saturated aqueous NaHCO$_3$ and brine, dried over MgSO$_4$ and concentrated in vacuo. The crude residue was purified by flash chromatography, eluting with ethyl acetate:petroleum ether (3:7) to afford the title compound as a clear resin (14 mg, 52%). $^1$H NMR (300 MHz, CDCl$_3$): δ 2.38 (s, 3H), 3.56 (t, J=6.7 Hz, 2H), 3.94 (s, 3H), 4.03 (s, 3H), 4.40 (t, J=6.7 Hz, 2H), 6.84 (d, J=2.2 Hz, 1H), 7.52-7.65 (m, 4H), 7.94 (d, J=7.2 Hz, 2H). MS (ES$^+$) m/z 404.9 (M+H$^+$).

Example 10

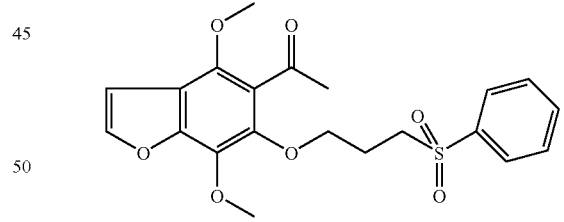

5-Acetyl-4,7-dimethoxy-6-(3-(benzenesulfonyl)propoxy)benzofuran

To a solution of the sulfide of Example 8 (30 mg, 0.078 mmol) in dichloromethane (1.5 mL) was added meta-chloroperbenzoic acid (58 mg, ~70% purity, 3 eqs) and the reaction was stirred for 2.5 h at room temperature. The reaction was diluted with dichloromethane (20 mL) and quenched with saturated aqueous NaHCO$_3$ (20 mL). The organic layer was washed with another portion of saturated aqueous NaHCO$_3$ and brine, dried over MgSO$_4$ and concentrated in vacuo. The crude residue was purified by flash chromatography, eluting sequentially with ethyl acetate:petroleum ether (1:3 then 1:2) to afford the title compound as a clear resin (20 mg, 61%). $^1$H NMR (300 MHz, CDCl$_3$): δ 2.05-2.14 (m, 2H), 2.45 (s, 3H), 3.32 (m$_c$, 2H), 3.95 (s, 3H), 4.01 (s, 3H), 4.07 (t, J=5.8 Hz, 2H), 6.84 (d, J=2.2 Hz, 1H), 7.54-7.67 (m, 4H), 7.94 (d, J=7.1 Hz, 2H). MS (ES$^+$) m/z 418.9 (M+H$^+$).

Example 11

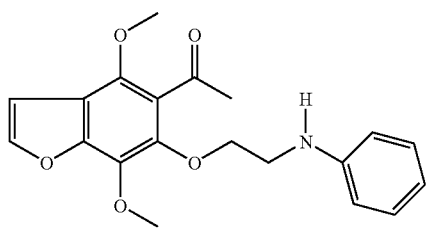

5-Acetyl-4,7-dimethoxy-6-(2-(phenylamino)ethoxy)benzofuran

Bromide of Example 5a) (60 mg, 0.17 mmol) was treated according to General Procedure C. The crude product was purified by flash chromatography eluting with ethyl acetate:petroleum ether (1:9) to afford the title compound as a viscous oil (18 mg, 30%). $^1$H NMR (300 MHz, CDCl$_3$): δ 2.51 (s, 3H), 3.40 (br t, J=4.8 Hz, 2H), 3.98 (s, 3H), 4.05 (s, 3H), 4.29 (t, J=4.8 Hz, 2H), 4.50 (br s, 1H), 6.65-6.71 (m, 3H), 6.86 (dd, J=0.7, 2.2 Hz, 1H), 7.16 (t, J=7.8 Hz, 2H), 7.57 (dd, J=0.7, 2.2 Hz, 1H). MS (ES$^+$) m/z 355.9 (M+H$^+$).

Example 12

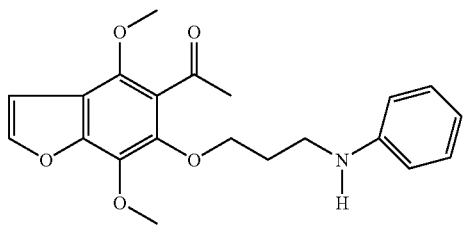

5-Acetyl-4,7-dimethoxy-6-(3-(phenylamino)propoxy)benzofuran

Bromide of Example 6a) (60 mg, 0.17 mmol) was treated according to General Procedure C. The crude product was purified by flash chromatography eluting with ethyl acetate:petroleum ether (15:85) to afford the title compound as a viscous oil (48 mg, 77%). $^1$H NMR (300 MHz, CDCl$_3$): δ 2.00 (quintet, J=6.1 Hz, 2H), 2.52 (s, 3H), 3.34 (br t, J=6.4 Hz, 2H), 3.98 (s, 3H), 4.05 (s, 3H), 4.14 (t, J=5.8 Hz, 2H), 6.63- 6.69 (m, 3H), 6.86 (d, J=2.1 Hz, 1H), 7.16 (t, J=8.2 Hz, 2H), 7.57 (d, J=2.1 Hz, 1H). MS (ES$^+$) m/z 369.9 (M+H$^+$).

Example 13

13a) 5-Acetyl-7-N,N-dimethylaminomethyl-6-hydroxy-4-methoxybenzofuran

To a solution of visnaginone (103 mg, 0.50 mmol) in anhydrous ethanol (2 mL) was added dimethylamine (116 μL, 0.65 mmol) and formalin (37 wt. %, 49 μL, 0.65 mmol) and this was stirred at 90° C. for 16 h before concentrating in vacuo. The resulting residue was purified by flash chromatography eluting with dichloromethane/ethyl acetate (7:3) then with dichloromethane/ethyl acetate (7:3) plus 1% triethylamine to afford the title compound (51 mg, 39%) as a yellow solid: $^1$H NMR (300 MHz, CD$_3$CN): δ 2.30 (s, 6H), 2.53 (s, 3H), 3.79 (s, 2H), 4.07 (s, 3H), 7.00 (d, J=2.4 Hz, 1H), 7.58 (d, J=2.4 Hz, 1H). MS (ES$^+$) m/z 264.0 (M+H$^+$).

13b) 5-Acetyl-7-N,N-dimethylaminomethyl-4-methoxy-6-(3-(phenyl)propoxy)benzofuran Example 13a) (33 mg, 0.13 mmol) and 3-(phenyl)propyl-bromide (23 μL, 0.15 mmol) were treated as described under General Procedure A. The crude product was purified by flash chromatography eluting with dichloromethane/ethyl acetate (7:3) to afford the title compound (18 mg, 38%) as a brown solid: $^1$H NMR (300 MHz, CDCl$_3$): δ 2.05 (m, 2H), 2.26 (s, 6H), 2.53 (s, 3H), 2.77 (t, J=7.8 Hz, 2H), 3.63 (s, 2H), 3.94 (t, J=6.3 Hz, 2H), 4.05 (s, 3H), 6.88 (d, J=2.4 Hz, 1H), 7.15-7.31 (m, 5H), 7.58 (d, J=2.4 Hz, 1H). MS (ES⁺) m/z 382.1 (M+H⁺).

Example 14

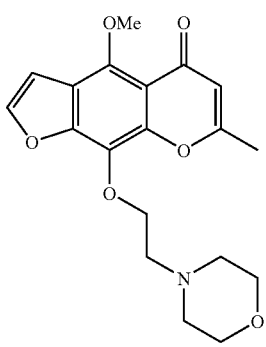

14a) 4-Methoxy-7-methyl-9-(2-(N-morpholino)ethoxy)furo[3,2-g]chromen-5-one

A suspension of 9-desmethylkhellin (123 mg, 0.50 mmol), 4-(2-chloroethyl)morpholine hydrochloride (140 mg, 0.75 mmol), caesium carbonate (487 mg, 1.5 mmol) and potassium iodide (83 mg, 0.50 mmol) in DMF (2.5 mL) was stirred at 60° C. for 72 h. The reaction mixture was treated with water (8 mL), then filtered washing with water, and dried to give the title compound (83 mg, 46%) as a brown solid: ¹H NMR (300 MHz, CDCl₃): δ 2.35 (s, 3H), 2.69 (m, 4H), 2.91 (m, 2H), 3.76 (m, 4H), 4.05 (s, 3H), 4.49 (m, 2H), 6.04 (s, 1H), 7.00 (d, J=2.3 Hz, 1H), 7.60 (d, J=2.3 Hz, 1H).

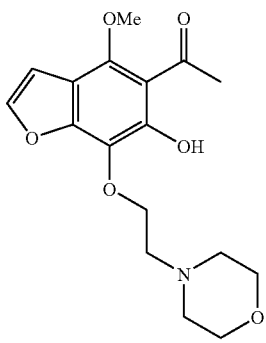

14b) 5-Acetyl-4-methoxy-6-hydroxy-7-(2-(N-morpholino)ethoxy-benzofuran

To a solution of Example 14a) (54 mg, 0.15 mmol) in ethanol (1.5 mL) at 60° C. was added 3M NaOH (1.5 mL) and the reaction mixture was stirred at 60° C. for 5 h. The solution was concentrated in vacuo to half its original volume and the pH was adjusted to pH8 by Universal Indicator using 10% citric acid solution and saturated sodium bicarbonate solution. The solution was extracted with ethyl acetate (3×10 mL) and the pooled organics were dried over Na₂SO₄ and concentrated in vacuo to give the title compound (25 mg, 46%) as a brown oil: ¹H NMR (300 MHz, CDCl₃): δ 2.64 (s, 3H), 2.75 (m, 4H), 2.83 (t, J=5.2 Hz, 2H), 3.81 (m, 4H), 4.07 (s, 3H), 4.32 (t, J=5.2 Hz, 2H), 6.85 (d, J=2.3 Hz, 1H), 7.46 (d, J=2.3 Hz, 1H).

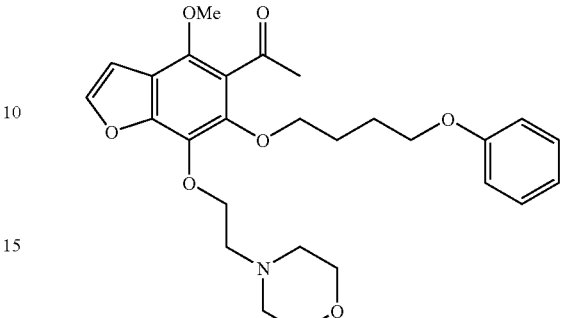

14c) 5-Acetyl-4-methoxy-7-(2-(N-morpholino)ethoxy-6-(4-(phenoxy)butoxy)) benzofuran Example 14b) (15 mg, 0.045 mmol) and 4-(phenoxy)butylbromide (12 mg, 0.054 mmol) were treated as described under General Procedure A. The crude was purified by flash chromatography eluting with dichloromethane to afford the title compound (13 mg, 59%) as an oil: ¹H NMR (300 MHz, CDCl₃): δ 1.89 (m, 4H), 2.51 (s, 3H), 2.64-2.91 (m, 6H), 3.80 (m, 4H), 3.98-4.02 (m, 5H), 4.11 (t, J=5.9 Hz, 2H), 4.42 (m, 2H), 6.86-6.94 (m, 4H) 7.26 (m, 2H), 7.55 (d, J=2.2 Hz, 1H).

Example 15

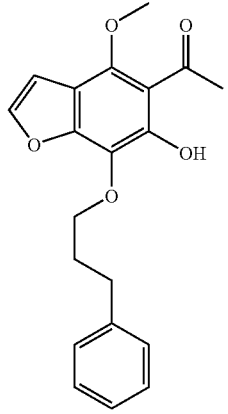

15a) 5-Acetyl-6-hydroxy-4-methoxy-7-(3-(phenyl)propoxy)benzofuran

BNC32 was prepared as described in PCT/AU2006/000333: ¹H NMR (300 MHz, CDCl₃): δ 2.14 (m, 2H), 2.36 (s, 3H), 2.91 (t, 2H), 4.09 (s, 3H), 4.35 (t, 2H), 6.11 (s, 1H), 6.99 (d, 1H), 7.00-7.31 (m, 5H), 7.60 (d, 1H). MS (ES⁺) m/z 365.3 (M+H⁺).

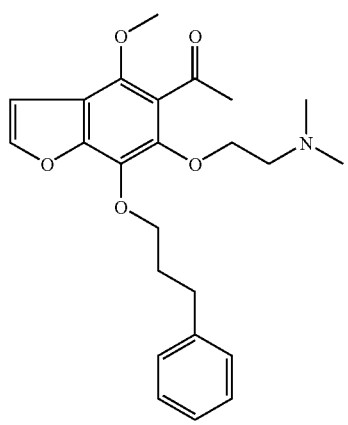

15b) 5-Acetyl-6-(2-dimethylaminoethoxy)-4-methoxy-7-(3-phenylpropoxy)benzofuran The title compound was prepared by reacting example 15a) (170 mg, 0.50 mmol), $Cs_2CO_3$ (325 mg, 1.0 mmol), KI (166 mg, 1.0 mmol) and 2-chloroethyldimethylamine hydrochloride (108 mg, 0.75 mmol) as described under General Procedure H. The crude residue was purified by flash chromatography, eluting with ethyl acetate:dichloromethane (1:1 then 1:1+5% methanol) to afford the title compound as a brown oil (40 mg, 20%). $^1$H NMR (300 MHz, $CDCl_3$): δ 2.06-2.15 (m, 2H), 2.30 (s, 6H), 2.53 (s, 3H), 2.65 (t, J=5.9 Hz, 2H), 2.85 (t, J=7.7 Hz, 2H), 3.97 (s, 3H), 4.15 (t, J=5.9 Hz, 2H), 4.28 (t, J=6.4 Hz, 2H), 6.85 (d, J=2.2 Hz, 1H), 7.15-7.30 (m, 5H), 7.54 (d, J=2.2 Hz, 1H). MS (ES$^+$) m/z 412.0 (M+H$^+$).

Example 16

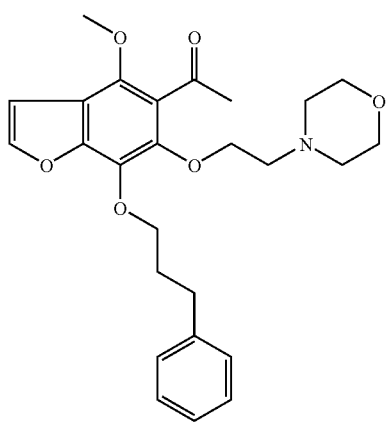

5-Acetyl-6-(2-morpholinoethoxy)-4-methoxy-7-(3-phenylpropoxy)benzofuran

The title compound was prepared by reacting example 15a) (100 mg, 0.29 mmol), $Cs_2CO_3$ (190 mg, 0.58 mmol), KI (96 mg, 0.58 mmol) and 2-chloroethylmorpholine hydrochloride (81 mg, 0.43 mmol) as described under General Procedure H. The crude residue was purified by flash chromatography, eluting with ethyl acetate:dichloromethane (1:1+2% methanol) to afford the title compound as a colourless oil (102 mg, 78%). $^1$H NMR (300 MHz, $CDCl_3$): δ 2.04-2.14 (m, 2H), 2.50 (m$_c$, 4H), 2.54 (s, 3H), 2.68 (t, J=5.7 Hz, 2H), 2.85 (t, J=7.7 Hz, 2H), 3.69 (m$_c$, 4H), 3.97 (s, 3H), 4.17 (5.7 Hz, 2H), 4.27 (t, J=6.4 Hz, 2H), 6.85 (d, J=2.2 Hz, 1H), 7.15-7.30 (m, 5H), 7.54 (d, J=2.2 Hz, 1H). MS (ES$^+$) m/z 453.9 (M+H$^+$).

Example 17

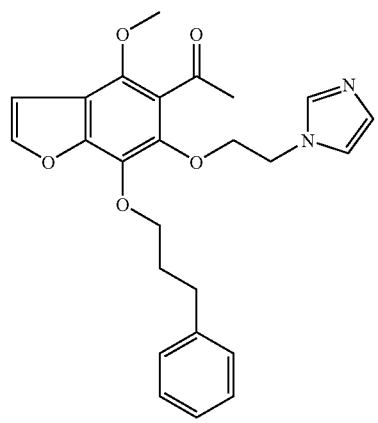

5-Acetyl-6-(2-imidazol-1-ylethoxy)-4-methoxy-7-(3-phenylpropoxy)benzofuran

Example 15a) (500 mg, 1.47 mmol, 0.6 M), $K_2CO_3$ (2 eqs) and 1,2-dibromoethane (3 eqs) were reacted according to General Procedure A. The crude residue was subjected to flash chromatography, eluting with ethyl acetate:petroleum ether (1:9) to afford the bromoalkylated material contaminated with ~10% of the 6-vinyl derivative (534 mg). A portion of this crude material (100 mg) was dissolved in anhydrous dimethylformamide (2 ml) and treated with $Cs_2CO_3$ (150 mg, 0.46 mmol) and imidazole (36 mg, 0.53 mmol). The resulting suspension was stirred under $N_2$ at 100° C. for 3 h, cooled, quenched with water (20 ml) and extracted with ethyl acetate (20 ml). The organic layer was washed with water (20 ml) and brine (10 ml), dried over $MgSO_4$ and concentrated in vacuo. The crude residue was purified by flash chromatography, eluting with ethyl acetate:dichloromethane (1:1+2% methanol) to afford the title compound as a clear oil (72 mg, 60% over two steps). $^1$H NMR (300 MHz, $CDCl_3$): δ 1.94-2.04 (m, 2H), 2.43 (s, 3H), 2.76 (t, J=7.7 Hz, 2H), 3.97 (s, 3H), 4.12 (t, J=6.4 Hz, 2H), 4.20-4.23 (m, 2H), 4.28-4.31 (m, 2H), 6.85 (d, J=2.2 Hz, 1H), 6.99 (br s, 1H), 7.05 (br s, 1H), 7.15-7.20 (m, 3H), 7.24-7.30 (m, 2H), 7.54 (br s, 1H), 7.55 (d, J=2.2 Hz, 1H). MS (ES⁺) m/z 434.9 (M+H⁺).

Example 18

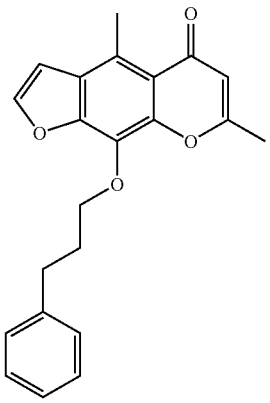

18a) 4,7-dimethyl-9-(3-(phenyl)propoxy)-5H-furo[3,2-g]chromen-5-one

The title compound was prepared by reacting 9-methoxy-7-(3-(phenyl)propoxy)-4-trifluoromethane-sulfonyl-5H-furo[3,2-g]chromen-5-one (428 mg, 1.0 mmol), ZnBr$_2$.H$_2$O (1.04 g, 4.0 mmol), CuI (28 mg, 0.15 mmol), PdCl$_2$(PPh$_3$)$_2$ (84 mg, 0.12 mmol) and MeLi (2.5 ml of 1.6 M in diethyl-ether, 4.0 mmol) as described under General Procedure G (Step 2) in 65% yield. $^1$H NMR (300 MHz, CDCl$_3$): δ 2.08-2.18 (m, 2H), 2.36 (s, 3H, Me), 2.92 (t, J=7.6, 2H, CH$_2$), 2.96 (s, 3H), 4.39 (t, J=6.3, CH$_2$), 6.05 (s, 1H), 6.92 (d, J=2.1, 1H), 7.16-7.34 (m, 5H), 7.64 (d, J=2.1, 1H). MS (ES) m/z: 348.9 (M+H⁺).

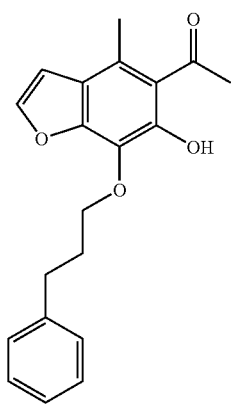

18b) 5-Acetyl-6-hydroxy-4-methyl-7-(3-(phenyl)propoxy)benzofuran

The title compound was prepared from Example 18a) as described under General Procedure G (Step 3) in 65% yield. $^1$H NMR (300 MHz, CDCl$_3$): δ 2.07-2.16 (m, 2H), 2.53 (s, 3H, CH$_3$), 2.65 (s, 3H, CH$_3$), 2.84 (t, J=7.5, 2H), 4.40 (t, J=6.3, 2H), 6.73 (d, J=2.1, 1H), 7.16-7.31 (m, 5H), 7.50 (d, J=2.1, 1H), 9.20 (s, 1H, OH). MS (ES) m/z: 324.9 (M+H⁺).

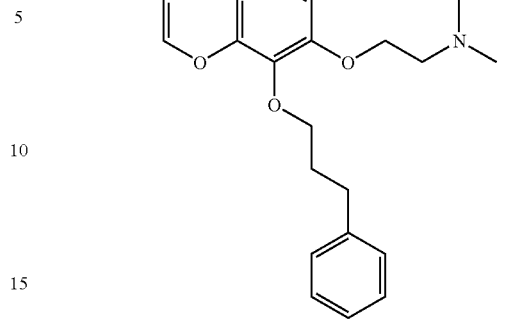

18c) 5-Acetyl-6-(2-dimethylaminoethoxy)-4-methyl-7-(3-phenylpropoxy)benzofuran

The title compound was prepared by reacting example 18b) (115 mg, 0.355 mmol), Cs$_2$CO$_3$ (300 mg, 0.92 mmol), KI (150 mg, 0.90 mmol) and 2-chloroethyldimethylamine hydrochloride (80 mg, 0.56 mmol) as described under General Procedure H The crude residue was purified by flash chromatography, eluting with ethyl acetate:dichloromethane (1:1+2% methanol then 1:1+5% methanol) to afford the title compound as a colourless oil (60 mg, 43%). $^1$H NMR (300 MHz, CDCl$_3$): δ 2.07-2.17 (m, 2H), 2.29 (s, 6H), 2.31 (s, 3H), 2.54 (s, 3H), 2.64 (t, J=5.9 Hz, 2H), 2.86 (t, J=7.7 Hz, 2H), 4.11 (t, J=6.0 Hz, 2H), 4.36 (t, J=6.4 Hz), 6.73 (d, J=2.2 Hz, 1H), 7.15-7.30 (m, 5H), 7.56 (d, J=2.2 Hz, 1H). MS (ES⁺) m/z 396.0 (M+H⁺).

Example 19

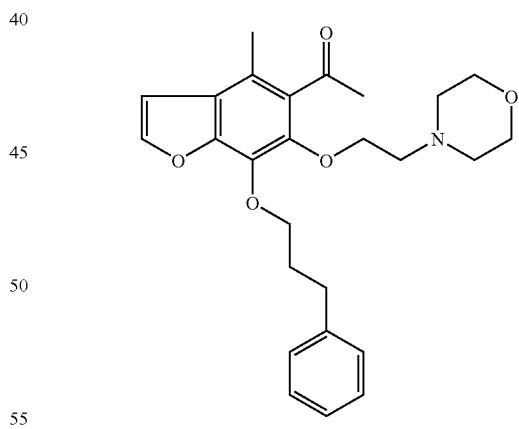

5-Acetyl-6-(2-morpholinoethoxy)-4-methyl-7-(3-phenylpropoxy)benzofuran

The title compound was prepared by reacting example 18b) (160 mg, 0.49 mmol), K$_2$CO$_3$ (170 mg, 1.23 mmol), 2-chloroethylmorpholine hydrochloride (100 mg, 0.54 mmol) and sodium iodide (10 mg) as described under General Procedure I The crude residue was purified by flash chromatography, eluting with ethyl acetate:dichloromethane (1:2) to afford the title compound as a colourless oil (180 mg, 84%). $^1$H NMR (300 MHz, CDCl₃): δ 2.06-2.16 (m, 2H), 2.31 (s, 3H), 2.48-2.51 (m, 4H), 2.56 (s, 3H), 2.67 (t, J=5.6 Hz, 2H), 2.86 (t, J=7.7 Hz, 2H), 3.68-3.71 (m, 4H), 4.12 (t, J=5.7 Hz, 2H), 4.36 (t, J=6.4 Hz, 2H), 6.73 (d, J=2.2 Hz, 1H), 7.16-7.30 (m, 5H), 7.57 (d, J=2.2 Hz, 1H). MS (ES⁺) m/z 438.0 (M+H⁺).

Example 20

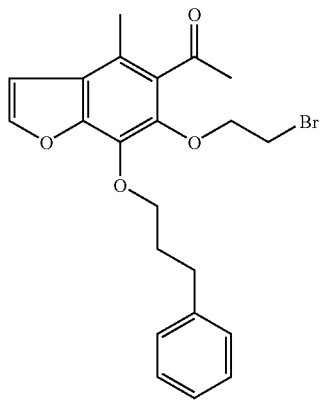

20a) 5-Acetyl-6-(2-bromoethoxy)-4-methyl-7-(3-phenylpropoxy)benzofuran

Example 18b) (150 mg, 0.46 mmol, 0.1 M), Cs₂CO₃ (2 eqs) and 1,2-dibromoethane (3 eqs) were reacted according to General Procedure A. The crude residue was subjected to flash chromatography, eluting with diethyl ether:petroleum ether (1:9) to afford the title compound as a yellow oil (140 mg, 70%). ¹H-NMR (300 MHz, CDCl₃) δ 2.08-2.17 (m, 2H), 2.31 (s, 3H), 2.55 (s, 3H), 2.86 (t, J=7.7 Hz, 2H), 3.55 (t, J=6.2 Hz, 2H), 4.32 (t, J=6.2 Hz, 2H), 4.38 (t, J=6.4 Hz, 2H), 6.74 (d, J=2.1 Hz, 1H), 7.16-7.31 (m, 5H), 7.58 (d, J=2.1 Hz, 1H). MS (ES⁺) m/z 430.8/432.8 (M+H⁺).

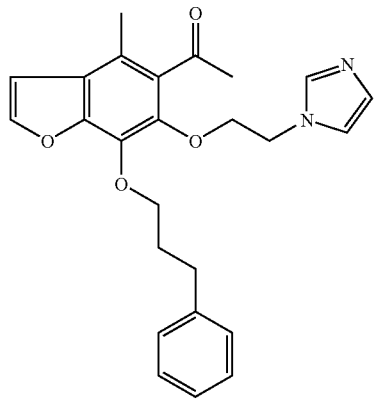

20b) 5-Acetyl-6-(2-imidazol-1-ylethoxy)-4-methyl-7-(3-phenylpropoxy)benzofuran

A suspension of Example 20a) (570 mg, 1.32 mmol), Cs₂CO₃ (860 mg, 2.64 mmol) and imidazole (180 mg, 2.64 mmol) in anhydrous dimethylformamide (8 ml) was stirred under N₂ at 70° C. for 16 h. After this time the reaction was cooled, quenched with water (30 ml) and extracted with ethyl acetate (30 ml). The organic layer was washed with water (2×30 ml) and brine (20 ml), dried over MgSO₄ and concentrated in vacuo. The crude residue was purified by flash chromatography, eluting with ethyl acetate:dichloromethane (1:1 then 1:1+3% methanol) to afford the title compound as a colourless oil (375 mg, 68%). ¹H NMR (300 MHz, CDCl₃): δ 1.98-2.08 (m, 2H), 2.29 (s, 3H), 2.36 (s, 3H), 2.78 (t, J=7.7 Hz, 2H), 4.19-4.28 (m, 6H), 6.73 (d, J=2.1 Hz, 1H), 6.99 (br s, 1H), 7.07 (br s, 1H), 7.16-7.20 (m, 3H), 7.24-7.30 (m, 2H), 7.54 (br s, 1H), 7.58 (d, J=2.2 Hz, 1H). MS (ES⁺) m/z 418.9 (M+H⁺).

Example 21

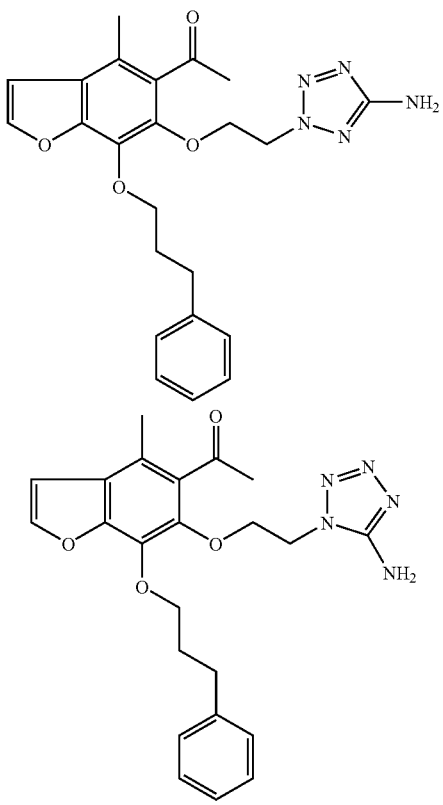

21a) 5-Acetyl-6-[2-(5-aminotetrazol-2-yl)ethoxy]-4-methyl-7-(3-phenylpropoxy)benzofuran 21b) 5-Acetyl-6-[2-(5-aminotetrazol-1-yl)ethoxy]-4-methyl-7-(3-phenylpropoxy)benzofuran A suspension of the bromide of Example 20a) (70 mg, 0.16 mmol), Cs₂CO₃ (106 mg, 0.32 mmol) and 5-aminotetrazole (28 mg, 0.32 mmol) in anhydrous dimethylformamide (1.5 ml) was stirred under N₂ at 90° C. for 16 h. After this time the reaction was cooled, quenched with 1M HCl (20 ml) and extracted with ethyl acetate (20 ml). The organic layer was washed with water (20 ml) and brine (10 ml), dried over MgSO₄ and concentrated in vacuo. The crude residue was purified by flash chromatography, eluting with ethyl acetate:dichloromethane (1:2) to afford the title compound 21 a) as a colourless oil (26 mg, 37%). ¹H NMR (300 MHz, CDCl₃): δ

2.02-2.12 (m, 2H), 2.28 (s, 3H), 2.37 (s, 3H), 2.82 (t, J=7.7 Hz, 2H), 4.26 (br s, 2H), 4.31 (t, J=6.4 Hz, 2H), 4.48 (t, J=5.3 Hz, 2H), 4.70 (t, J=5.2 Hz, 2H), 6.72 (d, J=2.2 Hz, 1H), 7.16-7.31 (m, 5H), 7.57 (d, J=2.2 Hz, 1H). MS (ES$^+$) m/z 435.9 (M+H$^+$).

Further elution with ethyl acetate:dichloromethane (1:1, 2:1, 1:0) afforded the title compound 21b) as a resin that slowly crystallised (24 mg, 34%). $^1$H NMR (300 MHz, CDCl$_3$): δ 1.96-2.05 (m, 2H), 2.30 (s, 3H), 2.40 (s, 3H), 2.74 (t, J=7.7 Hz, 2H), 4.31 (t, J=6.6 Hz, 2H), 4.38-4.44 (m, 4H), 5.14 (br s, 2H), 6.72 (d, J=2.1 Hz, 1H), 7.14-7.19 (m, 3H), 7.24-7.29 (m, 2H), 7.57 (d, J=2.1 Hz, 1H). MS (ES$^+$) m/z 435.9 (M+H$^+$).

Example 22

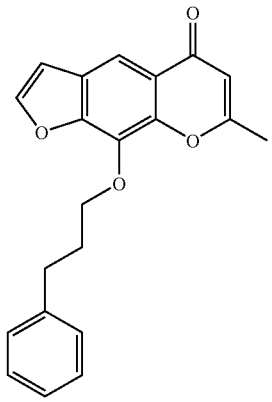

22a) 7-Methyl-9-(3-(phenyl)propoxy)-5H-furo[3,2-g]chromen-5-one 9-(3-Phenylpropoxy)-7-methyl-4-trifluoromethanesulfonyl-5H-furo[3,2-g]chromen-5-one (1.5 g, 3.11 mmol, 0.2M, prepared from the corresponding 4-hydroxy system according to General Procedure G, Step 1) was dissolved in anhydrous dimethylformamide and treated with triethylammonium formate (1.8 g, 12.4 mmol.). The reaction flask was evacuated and back-filled with N$_2$ three times. Anhydrous triethylamine (0.63 g, 6.20 mmol), Pd(OAc)$_2$ (70 mg, 0.31 mmol) and triphenylphosphine (0.16 mg, 0.62 mmol) were added to the reaction mixture and the flask was again evacuated and back-filled with N$_2$. The reaction mixture was heated to 60-70° C. for 24 hours under a N$_2$ atmosphere. The solvents were removed under vacuum and the residue was dissolved in ethyl acetate and washed with saturated aqueous NH$_4$Cl solution. The organic layer was dried over MgSO$_4$, concentrated under vacuum and the crude residue was purified by silica gel chromatography, eluting with diethyl ether:dichloromethane (0:1, then 1:3) to afford the title compound as a pale yellow solid (75%). $^1$H NMR (300 MHz, CDCl$_3$) δ: 2.06-2.16 (m, 2H), 2.41 (s, 3H, CH$_3$), 2.92 (t, J=7.5 Hz, 2H), 4.49 (t, J=6.6 Hz, 2H), 6.15 (s, 1H), 6.85 (d, J=2.1 Hz, 1H), 7.16-7.30 (m, 5H), 7.69 (d, J=2.1 Hz, 1H), 8.09 (s, 1H). MS (ES$^+$) m/z: 335 (M+H$^+$).

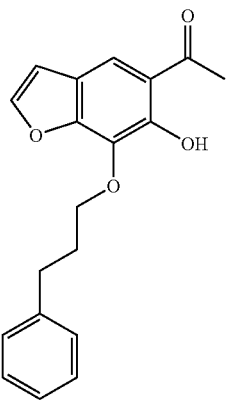

22b) 5-Acetyl-6-hydroxy-7-(3-(phenyl)propoxy)benzofuran

Example 22a) (760 mg, 2.27 mmol) was reacted according to General Procedure B to afford the title compound as a pale yellow oil (68 mg, 10%). $^1$H NMR (300 MHz, CDCl$_3$) δ: 2.06-2.16 (m, 2H), 2.68 (s, 3H, CH$_3$), 2.88 (t, J=7.5 Hz, 2H), 4.35 (t, J=6.6 Hz, 2H), 6.71 (d, J=2.1 Hz, 1H), 7.13-7.29 (m, 5H), 7.55 (d, J=2.1 Hz, 1H), 7.72 (s, 1H), 12.30 (bs, 1H, OH). MS (ES$^+$) m/z: 311 (M+H$^+$).

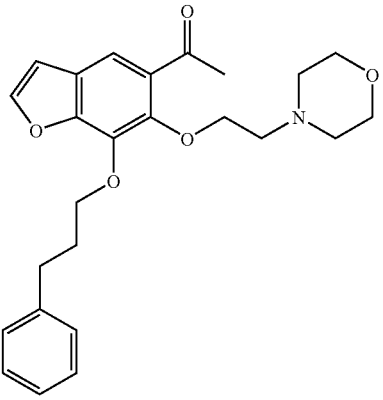

22c) 5-Acetyl-6-(2-morpholin-4-yl-ethoxy)-7-(3-phenylpropoxy)benzofuran

The title compound was prepared by reacting example 22b) (60 mg, 0.19 mmol) and K$_2$CO$_3$ (58 mg, 0.42 mmol), 4-(2-chloroethyl)morpholine hydrochloride (45 mg, 0.24 mmol) as described under General Procedure H. The crude residue was purified by silica-gel flash chromatography, eluting with dichloromethane:ethyl acetate (2:1 then 1:1) to provide the title compound as a colourless oil (57 mg, 71%). $^1$H-NMR δ 2.08-2.18 (m, 2H), 2.48-2.51 (m, 4H), 2.69 (s, 3H), 2.71 (t, J=5.6 Hz, 2H), 2.87 (t, J=7.4 Hz, 2H), 3.66-3.69 (m, 4H), 4.22

(t, J=5.6 Hz, 2H), 4.40 (t, J=6.3 Hz, 2H), 6.74 (d, J=2.1 Hz, 1H), 7.16-7.31 (m, 5H), 7.53 (s, 1H), 7.58 (d, J=2.1 Hz, 1H). MS (ES+) m/z: 424 (M+H).

Example 23

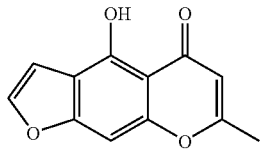

23a) 4-Hydroxy-7-methyl-furo[3,2-g]chromen-5-one

To a suspension of visnagin (920 mg, 4.0 mmol) in dichloromethane (20 mL) at −78° C. was added a solution of boron trichloride (1.0 M, 4.0 mL, 4.0 mmol) and the reaction mixture was stirred at −78° C. for 15 min then rt for 16 h. The reaction mixture was cooled to 0° C. and water (25 mL) was added slowly at first. The organics were concentrated in vacuo and the resulting suspension was diluted with 5% citric acid (150 mL) and heated at 60° C. for 1 h. The suspension was filtered, washing with water (3×50 mL) and the resulting solid was dried in a vacuum oven to afford the title compound as a yellow solid (710 mg, 83%): $^1$H NMR (300 MHz, CDCl$_3$): δ 2.38 (s, 3H), 6.06 (s, 1H), 6.97 (d, J=2.2 Hz, 1H), 6.99 (s, 1H), 7.55 (d, J=2.2 Hz, 1H), 13.52 (s, 1H). MS (ES+) m/z 217.2 (M+H+).

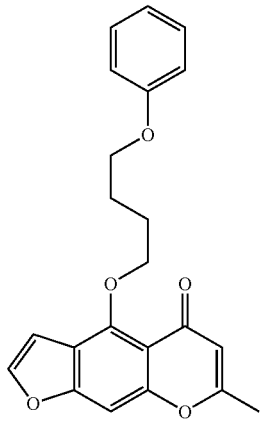

23b) 4-(4-(phenoxy)butoxy)-7-methyl-furo[3,2-g]chromen-5-one

Example 23a) (43 mg, 0.20 mmol) and 4-(phenoxy)butylbromide (55 mg, 0.24 mmol) were treated as described under General Procedure A. The crude product was purified by flash chromatography eluting with ethyl acetate/petroleum ether (1:4) to afford the title compound (51 mg, 70%) as a colourless solid: $^1$H NMR (300 MHz, CDCl$_3$): δ 2.06 (m, 4H), 2.32 (s, 3H), 4.06 (t, J=5.7 Hz, 2H), 4.33 (t, J=5.7 Hz, 2H), 6.04 (s, 1H), 6.86-6.96 (m, 4H), 7.22-7.27 (m, 3H), 7.57 (d, J=2.3 Hz, 1H). MS (ES+) m/z 365.2 (M+H+).

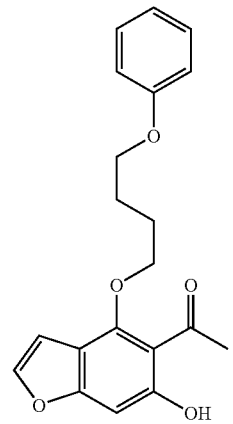

23c) 5-Acetyl-4-(4-(phenoxy)butoxy)-6-hydroxybenzofuran

Example 23b) (36 mg, 0.10 mmol) was treated as described under General Procedure B to afford the title compound (30 mg, 88%) as a brown solid: $^1$H NMR (300 MHz, CDCl$_3$): δ 1.96-2.15 (m, 4H), 2.73 (s, 3H), 4.05 (t, J=5.7 Hz, 2H), 4.51 (t, J=6.3 Hz, 2H), 6.69 (s, 1H), 6.84-6.97 (m, 4H), 7.24-7.30 (m, 2H), 7.40 (d, J=2.4 Hz, 1H). MS (ES+) m/z 341.0 (M+H+).

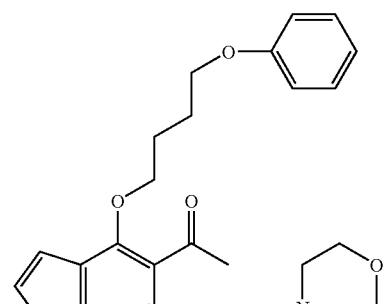

23d) 5-Acetyl-6-(2-morpholin-4-yl-ethoxy)-4-(4-phenoxybutoxy)benzofuran

The title compound was prepared by reacting example 23c) (51 mg, 0.15 mmol), K$_2$CO$_3$ (41 mg, 0.30 mol) and NaI (8 mg, 0.05 mmol,) and 4-(2-chloroethyl)morpholine hydrochloride (33 mg, 0.18 mmol) as described under General Procedure I. The crude residue was purified by silica-gel flash chromatography, eluting with dichloromethane:ethyl acetate (7:3, then 7:3+1% methanol) to afford the title compound as a colourless oil (46 mg, 68%). ¹H-NMR (CDCl₃) δ 1.91-1.96 (m, 4H), 2.50 (s, 3H), 2.60-2.75 (br m, 4H), 2.80-2.95 (br m, 2H), 3.70-3.85 (br m, 4H), 3.99-4.02 (m, 2H), 4.15-4.30 (br m, 2H), 4.39-4.33 (m, 2H), 6.75 (d, J=0.8 Hz, 1H), 6.79 (dd, J=2.3, 0.9 Hz, 1H), 6.86-6.95 (m, 3H), 7.22-7.29 (m, 2H), 7.48 (d, J=2.3 Hz, 1H). MS (ES⁺) m/z: 454 (M+H).

Example 24

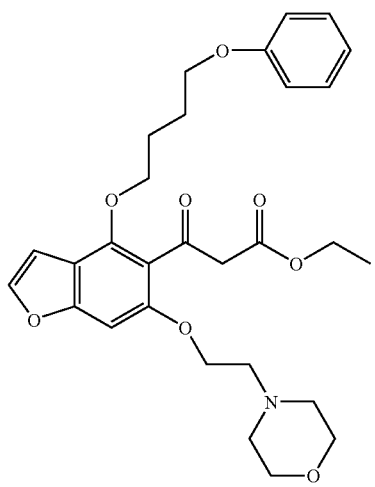

3-[6-(2-Morpholin-4-ylethoxy)-4-(4-phenoxybutoxy)benzofuran-5-yl]-3-oxo-propionic acid ethyl ester A suspension of finely cut sodium (21 mg, 0.91 mmol) and Example 23d) (40 mg, 0.09 mmol) in diethyl carbonate (0.65 ml) was heated to 90° C. for 1.5 h then left at 70° C. overnight. After this time the reaction was cooled, quenched with ethanol (1 ml) and partitioned over water and dichloromethane. The aqueous phase was acidified to pH 4 with 10% citric acid and then to pH8 with saturated NaHCO₃. The aqueous phase was extracted with dichloromethane (2×) and the combined organic layers were dried over NaS₂O₄ and concentrated in vacuo. The crude residue was purified by silica-gel flash chromatography, eluting with dichloromethane:ethyl acetate (1:1, then 1:1+1% methanol) to give the title compound as an oil (15 mg, 33%). ¹H-NMR (CDCl₃) δ 1.20 (t, J=7.1 Hz, 3H), 1.94-1.98 (m, 4H), 2.57 (br m, 4H), 2.80 (br t, 2H), 3.70-3.72 (m, 4H), 3.90 (s, 2H), 3.99-4.03 (m, 2H), 4.10-4.15 (m, 2H), 4.14 (q, J=7.1 Hz, 2H), 4.30-4.34 (m, 2H), 6.74 (d, J=0.8 Hz, 1H), 6.79 (dd, J=2.3, 0.9 Hz, 1H), 6.86-6.94 (m, 3H), 7.22-7.28 (m, 2H), 7.47 (d, J=2.3 Hz, 1H). MS (ES⁺) m/z: 526 (M+H).

Example 25

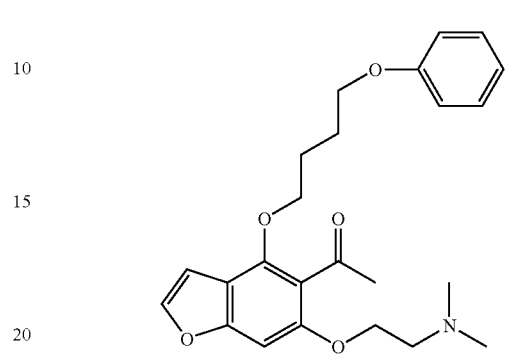

5-Acetyl-6-(2-dimethylamino-ethoxy)-4-(4-phenoxybutoxy)benzofuran

The title compound was prepared by reacting example 23c) (34 mg, 0.10 mmol), K₂CO₃ (31 mg, 0.22 mol), NaI (5 mg, 0.03 mmol) and 2-(dimethylamino)ethylchloride hydrochloride (34 mg, 0.24 mmol) as described under General Procedure I. The crude residue was purified by silica-gel flash chromatography, eluting with dichloromethane then dichloromethane:methanol (19:5) to afford the title compound as a colourless oil (13 mg, 32%). ¹H-NMR (CDCl₃) δ 1.92-1.96 (m, 4H), 2.45 (s, 6H), 2.49 (s, 3H), 2.88-2.91 (m, 2H), 3.99-4.02 (m, 2H), 4.20 (t, J=5.6 Hz, 2H), 4.29-4.32 (m, 2H), 6.76 (d, J=0.7 Hz, 1H), 6.79 (dd, J=2.3, 0.9 Hz, 1H), 6.86-6.94 (m, 3H), 7.22-7.28 (m, 2H), 7.47 (d, J=2.3 Hz, 1H). MS (ES⁺) m/z: 412 (M+H).

Example 26

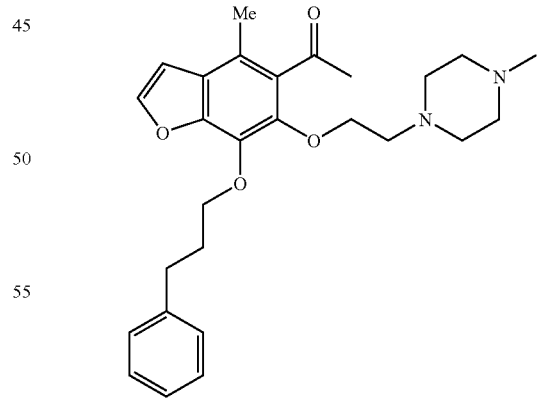

5-Acetyl-6-(2-methyl-piperazin-1-yl)-4-methyl-7-(3-phenylpropoxy)-benzofuran

Example 20a) (100 mg, 0.23 mmol) and N-methylpiperazine (3 eqs.) were reacted according to General Procedure E. The crude product was purified by silica-gel flash chromatography, eluting with methanol:dichloromethane:ethyl acetate (8:46:46) to afford the title compound as a clear oil (78 mg, 75%). $^1$H NMR (300 MHz, CDCl$_3$): δ 2.06-2.17 (m, 2H), 2.26 (s, 3H, Me), 2.31 (s, 3H, Me), 2.40-2.55 (bm+s, 11H), 2.68 (t, J=5.7 Hz, 2H, CH$_2$), 2.86 (t, J=7.5 Hz, 2H, CH$_2$), 4.12 (t, J=5.7 Hz, 2H, CH$_2$), 4.36 (t, J=6.3 Hz, CH$_2$), 6.72 (d, J=2.1 Hz, 1H), 7.16-7.30 (m, 5H), 7.56 (d, J=2.1 Hz, 1H). MS (ES+) m/z: 451 (M+H$^+$).

Example 27

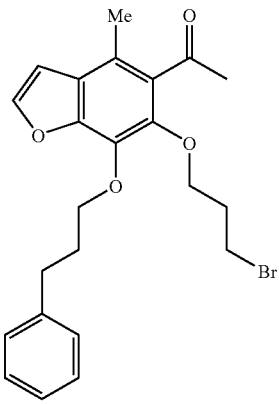

27a) 5-Acetyl-6-(4-bromopropoxy)-4-methyl-7-(3-phenylpropoxy)-benzofuran

Example 18b) (300 mg, 0.93 mmol, 0.8 M), Cs$_2$CO$_3$ (2.0 eqs) and 1,3-dibromopropane (4 eqs) were reacted according to General Procedure A. The crude product was purified by flash chromatography, eluting with petroleum ether:dichloromethane (1:1) to afford the title compound as a clear oil (322 mg, 78%). $^1$H NMR (300 MHz, CDCl$_3$): δ 2.08-2.15 (m, 2H), 2.21 (quintet, J=6.3 Hz, 2H), 2.31 (s, 3H, Me), 2.51 (s, 3H, Me), 2.86 (t, J=7.5 Hz, 2H, CH$_2$), 3.55 (t, J=6.6 Hz, 2H), 4.15 (t, J=6.0 Hz, 2H), 4.36 (t, J=6.3 Hz, CH$_2$), 6.73 (d, J=2.1 Hz, 1H), 7.16-7.32 (m, 5H), 7.57 (d, J=2.1 Hz, 1H).

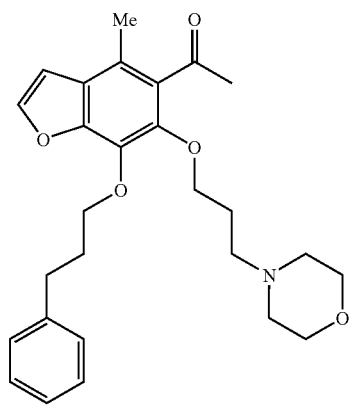

27b) 5-Acetyl-6-(3-morpholin-4-yl-propoxy)-4-methyl-7-(3-phenylpropoxy)-benzofuran Example 27a) (150 mg, 0.34 mmol) and morpholine (3 eqs.) were reacted according to General Procedure E. The crude product was purified by flash chromatography, eluting with methanol:dichloromethane:ethyl acetate (2:49:49) to afford the title compound as a clear oil (131 mg, 86%). $^1$H NMR (300 MHz, CDCl$_3$): δ 1.89 (quintet, J=6.3 Hz, 2H), 2.06-2.15 (m, 2H), 2.31 (s, 3H, Me), 2.40-2.49 (m, 6H), 2.52 (s, 3H, Me), 2.86 (t, J=7.5 Hz, 2H, CH$_2$), 3.68 (t, J=4.5 Hz, 2H), 4.07 (t, J=6.0 Hz, 2H), 4.35 (t, J=6.3 Hz, CH$_2$), 6.72 (d, J=2.1 Hz, 1H), 7.15-7.30 (m, 5H), 7.56 (d, J=2.1 Hz, 1H). MS (ES$^+$) m/z: 452 (M+H$^+$).

Example 28

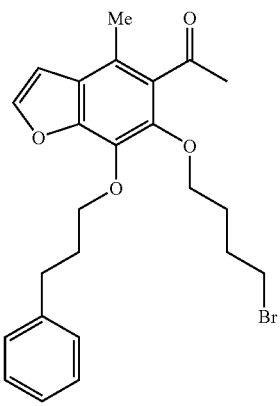

28a) 5-Acetyl-6-(4-bromobutoxy)-4-methyl-7-(3-phenylpropoxy)-benzofuran

Example 18b) (324 mg, 1.00 mmol, 0.8 M), Cs$_2$CO$_3$ (2.0 eqs) and 1,3-dibromobutane (4 eqs) were reacted according to General Procedure A. The crude product was purified by flash chromatography, eluting with petroleum ether:dichloromethane (1:1) to afford the title compound as a clear oil (344 mg, 75%). $^1$H NMR (300 MHz, CDCl$_3$): δ 1.80-1.89 (m, 2H), 1.97-2.16 (m, 4H), 2.31 (s, 3H, Me), 2.51 (s, 3H, Me), 2.86 (t, J=7.5 Hz, 2H, CH$_2$), 3.45 (t, J=6.6 Hz, 2H), 4.03 (t, J=6.0 Hz, 2H), 4.35 (t, J=6.3 Hz, CH$_2$), 6.72 (d, J=2.1 Hz, 1H), 7.16-7.31 (m, 5H), 7.56 (d, J=2.1 Hz, 1H).

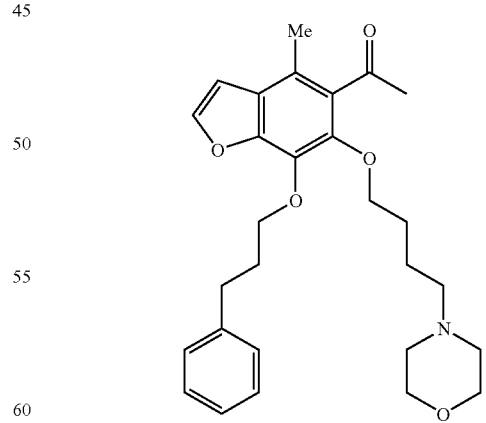

28b) 5-Acetyl-6-(4-morpholin-4-yl-butoxy)-4-methyl-7-(3-phenylpropoxy)-benzofuran Example 28a) (160 mg, 0.35 mmol) and morpholine (3 eqs.) were reacted according to General Procedure E. The crude product was purified by flash chromatography, eluting with methanol:dichloromethane:ethyl acetate (2:49:49) to afford the title compound as a clear oil (95 mg, 58%). $^1$H NMR (300 MHz, CDCl$_3$): δ 1.55-1.64 (m, 2H), 1.69-1.78 (m, 2H), 2.05-2.15 (m, 2H), 2.31 (s, 3H, Me), 2.32-2.38 (m, 6H), 2.52 (s, 3H, Me), 2.86 (t, J=7.5 Hz, 2H, CH$_2$), 3.67 (t, J=4.5 Hz, 2H), 4.02 (t, J=6.6 Hz, 2H), 4.34 (t, J=6.3 Hz, CH$_2$), 6.72 (d, J=2.1 Hz, 1H), 7.15-7.30 (m, 5H), 7.56 (d, J=2.1 Hz, 1H). MS (ES$^+$) m/z: 466 (M+H$^+$).

Example 29

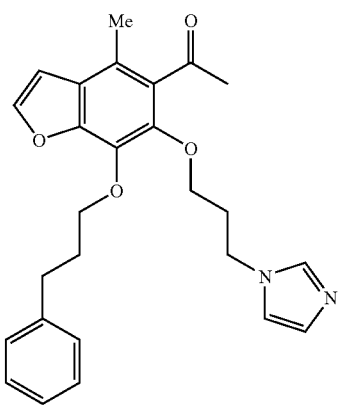

5-Acetyl-6-(3-imidazol-1-yl-propoxy)-4-methyl-7-(3-phenylpropoxy)-benzofuran

Example 27a) (100 mg, 0.22 mmol) and imidazole (4 eqs) were reacted according to General Procedure E. The crude product was purified by flash chromatography, eluting with methanol:dichloromethane:ethyl acetate (4:48:48) to afford the title compound as a clear oil (73 mg, 75%). $^1$H NMR (300 MHz, CDCl$_3$): δ 2.04-2.16 (m, 4H), 2.31 (s, 3H, Me), 2.52 (s, 3H, Me), 2.83 (t, J=7.5 Hz, 2H, CH$_2$), 4.04 (t, J=6.3 Hz, 2H), 4.09 (t, J=6.6 Hz, 2H), 4.36 (t, J=6.3 Hz, CH$_2$), 6.73 (d, J=2.1 Hz, 1H), 6.93 (bs, 1H), 7.03 (bs, 1H), 7.18-7.29 (m, 5H), 7.57 (bs, 1H), 7.58 (d, J=2.1 Hz, 1H). MS (ES$^+$) m/z: 433 (M+H$^+$).

Example 30

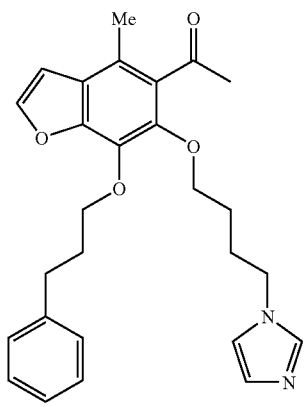

5-Acetyl-6-(4-imidazol-1-yl-butoxy)-4-methyl-7-(3-phenylpropoxy)-benzofuran

Example 28a) (100 mg, 0.22 mmol) and imidazole (4 eqs) were reacted according to General Procedure E. The crude product was purified by flash chromatography, eluting with methanol:dichloromethane:ethyl acetate (4:48:48) to afford the title compound as a clear oil (73 mg, 75%). $^1$H NMR (300 MHz, CDCl$_3$): δ 1.62-1.71 (m, 2H), 1.86-1.96 (m, 2H), 2.04-2.13 (m, 2H), 2.30 (s, 3H, Me), 2.49 (s, 3H, Me), 2.84 (t, J=7.5 Hz, 2H, CH$_2$), 3.95 (t, J=6.3 Hz, 2H), 4.01 (t, J=6.6 Hz, 2H), 4.34 (t, J=6.3 Hz, CH$_2$), 6.72 (d, J=2.1 Hz, 1H), 6.91 (bs, 1H), 7.04 (bs, 1H), 7.15-7.30 (m, 5H), 7.46 (bs, 1H), 7.56 (d, J=2.1 Hz, 1H). MS (ES$^+$) m/z: 447 (M+H$^+$).

Example 31

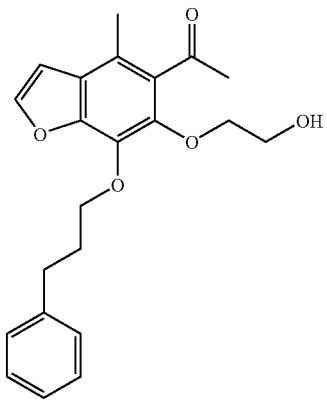

31a) 1-[6-(2-Hydroxy-ethoxy)-4-methyl-7-(3-phenyl-propoxy)-benzofuran-5-yl]-ethanone Example 31a) was prepared from example 18b) and 2-bromoethanol (2 eq.) as described in General Procedure A in 76% yield. $^1$H NMR (300 MHz, CDCl$_3$): δ 2.08-2.17 (m, 2H), 2.32 (s, 3H), 2.55 (s, 3H), 2.83-2.88 (m, 3H), 3.74-3.78 (m, 2H), 4.15-4.17 (m, 2H), 4.39 (t, J=6.4 Hz, 2H), 6.74 (d, J=2.1 Hz, 1H), 7.15-7.30 (m, 5H), 7.58 (d, J=2.1 Hz, 1H) MS (ES$^+$) m/z 369.0 (M+H$^+$).

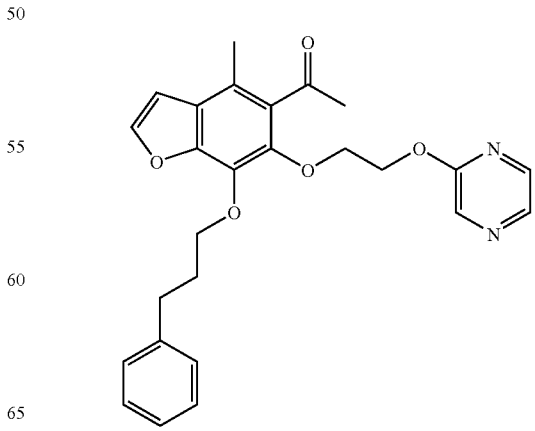

31b) 1-{4-Methyl-7-(3-phenyl-propoxy)-6-[2-(pyrazin-2-yloxy)-ethoxy]-benzofuran-5-yl}-ethanone To a solution of Example 31a) (120 mg, 0.326 mmol) in dry DMF (2.5 ml) was added sodium hydride (14 mg, 0.359 mmol, 60% dispersion in mineral oil) and the dark reaction mixture was allowed to stir at rt for 30 minutes. After this time chloropyrazine (34 ul, 0.39 mmol) was added and the reaction heated to 80-90° C. overnight then cooled to room temperature, quenched with water (20 ml) and extracted with EtOAc (20 ml). The organic layer was washed with water (2×20 ml) and brine (20 ml), dried over $MgSO_4$ and concentrated under vacuum. The crude residue was purified by silica-gel flash chromatography (eluent=4:1 hexanes:EtOAc) to provide the product as a clear oil (65 mg, 45%). $^1$H NMR (300 MHz, $CDCl_3$): δ 2.05-2.14 (m, 2H), 2.31 (s, 3H), 2.53 (s, 3H), 2.85 (t, J=7.4 Hz, 2H), 4.35-4.41 (m, 4H), 4.56-4.59 (m, 2H), 6.74 (d, J=2.2 Hz, 1H), 7.15-7.30 (m, 5H), 7.58 (d, J=2.2 Hz, 1H), 8.04 (br s, 1H), 8.10 (br s, 1H), 8.24 (s, 1H), MS (ES$^+$) m/z 446.9 (M+H$^+$).

Example 32

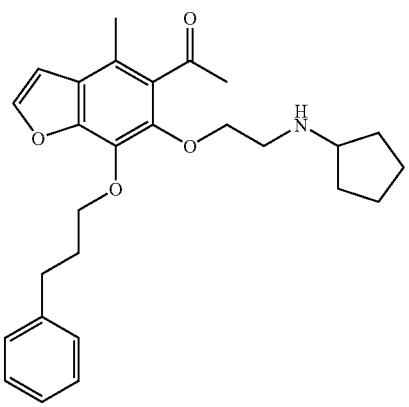

1-[6-(2-Cyclopentylamino-ethoxy)-4-methyl-7-(3-phenyl-propoxy)-benzofuran-5-yl]-ethanone Example 20a) and cyclopentylamine were reacted according to General Procedure E to afford Example 32 in 87% yield. $^1$H NMR (300 MHz, $CDCl_3$): δ 1.29-1.37 (m, 2H), 1.45-1.70 (m, 5H), 1.77-1.85 (m, 2H), 2.07-2.16 (m, 2H), 2.31 (s, 3H), 2.53 (s, 3H), 2.82-2.88 (m, 4H), 3.09 (quintet, J=6.6 Hz, 1H), 4.14 (t, J=5.2 Hz, 2H), 4.35 (t, J=6.4 Hz, 2H), 6.72 (d, J=1.5 Hz, 1H), 7.17-7.30 (m, 5H), 7.56 (d, J=1.5 Hz, 1H) MS (ES$^+$) m/z 436.0 (M+H$^+$).

Example 33

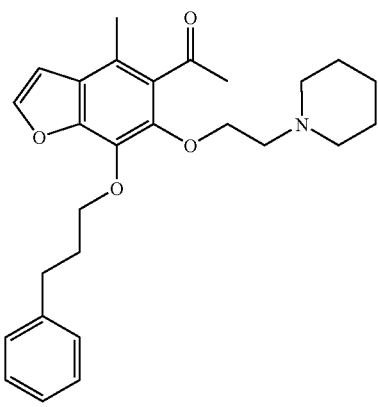

1-[4-Methyl-7-(3-phenyl-propoxy)-6-(2-piperidin-1-yl-ethoxy)-benzofuran-5-yl]-ethanone Example 20a) and piperidine were reacted according to General Procedure E to afford Example 33 in 74% yield. $^1$H NMR (300 MHz, $CDCl_3$): δ 1.40-1.44 (m, 2H), 1.55 (br m, 4H), 2.07-2.16 (m, 2H), 2.31 (s, 3H), 2.43 (br m, 4H), 2.55 (s, 3H), 2.66 (t, J=5.9 Hz, 2H), 2.86 (t, J=7.3 Hz, 2H), 4.13 (t, J=6.0 Hz, 2H), 4.35 (t, J=6.4 Hz, 2H), 6.72 (d, J=2.1 Hz, 1H), 7.17-7.30 (m, 5H), 7.56 (d, J=2.1 Hz, 1H), MS (ES$^+$) m/z 436.0 (M+H$^+$).

Example 34

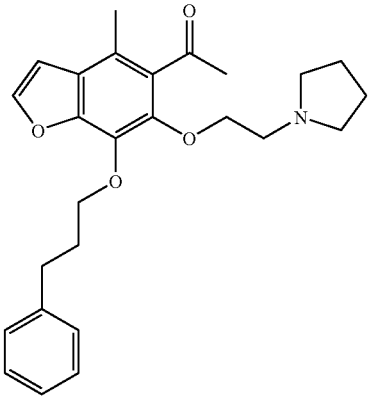

1-[4-Methyl-7-(3-phenyl-propoxy)-6-(2-pyrrolidin-1-yl-ethoxy)-benzofuran-5-yl]-ethanone Example 20a) and pyrrolidine were reacted according to General Procedure E to afford Example 34 in 67% yield.

$^1$H NMR (300 MHz, $CDCl_3$): δ 1.77 (br m, 4H), 2.07-2.16 (m, 2H), 2.31 (s, 3H), 2.54 (s, 3H), 2.56 (br m, 4H), 2.79-2.88

(m, 4H), 4.14 (t, J=6.1 Hz, 2H), 4.36 (t, J=6.4 Hz, 2H), 6.73 (d, J=2.1 Hz, 1H), 7.15-7.30 (m, 5H), 7.56 (d, J=2.1 Hz, 1H), MS (ES+) m/z 422.0 (M+H+).

Examples 35 and 36

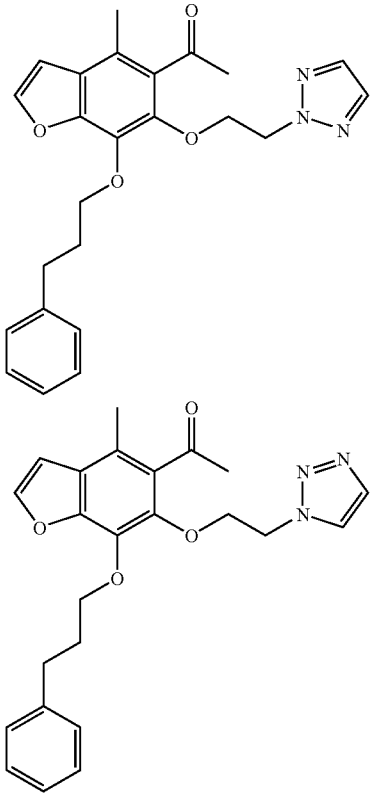

Example 35

1-[4-Methyl-7-(3-phenyl-propoxy)-6-(2-[1,2,3]tria-zol-2-yl-ethoxy)-benzofuran-5-yl]ethanone Example 36

1-[4-Methyl-7-(3-phenyl-propoxy)-6-(2-[1,2,3]tria-zol-1-yl-ethoxy)-benzofuran-5-yl]-ethanone To a suspension of Example 20a) (80 mg, 0.186 mmol) and Cs$_2$CO$_3$ (2 eq.) in dry DMF (1.5 ml) was added 1,2,3-triazole (2.5 eq.) and the reaction was stirred at 90° C. overnight. After cooling the reaction was quenched with water (20 ml) and extracted with EtOAc (20 ml). The organic layer was washed with water (2×20 ml) and brine (20 ml), dried over MgSO$_4$ and concentrated under vacuum. The crude residue was subjected to silica-gel flash chromatography (eluent=DCM then 19:1 DCM:EtOAc to give Example 35 as a clear oil (38 mg, 49%). $^1$H NMR (300 MHz, CDCl$_3$): δ 2.03-2.15 (m, 2H), 2.30 (s, 3H), 2.37 (s, 3H), 2.83 (t, J=7.2 Hz, 2H), 4.30 (t, J=6.4 Hz, 2H), 4.53-4.57 (m, 2H), 4.77-4.80 (m, 2H), 6.74 (d, J=2.2 Hz, 1H), 7.18-7.33 (m, 5H), 7.59 (d, J=2.2 Hz, 1H), 7.63 (s, 2H), MS (ES+) m/z 419.9 (M+H+).

Further elution (eluent=4:1 DCM:EtOAc) provided Example 36 as a clear oil (33 mg, 42%). $^1$H NMR (300 MHz, CDCl$_3$): δ 2.00-2.09 (m, 2H), 2.32 (s, 3H), 2.37 (s, 3H), 2.80 (t, J=7.3 Hz, 2H), 4.30 (t, J=6.5 Hz, 2H), 4.44-4.47 (m, 2H), 4.69-4.72 (m, 2H), 6.75 (d, J=2.2 Hz, 1H), 7.16-7.33 (m, 5H), 7.60 (d, J=2.2 Hz, 1H), 7.72 (s, 1H), 7.74 (s, 1H). MS (ES+) m/z 419.9 (M+H+).

Example 37

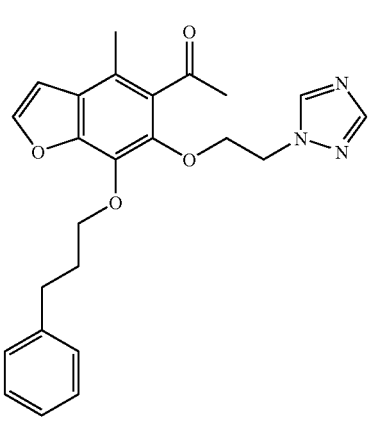

1-[4-Methyl-7-(3-phenyl-propoxy)-6-(2-[1,2,4]tria-zol-1-yl-ethoxy)-benzofuran-5-yl]-ethanone Example 37 was prepared in the same manner as described for Example 36 but from 1,2,4-triazole in 84% yield. $^1$H NMR (300 MHz, CDCl$_3$): δ 2.02-2.11 (m, 2H), 2.32 (s, 3H), 2.38 (s, 3H), 2.81 (t, J=7.4 Hz, 2H), 4.30 (t, J=6.5 Hz, 2H), 4.41-4.47 (m, 4H), 6.75 (d, J=2.2 Hz, 1H), 7.18-7.33 (m, 5H), 7.60 (d, J=2.2 Hz, 1H), 7.96 (s, 1H), 8.21 (s, 1H). MS (ES+) m/z 419.9 (M+H+).

Example 38

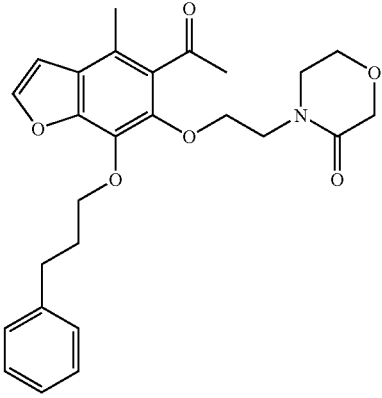

4-{2-[5-Acetyl-4-methyl-7-(3-phenyl-propoxy)-ben-zofuran-6-yloxy]-ethyl}-morpholin-3-one A solution of Example 20 (55 mg, 0.17 mmol) in MeCN (1.0 mL) was added to CsCO$_3$ (110 mg, 0.34 mmol), tetrabutylammonium bromide (3 mg, 0.009 mmol) and morpholin-3-one (17 mg, 0.17 mmol) and the reaction mixture was stirred at 60° C. for 48 h, then diluted with DCM and filtered, washing with DCM. The solvent was concentrated under vacuum. The crude product was subjected to silica-gel flash chromatography (petroleum ether/ethyl acetate, 9:1, 7:3) to give Example 38 (4 mg, 5%). $^1$H NMR (300 MHz, CDCl$_3$): δ 2.01-2.15 (m, 2H), 2.30 (s, 3H), 2.49 (s, 3H), 2.81-2.87 (m, 2H), 3.48 (t, J=5.3 Hz, 2H), 3.72 (t, J=5.3 Hz, 2H), 3.87-3.89 (m, 2H), 4.41-4.17 (m, 2H), 4.22 (t, J=5.0 Hz, 2H), 4.33-4.41 (m, 2H), 6.72 (d, J=2.2 Hz, 1H), 7.15-7.35 (m, 5H), 7.57 (d, J=2.2 Hz, 1H). MS (ES$^+$) m/z 452.2 (M+H$^+$).

Example 39

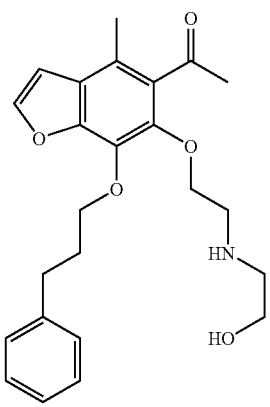

5-Acetyl-6-(2-(2-Hydroxy-ethylamino)-ethoxy)-4-methyl-7-(3-phenylpropoxy)-benzofuran Example 20a) (344 mg, 0.80 mmol) and 2-aminoethanol (2.5 eqs.) were reacted according to General Procedure E, except the reaction time was 15 hours. The crude product was purified by flash chromatography, eluting with methanol:dichloromethane (1:5) to afford the title compound as a dark brownish oil (138 mg, 42%). $^1$H NMR (300 MHz, CDCl$_3$): δ 2.06-2.16 (m, 2H), 2.31 (s, 3H), 2.53 (s, 3H), 2.74-2.87 (bm, 6H), 2.95 (t, J=4.9 Hz, 2H), 3.67 (t, J=5.1 Hz, 2H), 4.20 (t, J=4.9 Hz, 2H), 4.4 (t, J=6.5 Hz, 2H), 6.72 (d, J=2.1 Hz, 1H), 7.14-7.29 (m, 5H), 7.57 (d, J=2.1 Hz, 1H). MS (ES$^+$) m/z 412 (M+H$^+$).

Example 40

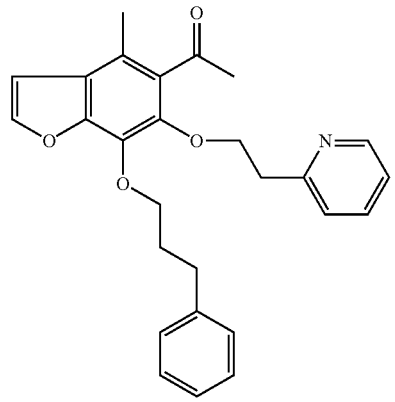

5-Acetyl-4-methyl-7-(3-phenylpropoxy)-6-(2-pyridin-2-yl-ethoxy)benzofuran

Example 18b) (324 mg, 1.00 mmol, 0.1 M), Cs$_2$CO$_3$ (2 eqs) and 2-pyridin-2-ylethyl methanesulfonate (3 eqs) were reacted according to General Procedure A. The crude residue was subjected to flash chromatography, eluting with ethylacetate:dichloromethane (1:4) to afford the title compound as a yellow oil (248 mg, 58%). $^1$H-NMR (300 MHz, CDCl$_3$) δ 1.99-2.09 (m, 2H), 2.28 (s, 3H), 2.32 (s, 3H), 2.81 (t, J=7.8 Hz, 2H), 3.18 (t, J=6.5 Hz, 2H), 4.27 (t, J=6.3 Hz, 2H), 4.44 (t, J=6.5 Hz, 2H), 6.71 (d, J=2.1 Hz, 1H), 7.07-7.29 (m, 7H), 7.55-7.59 (m, 2H), 8.52 (d, J=3.9 Hz, 1H). MS (ES$^+$) m/z 429.9 (M+H$^+$).

Example 41

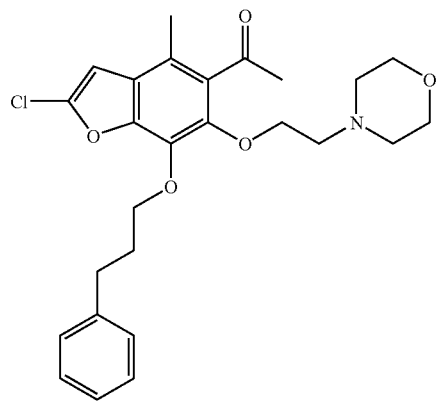

1-[2-Chloro-4-methyl-6-(2-morpholin-4-yl-ethoxy)-7-(3-phenyl-propoxy)-benzofuran-5-yl]-ethanone To a solution of Example 20a) (120 mg, 0.278 mmol) in dry DMF (1.5 ml) was added N-chlorosuccinimide (74 mg, 0.554 mmol) and the reaction was stirred at 75° C. for 3 h. After cooling the reaction was quenched with 10% $Na_2S_2O_{3\,(aq)}$ (20 ml) and extracted with EtOAc (20 ml). The organic layer was washed with water (20 ml) and brine (20 ml), dried over $MgSO_4$ and concentrated under vacuum. The residue was subjected to silica-gel flash chromatography (eluent=5% EtOAc in hexanes) to provide the crude 2-chloro derivative (~45 mg), which was dissolved in dry DMF (1.5 ml) and treated with excess morpholine (50 ul). After stirring at 70° C. overnight the reaction was cooled, quenched with water (20 ml) and extracted with EtOAc (20 ml). The organic layer was washed with brine (20 ml), dried over $MgSO_4$ and concentrated under vacuum. The crude residue was purified by silica-gel flash chromatography (eluent=15% EtOAc in DCM) to provide the product as a clear oil (23 mg, 18% over 2 steps). $^1$H NMR (300 MHz, $CDCl_3$): δ 2.06-2.15 (m, 2H), 2.25 (s, 3H), 2.47-2.50 (m, 4H), 2.54 (s, 3H), 2.66 (t, J=5.6 Hz, 2H), 2.86 (t, J=7.4 Hz, 2H), 3.67-3.70 (m, 4H), 4.11 (t, J=5.6 Hz, 2H), 4.33 (t, J=6.3 Hz, 2H), 6.54 (s, 1H), 7.16-7.31 (m, 5H). MS ($ES^+$) m/z 471.9 ($M+H^+$).

Example 42

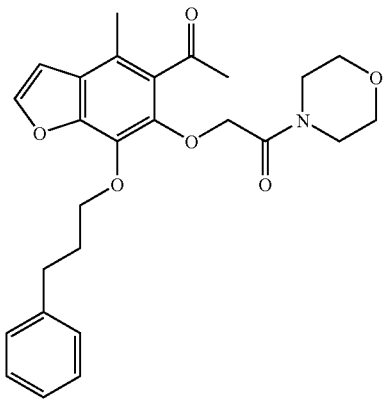

2-[5-Acetyl-4-methyl-7-(3-phenyl-propoxy)-benzofuran-6-yloxy]-1-morpholin-4-yl-ethanone Example 18b) (39 mg, 0.12 mmol) was reacted with 2-chloro-1-morpholin-4-yl-ethanone (23 mg, 0.14 mmol) as described under General Procedure A and the crude residue was purified by silica-gel flash chromatography (petroleum ether/ethyl acetate, 9:1) to provide the title compound (41 mg, 76%). $^1$H NMR (300 MHz, $CDCl_3$): δ 2.02-2.15 (m, 2H), 2.31 (s, 3H), 2.56 (s, 3H), 2.80-2.85 (m, 2H), 3.44-3.62 (m, 8H), 4.38 (t, J=6.5 Hz, 2H), 4.71 (s, 2H), 6.74 (d, J=2.2 Hz, 1H), 7.17-7.27 (m, 5H), 7.57 (d, J=2.2 Hz, 1H). MS ($ES^+$) m/z 452.2 ($M+H^+$).

Example 43

Step i

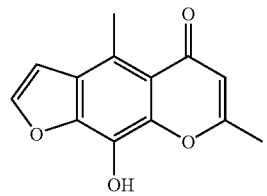

43a)
9-Hydroxy-4,7-dimethyl-furo[3,2-g]chromen-5-one

The title compound was prepared by treatment of Example 4a) with $BBr_3$ according to General Procedure D in 78% yield. $^1$H NMR (300 MHz, DMSO-d6): δ 2.33 (s, 3H, $CH_3$), 2.79 (s, 3H, $CH_3$), 6.02 (s, 1H), 7.13 (d, J=2.1 Hz, 1H), 8.02 (d, J=2.1 Hz, 1H), 10.29 (s, 1H, OH).

Step ii

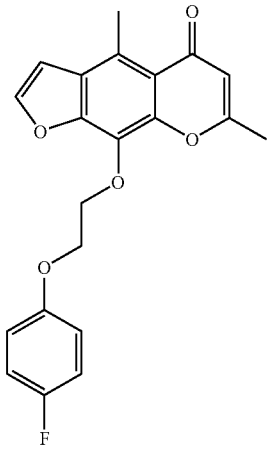

43b) 9-[2-(4-Fluoro-phenoxy)-ethoxy]-4,7-dimethyl-furo[3,2-g]chromen-5-one

Example 43a) was treated with 1-(2-bromoethoxy)-4-fluorobenzene according to General Procedure A. The crude residue was subjected to flash chromatography, eluting with ethylacetate:dichloromethane (1:9) to afford the title compound in 67% yield. $^1$H NMR (300 MHz, $CDCl_3$): δ 2.25 (s, 3H, CH₃), 2.97 (s, 3H, CH₃), 4.31 (t, J=4.5, 2H), 4.70 (t, J=4.5, 2H), 6.02 (s, 1H), 6.78-6.98 (m, 5H), 7.63 (d, J=2.1 Hz, 1H).

Step iii

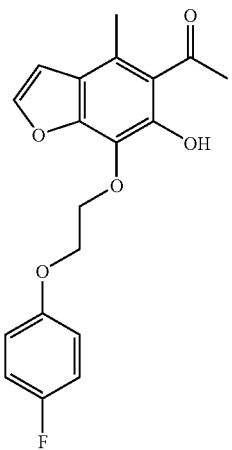

43c) 5-Acetyl-7-(2-(4-fluorophenoxy)-ethoxy)-6-hydroxy-4-methylbenzofuran

The title compound was prepared from Example 43b) as described under General Procedure B and the crude residue was subjected to flash chromatography, eluting with ethylacetate:dichloromethane (1:19) to afford the title compound in 55% yield. ¹H NMR (300 MHz, CDCl₃): δ 2.47 (s, 3H, CH₃), 2.60 (s, 3H, CH₃), 4.24 (t, J=4.5, 2H), 4.60 (t, J=4.5, 2H), 6.73 (d, J=2.1 Hz, 1H), 6.84-6.99 (m, 4H), 7.51 (d, J=2.1 Hz, 1H), 8.39 (s, 1H). MS (ES⁺) m/z 344.9 (M+H⁺).

Step iv

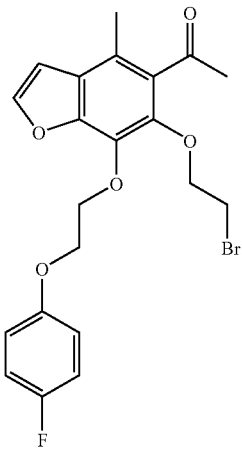

43d) 5-Acetyl-6-(2-bromoethoxy)-7-(2-(4-fluorophenoxy)-ethoxy)-4-methylbenzofuran The title compound was prepared by reacting Example 43c) with 1,2-dibromoethane (4 eq.) as described under General Procedure A and the crude residue was subjected to flash chromatography, eluting with hexane:dichloromethane (2:1, 1:1, 1:0) to afford the title compound in 72% yield. ¹H NMR (300 MHz, CDCl₃): δ 2.32 (s, 3H, CH₃), 2.53 (s, 3H, CH₃), 3.53 (t, J=6.3 Hz, 2H), 4.29 (t, J=4.5, 2H), 4.35 (t J=6.3 Hz, 2H), 4.68 (t, J=4.2, 2H), 6.75 (d, J=2.1 Hz, 1H), 6.83-6.99 (m, 4H), 7.58 (d, J=2.1 Hz, 1H). MS (ES⁺) m/z 450.8, 452.8 (M+H⁺).

Step v

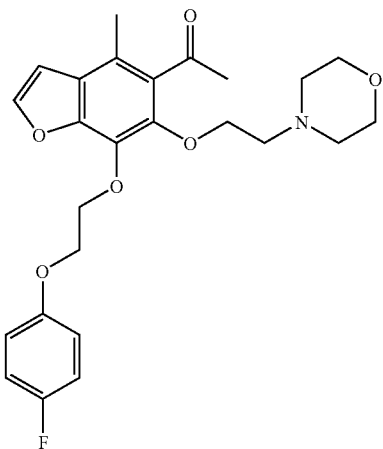

43e) 1-[7-[2-(4-Fluoro-phenoxy)-ethoxy]-4-methyl-6-(2-morpholin-4-yl-ethoxy)-benzofuran-5-yl]-ethanone Example 43e) was prepared from 43 d) and morpholine as described under General Procedure E in 90% yield. ¹H NMR (300 MHz, CDCl₃): δ 2.31 (s, 3H), 2.44-2.47 (m, 4H), 2.55 (s, 3H), 2.64 (t, J=5.6 Hz, 2H), 3.64-3.67 (m, 4H), 4.16 (t, J=5.6 Hz, 2H), 4.26-4.29 (m, 2H), 4.66-4.70 (m, 2H), 6.74 (d, J=2.2 Hz, 1H), 6.83-6.88 (m, 2H), 6.92-6.99 (m, 2H), 7.57 (d, J=2.2 Hz, 1H). MS (ES⁺) m/z 457.9 (M+H⁺).

Example 44

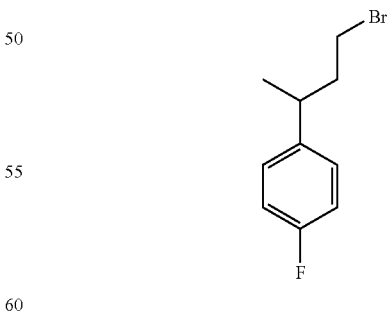

44a) 1-(3-Bromo-1-methyl-propyl)-4-fluorobenzene

A solution of ethyl 3-(4-fluorophenyl)butanoate (2.85 g, 13.6 mmol) in THF (10 mL) was added to a solution of lithium aluminum hydride (0.77 g, 1.5 mmol) in THF (60 mL) at 0° C. The reaction was stirred at room temperature overnight, then cooled to 0° C., quenched with NH$_4$Cl$_{(aq)}$ (sat., 50 mL) and extracted with EtOAc (3×100 mL). The pooled organics were washed with brine (100 mL), dried (Na$_2$SO$_4$) and concentrated under vacuum to give the alcohol, which was used directly in the next step. Bromine (1.03 mL, 20.0 mmol) was added dropwise to a solution of triphenylphosphine (5.24 g, 20.0 mmol) in DCM (80 mL) at 0° C. until an orange colour persisted. The reaction mixture was stirred at room temperature for 90 min, then a solution of the alcohol (2.37 g, 14.1 mmol) in DCM (20 mL) was added and the reaction mixture stirred overnight. The reaction mixture was concentrated under vacuum and the resulting residue was sonicated for 5 min in petroleum ether (100 mL). The suspension was filtered, and the white solid washed with petroleum spirit. The washings were concentrated under vacuum to give the title compound (2.56 g, 81% over 2 steps) as a colourless oil. $^1$H-NMR (300 MHz, CDCl$_3$) δ 1.31 (d, J=6.9 Hz, 3H), 2.08-2.15 (m, 2H), 2.92-3.00 (m, 1H), 3.15-3.20 (m, 1H), 3.31-3.36 (m, 1H), 7.18-7.26 (m, 2H)

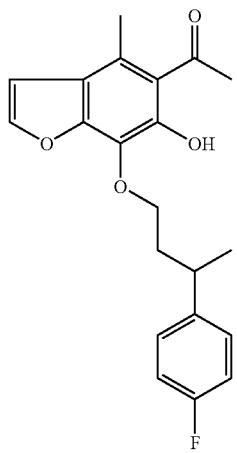

44c) 5-Acetyl-7-(3-(4-fluorophenyl)butoxy)-6-hydroxy-4-methylbenzofuran

Example 44b) (540 mg, 1.42 mmol) was hydrolysed according to General Procedure B and the crude was purified with flash silica gel column chromatography eluting with ethylacetate:hexane (1:9) to offer the title compound (260 mg, 51%) as yellow oil. $^1$H-NMR (300 MHz, CDCl$_3$) δ 1.29 (d, J=6.9 Hz, 3H), 1.93-2.14 (m, 2H), 2.52 (s, 3H), 2.63 (s, 3H), 2.99-3.11 (m, 1H), 4.14-4.28 (m, 2H), 6.71 (d, J=2.1 Hz, 1H), 6.92-6.98 (m, 2H), 7.15-7.19 (m, 2H), 7.47 (d, J=2.1 Hz, 1H), 9.16 (s, 1H). MS (ES$^+$) m/z 356.9 (M+H$^+$).

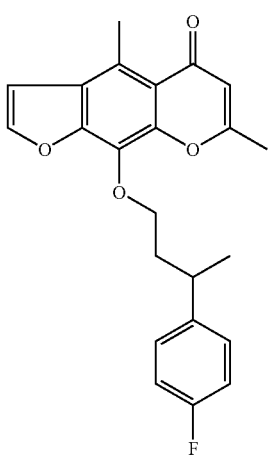

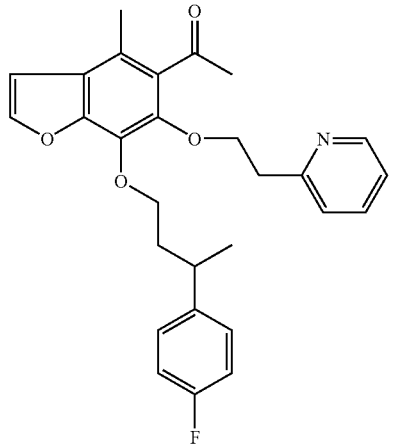

44d) 5-Acetyl-7-(3-[4-fluorophenyl]butoxy)-4-methyl-6-(2-pyridin-2-yl-ethoxy)benzofuran 44b) 9-[3-(4-Fluoro-phenyl)-butoxy]-4,7-dimethyl-furo[3,2-g]chromen-5-one The example 43a) (400 mg, 1.74 mmol) and 44a) (1.2 eqs) were reacted according to General Procedure A and the crude was purified by flash chromatography eluting with ethylacetate:hexane (2:8) to offer the title compound (540 mg, 82%) as white solid. $^1$H-NMR (300 MHz, CDCl$_3$) δ 1.31 (d, J=6.9 Hz, 3H), 1.98-2.15 (m, 2H), 2.34 (s, 3H), 2.94 (s, 3H), 3.11-3.18 (m, 1H), 4.15-4.33 (m, 2H), 6.04 (s, 1H), 6.90-6.99 (m, 3H), 7.16-7.20 (m, 2H), 7.62 (d, J=2.1 Hz, 1H). MS (ES$^+$) m/z 380.9 (M+H$^+$).

A suspension of Example 44c) (60 mg, 0.17 mmol, 0.2 M), Cs$_2$CO$_3$ (109 mg, 0.33 mmol) and 2-pyridin-2-ylethyl methanesulfonate (51 mg, 0.25 mmol) were heated in anhydrous DMF at 60-70° C. under inert atmosphere. After 2 h additional amounts of Cs$_2$CO$_3$ (33 mg, 0.10 mmol) and 2-pyridin-2-ylethyl methanesulfonate (20 mg, 0.10 mmol) were added and reaction continued for 20 minutes. Then solvents were removed under vacuum and the residue was dissolved in EtOAc (25 mL) and washed with NH$_4$Cl (aq) (20 mL), water (20 mL) and brine (20 mL). The organic layer was dried (MgSO₄) and evaporated. The crude was purified by flash silica-gel chromatography eluting with ethylacetate:dichloromethane (1:9) to afford the title compound as a yellow oil (53 mg, 68%). ¹H-NMR (300 MHz, CDCl₃) δ 1.26 (d, J=6.9 Hz, 3H), 1.86-2.10 (m, 2H), 2.26 (s, 3H), 2.32 (s, 3H), 2.96-3.08 (m, 1H), 3.16 (t, J=6.5 Hz, 2H), 4.06-4.22 (m, 2H), 4.40 (t, J=6.5 Hz, 2H), 6.69 (d, J=2.1 Hz, 1H), 6.89-6.97 (m, 2H), 7.09-7.23 (m, 4H), 7.52 (d, J=2.1 Hz, 1H), 7.60 (dt, J=1.7 Hz, 7.6 Hz, 1H), 8.52 (d, J=4.3 Hz, 1H). MS (ES⁺) m/z 461.9 (M+H⁺).

Example 45

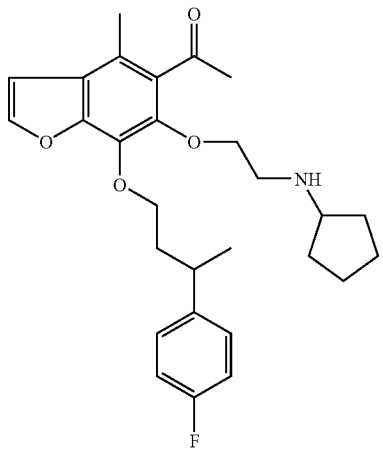

45b) 5-Acetyl-7-(3-[4-fluorophenyl]butoxy)-4-methyl-6-(2-Cyclopentylamino-ethoxy)benzofuran Example 45a) (170 mg, 0.37 mmol, 0.2 M) and cyclopentylamine were heated in anhydrous DMF at 60-70° C. under inert atmosphere for 6 h. The reaction was cooled, quenched by addition of water and extracted with ethyl acetate. The organic layer was washed with brine, dried over MgSO₄ and evaporated. The crude mixture was purified by flash chromatography eluting with ethyl acetate:dichloromethane (1:2) to offer the title compound (145 mg, 84%) as a clear oil. ¹H-NMR (300 MHz, CDCl₃) δ 1.28-1.36 (m, 5H), 1.50-1.70 (m, 5H), 1.77-1.86 (m, 2H), 2.02-2.14 (m, 2H), 2.29 (s, 3H), 2.51 (s, 3H), 2.85 (t, J=5.2 Hz, 2H), 3.02-3.13 (m, 2H), 4.10 (t, J=5.2 Hz, 2H), 4.17-4.28 (m, 2H), 6.71 (d, J=2.1 Hz, 1H), 6.92-6.98 (m, 2H), 7.15-7.20 (m, 2H), 7.52 (d, J=2.1 Hz, 1H). MS (ES⁺) m/z 468 (M+H⁺).

Example 46

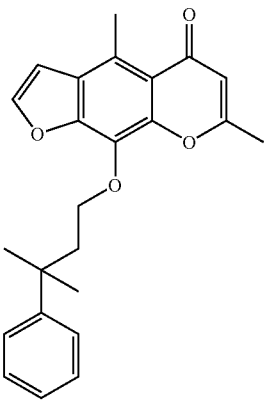

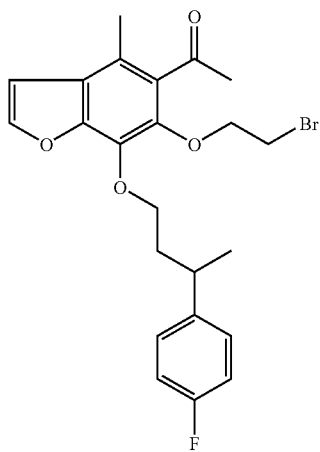

45a) 5-Acetyl-6-(2-bromoethoxy)-7-(3-(4-fluorophenyl)butoxy)-4-methylbenzofuran

Example 44c) (200 mg, 0.56 mmol), 1,2-dibromoethane (6.0 eqs) and Cs₂CO₃ (1.3 eqs) were heated in anhydrous DMF (2 ml) at 60° C. for 1 h and an additional amount of Cs₂CO₃ (0.4 eqs) was added and stirring continued for another 30 min. The reaction mixture was then diluted with ethyl acetate and washed twice with 10% citric acid and then brine, dried over MgSO₄, and concentrated in vacuo. The excess of 1,2-dibromoethane was removed under high vacuum at 50° C. to offer the title compound (260 mg, 100%) as clear oil. ¹H-NMR (300 MHz, CDCl₃) δ 1.29 (d, J=6.9 Hz, 3H), 1.93-2.13 (m, 2H), 2.30 (s, 3H), 2.53 (s, 3H), 3.04-3.11 (m, 1H), 3.53 (t, J=6.2 Hz, 2H), 4.16-4.30 (m, 4H), 6.72 (d, J=2.1 Hz, 1H), 6.93-6.99 (m, 2H), 7.15-7.20 (m, 2H), 7.55 (d, J=2.1 Hz, 1H). MS (ES⁺) m/z 462.8, 464.8 (M+H⁺).

46a) 4,7-Dimethyl-9-(3-methyl-3-phenyl-butoxy)-furo[3,2-g]chromen-5-one

Example 46a) was prepared by reacting Example 43a) with 4-bromo-1-methyl-1-phenyl-butane (prepared by triphenylphosphine/bromine bromination of the known precursor alcohol—Zhurnal Organicheskoi Khimii, 24 (8), p 1610, 1988) as described in General Procedure A in 49% yield.

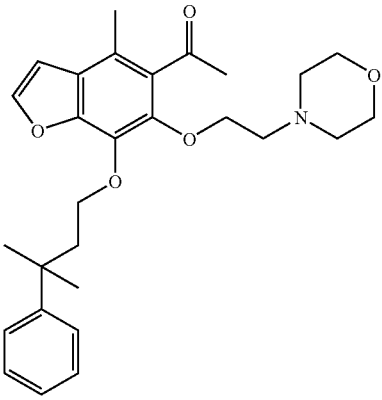

46b) rac-1-[4-Methyl-7-(3-methyl-3-phenyl-butoxy)-6-(2-morpholin-4-yl-ethoxy)-benzofuran-5-yl]ethanone The title compound was prepared from Example 46a) in 39% yield over three steps in the same manner as described for Example 43 Steps iii-v. $^1$H NMR (300 MHz, CDCl$_3$: δ 1.39 (s, 6H), 2.20 (t, J=7.6 Hz, 2H), 2.28 (s, 3H), 2.47-2.50 (m, 4H), 2.52 (s, 3H), 2.63 (t, J=5.6 Hz, 2H), 3.69-3.72 (m, 4H), 4.04 (t, J=5.6 Hz, 2H), 4.16 (t, J=7.6 Hz, 2H), 6.69 (m, 1H), 7.14-7.19 (m, 1H), 7.24-7.37 (m, 4H), 7.51 (m, 1H). MS (ES$^+$) m/z 466.0 (M+H$^+$).

Example 47

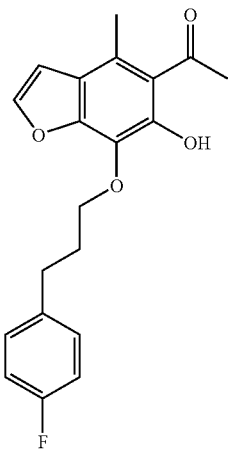

47a) 5-Acetyl-7-(3-(4-fluorophenyl)propoxy)-6-hydroxy-4-methylbenzofuran 4,9-Dihydroxy-7-methyl-5H-furo[3,2-g]chromen-5-one was reacted with 1-bromo-3-(4-fluorophenyl)propane according to General Procedure A to give 9-(3-[4-fluorophenyl]propoxy)-4-hydroxy-5H-furo[3,2-g]chromen-5-one, that was further reacted according to General Procedure G step 1-3, to provide the title compound in 22% yield (over 4 steps). $^1$H NMR (300 MHz, CDCl$_3$): δ 2.04-2.14 (m, 2H), 2.53 (s, 3H, CH$_3$), 2.63 (s, 3H, CH$_3$), 2.83 (t, J=7.8 Hz, 2H), 4.34 (t, J=6.3, 2H), 6.73 (d, J=2.1, 1H), 6.94 (t J=8.7 Hz, 2H), 7.13-7.18 (m, 2H), 7.50 (d, J=2.1 Hz, 1H), 8.98 (s, 1H, OH). MS (ES) m/z: 342.9 (M+H$^+$).

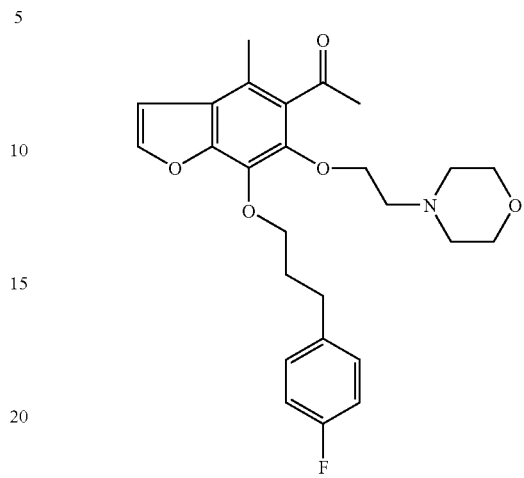

47b) 5-Acetyl-7-(3-(4-fluorophenyl)propoxy)-4-methyl-6-(2-morpholinoethoxy)benzofuran The title compound was prepared from Example 47a) as described in Example 43 step iv, v in 60% yield. $^1$H-NMR (300 MHz, CDCl$_3$) δ 2.04-2.13 (m, 2H), 2.31 (s, 3H), 2.49 (t J=4.2 Hz, 4H), 2.55 (s, 3H), 2.67 (t, J=5.6 Hz, 2H), 2.84 (t, J=7.3 Hz, 2H), 3.69 (t, J=4.7 Hz, 4H), 4.13 (t, J=5.7 Hz, 2H), 4.34 (t, J=6.3 Hz, 2H), 6.73 (d, J=2.1 Hz, 1H), 6.95 (t, J=8.7 Hz, 1H), 7.14-7.19 (m, 2H), 7.56 (d, J=2.1 Hz, 1H). MS (ES$^+$) m/z 455.9 (M+H$^+$).

Example 48

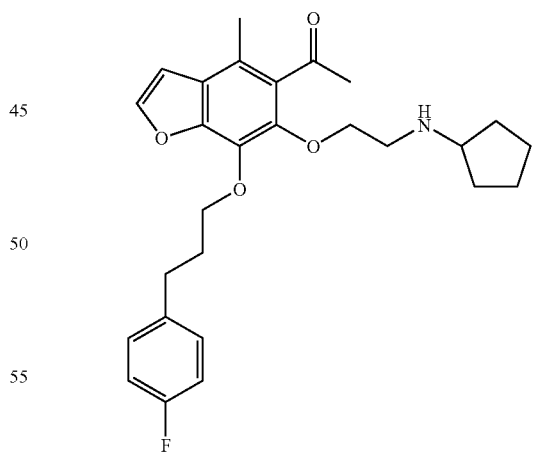

1-[6-(2-Cyclopentylamino-ethoxy)-4-methyl-7-(3-(4-fluoro-phenyl)-propoxy)-benzofuran-5-yl]-ethanone The title compound was prepared in 2 steps from Example 47a) in 89% yield in the same manner as described for Example 43 Steps iv-v. $^1$H NMR (300 MHz, CDCl$_3$): δ 1.28-

1.35 (m, 2H), 1.49-1.56 (m, 2H), 1.61-1.70 (m, 2H), 1.79-1.85 (m, 2H), 2.03-2.12 (m, 2H), 2.31 (s, 3H), 2.53 (s, 3H), 2.80-2.89 (m, 4H), 3.09 (quintet, J=6.5 Hz, 1H), 4.14 (t, J=5.2 Hz, 2H), 4.33 (t, J=6.4 Hz, 2H), 6.73 (d, J=2.2 Hz, 1H), 6.92-6.98 (m, 2H), 7.14-7.19 (m, 2H), 7.56 (d, J=2.2 Hz, 1H). MS (ES$^+$) m/z 454.0 (M+H$^+$).

Example 49

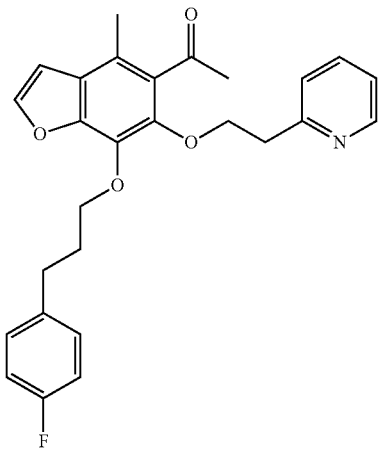

1-[7-[3-(4-Fluoro-phenyl)-propoxy]-4-methyl-6-(2-pyridin-2-yl-ethoxy)-benzofuran-5-yl]-ethanone The title compound was prepared from Example 47a) and 2-pyridin-2-ylethyl methanesulfonate in 61% yield as described in General Procedure A. $^1$H NMR (300 MHz, CDCl$_3$): δ 1.96-2.06 (m, 2H), 2.28 (s, 3H), 2.33 (s, 3H), 2.78 (t, J=7.4 Hz, 2H), 3.18 (t, J=6.6 Hz, 2H), 4.25 (t, J=6.3 Hz, 2H), 4.44 (t, J=6.6 Hz, 2H), 6.71 (d, J=2.2 Hz, 1H), 6.90-6.97 (m, 2H), 7.08-7.23 (m, 4H), 7.55-7.60 (m, 2H), 8.51 (d, J=4.8 Hz, 1H). MS (ES$^+$) m/z 447.9 (M+H$^+$).

Example 50

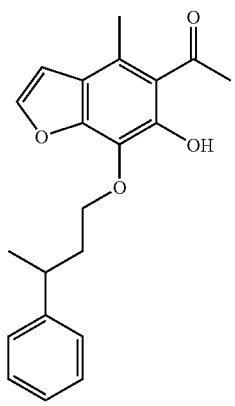

50a) 1-[6-Hydroxy-4-methyl-7-(3-RS-phenylbutoxy)-benzofuran-5-yl]-ethanone

To a suspension of Example 43a) (92 mg, 0.40 mmol) in dichloromethane/tetrahydrofuran (1:1, 4 mL) was added polymer-bound triphenylphosphine (1.0 mmol loading, 600 mg, 0.60 mmol), 3-RS-phenylbutan-1-ol (95 µL, 0.65 mmol) and diethylazodicarboxylate (94 µL, 0.60 mmol). The reaction mixture was stirred at rt for 16 h then filtered through a Celite pad, washing with dichloromethane and tetrahydrofuran. The solvent was concentrated in vacuo and the crude product was purified by flash chromatography eluting with ethyl acetate:petroleum ether (1:4) to offer a mixture of the intermediate chromenone and 3-RS-phenyl-butan-1-ol. This mixture was treated as described under General Procedure B to afford the title compound (60 mg, 44% yield over 2 steps). $^1$H NMR (300 MHz, CDCl$_3$): δ 1.32 (d, J=7.0 Hz, 3H), 2.06-2.13 (m, 2H), 2.53 (s, 3H), 2.65 (s, 3H), 3.01-3.09 (m, 1H), 4.22-4.30 (m, 2H), 6.73 (d, J=2.3 Hz, 1H), 7.16-7.32 (m, 5H), 7.49 (d, J=2.3 Hz, 1H), 8.79 (s, 1H).

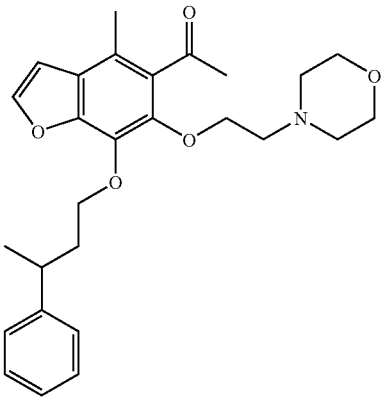

50b) 1-[4-Methyl-6-(2-morpholin-4-yl-ethoxy)-7-(3-phenyl-butoxy)-benzofuran-5-yl]-ethanone Example 50a) was treated with 4-(2-chloroethyl)morpholine hydrochloride as described under General Procedure I and the crude product was purified by flash chromatography with methanol:ethyl acetate:dichloromethane (1:29:70) to give the title compound in 79% yield. $^1$H-NMR (300 MHz, CDCl$_3$) δ 1.33 (d, J=7.0 Hz, 3H), 2.03-2.10 (m, 2H), 2.29 (s, 3H), 2.47-2.50 (m, 4H), 2.54 (s, 3H), 2.65 (t, J=3.3 Hz, 2H), 3.01-3.09 (m, 1H), 3.67-3.71 (m, 4H), 4.10 (t, J=3.4 Hz, 2H), 4.21-4.29 (m, 2H), 6.71 (d, J=2.2 Hz, 1H), 7.14-7.25 (m, 5H), 7.53 (d, J=2.2 Hz, 1H).

Example 51

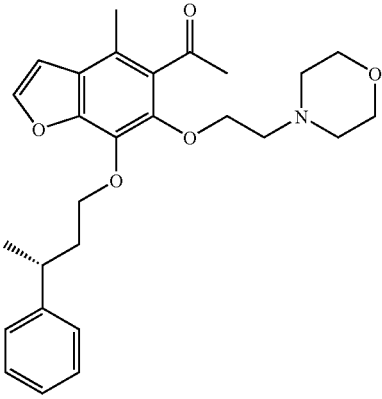

1-[4-Methyl-6-(2-morpholin-4-yl-ethoxy)-7-(3-phenyl-butoxy)-benzofuran-5-yl]-ethanone Example 43a) and 3-R-phenylbutan-1-ol were treated as described above for Example 50a) and 50 b) to give the title compound in 28% yield over 3 steps. $^1$H-NMR (300 MHz, CDCl$_3$) δ 1.34 (d, J=7.0 Hz, 3H), 2.05-2.12 (m, 2H), 2.31 (s, 3H), 2.48-2.520 (m, 4H), 2.56 (s, 3H), 2.67 (t, J=3.3 Hz, 2H), 3.03-3.11 (m, 1H), 3.69-3.73 (m, 4H), 4.11 (t, J=3.4 Hz, 2H), 4.22-4.30 (m, 2H), 6.72 (d, J=2.2 Hz, 1H), 7.16-7.31 (m, 5H), 7.53 (d, J=2.2 Hz, 1H).

Example 52 rac-1-[4-Methyl-7-(3-phenyl-butoxy)-6-(2-pyridin-2-yl-ethoxy)-benzofuran-5-yl]-ethanone The title compound was prepared from Example 50a) and 2-pyridin-2-ylethyl methanesulfonate in 64% yield as described in General Procedure A. $^1$H NMR (300 MHz, CDCl$_3$): δ 1.29 (d, J=7.0 Hz, 6H), 1.98-2.04 (m, 2H), 2.26 (s, 3H), 2.31 (s, 3H), 2.99-3.06 (m, 1H), 3.16 (t, J=6.6 Hz, 2H), 4.10-4.23 (m, 2H), 4.41 (t, J=6.6 Hz, 2H), 6.69 (d, J=2.0 Hz, 1H), 7.09-7.28 (m, 8H), 7.52 (d, J=2.0 Hz, 1H), 7.55-7.60 (m, 1H), 8.52 (d, J=4.6 Hz, 1H). MS (ES$^+$) m/z 443.9 (M+H$^+$).

Example 53

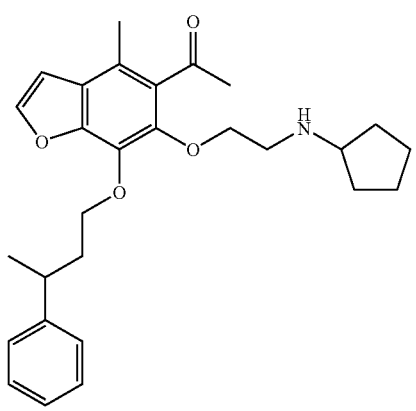

1-[6-(2-Cyclopentylamino-ethoxy)-4-methyl-7-(3-phenyl-butoxy)-benzofuran-5-yl]-ethanone The title compound was prepared in 2 steps from Example 50a) in 76% yield in the same manner as described for Example 43 Steps iv-v. $^1$H NMR (300 MHz, CDCl$_3$): δ 1.34 (d, J=7.0 Hz, 3H), 1.37-1.42 (m, 2H), 1.52-1.57 (m, 2H), 1.68-1.89 (m, 4H), 2.06-2.13 (m, 2H), 2.31 (s, 3H), 2.53 (s, 3H), 2.89 (t, J=5.3 Hz, 2H), 3.03-3.16 (m, 2H), 4.16 (t, J=5.3 Hz, 2H), 4.22-4.28 (m 2H), 6.72 (d, J=2.2 Hz, 1H), 7.16-7.26 (m, 5H), 7.54 (d, J=2.2 Hz, 1H). MS (ES$^+$) m/z 450.3 (M+H$^+$).

Example 54

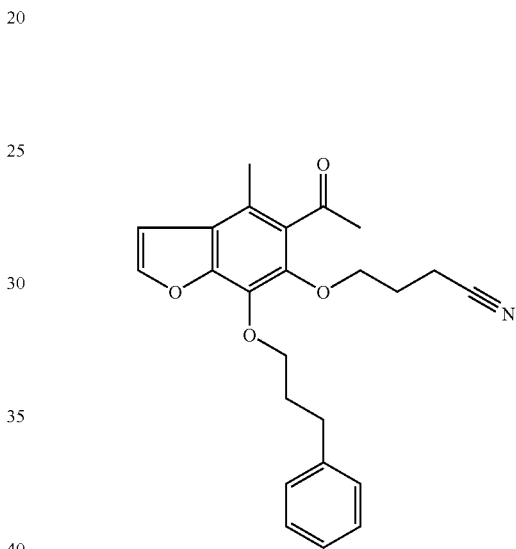

54a) 5-Acetyl-6-(3-cyanopropoxy)-4-methyl-7-(3-phenylpropoxy)benzofuran

A suspension of Example 27a) (445 mg, 1.00 mmol) and NaCN (75 mg, 1.53 mmol) in anhydrous DMSO (3 ml) was heated at 65-70° C. overnight under inert atmosphere. The reaction was cooled and quenched by addition of aqueous NH$_4$Cl solution and extracted with EtOAc. The organic portion was dried (MgSO$_4$), evaporated under vacuum and residue was purified by flash chromatography eluting with dichloromethane yielding (150 mg, 38%) of the title compound. $^1$H NMR (300 MHz, CDCl$_3$): δ 1.98-2.18 (m, 4H), 2.30 (s, 3H), 2.51 (s, 3H), 2.84 (t, J=7.3 Hz, 2H), 4.09 (t, J=5.8 Hz, 2H), 4.37 (t, J=6.5 Hz, 2H), 6.73 (d, J=2.1 Hz, 1H), 7.16-7.30 (m, 5H), 7.57 (d, J=2.1 Hz, 1H). MS (ES$^+$) m/z 391.9, 408.9 (M+M$^+$, NH$_4^+$).

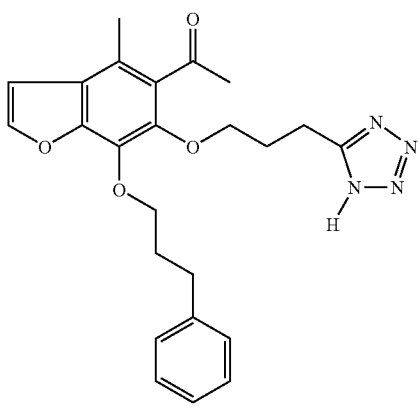

54b) 5-Acetyl-6-(3-(1H-tetrazol-5-yl)-propoxy)-4-methyl-7-(3-phenylpropoxy)benzofuran Example 54a) (130 mg, 0.33 mmol), TBAF (1.0 eqs) and TMS-N$_3$ (1.5 eqs) were heated at 110-120° C. for 72 hours in a closed RB Flask. The reaction mixture was cooled, quenched by addition of aqueous NH$_4$Cl (20 mL) and extracted with EtOAc (20 mL). After evaporation, the crude was purified by flash chromatography with methanol:ethylacetate:dichloromethane (5:20:75) to give the title compound in 33% yield. $^1$H NMR (300 MHz, CDCl$_3$): δ 2.04-2.14 (m, 4H), 2.34 (s, 3H), 2.58 (s, 3H), 2.81 (t, J=8.0 Hz, 2H), 3.12 (t J=6.8 Hz, 2H), 4.00 (t, J=5.3 Hz, 2H), 4.40 (t, J=6.5 Hz, 2H), 6.74 (d, J=2.1 Hz, 1H), 7.16-7.29 (m, 5H), 7.59 (d, J=2.1 Hz, 1H). MS (ES$^+$) m/z 434.9 (M+H$^+$).

Example 55

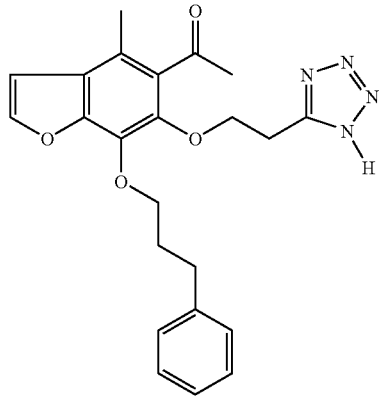

5-Acetyl-6-(3-(1H-tetrazol-5-yl)-ethoxy)-4-methyl-7-(3-phenylpropoxy)benzofuran

The title compound was prepared in two steps by reacting Example 20a) with NaCN (0.5 eqs), followed by reaction with TMS-N$_3$ and TBAF as described in Example 54. Purification of crude give the title compound in 5% yield (over 2 steps). $^1$H NMR (300 MHz, CDCl$_3$): δ 2.10-2.20 (m, 2H), 2.33 (s, 3H), 2.49 (s, 3H), 2.78 (t, J=7.9 Hz, 2H), 3.37 (t J=6.8 Hz, 2H), 4.00 (t, J=5.4 Hz, 2H), 4.31 (t, J=5.4 Hz, 2H), 4.53 (t, J=6.7 Hz, 2H), 6.75 (d, J=2.1 Hz, 1H), 7.15-7.28 (m, 5H), 7.59 (d, J=2.1 Hz, 1H). MS (ES$^+$) m/z 420.9 (M+H$^+$).

Example 56

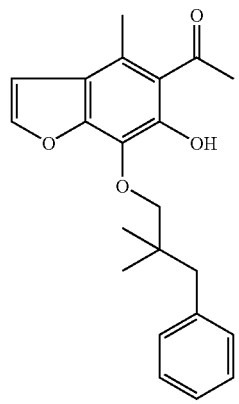

56a) 5-Acetyl-7-(2,2-dimethyl-3-phenylpropoxy)-4-methyl-6-(2-morpholinoethoxy)benzofuran Example 43a) (115 mg, 0.50 mmol), 1-bromo-2,2-dimethyl-3-phenylpropane (98.4 mg, 0.60 mmol) and PPh$_3$ (157 mg, 0.60 mmol) were added to anhydrous THF (0.8 mL) in a Schlenk tube under N$_2$ atmosphere and sonicated for 10 minutes, and di-tertbutyl azodicarboxylate (138 mg, 0.60 mmol) was then added. The reaction mixture was sonicated for 3 hours. Additional amount of PPh$_3$ (80 mg, 0.30 mmol) and di-tertbutyl azodicarboxylate (69 mg, 0.30 mmol) were added to the reaction mixture and sonicated for a further 2 hours. The solvents were removed under vacuum and the residue was chromatographed on silica-gel to give coupled product (70 mg, 37%). The isolated product was hydrolysed according to General Procedure B to afford the title compound in 54% yield. $^1$H NMR (300 MHz, CDCl$_3$): δ 1.05 (s, 6H), 2.52 (s, 3H), 2.64 (s, 3H), 2.78 (s, 2H), 3.98 (s, 2H), 6.73 (d, J=2.1 Hz, 1H), 7.18-7.29 (m, 5H), 7.50 (d, J=2.1 Hz, 1H), 8.91 (s, 1H). MS (ES$^+$) m/z 352.9 (M+H$^+$).

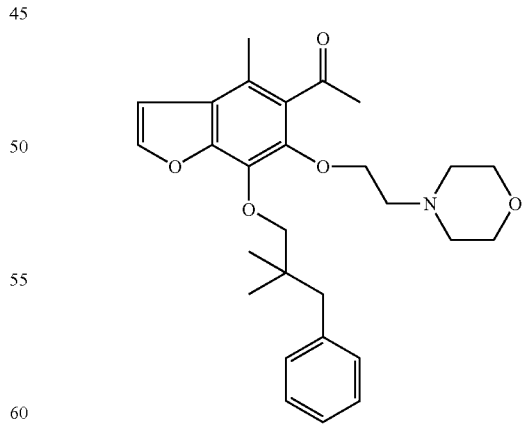

56b) 5-Acetyl-7-(2,2-dimethyl-3-phenylpropoxy)-4-methyl-6-(2-morpholinoethoxy)benzofuran The title compound was prepared from Example 56a) as described in Example 43 step iv and v in 64% yield (over 2 steps). ¹H-NMR (300 MHz, CDCl₃) δ 1.05 (s, 6H), 2.31 (s, 3H), 2.48 (t, J=4.5 Hz, 4H), 2.57 (s, 3H), 2.67 (t, J=5.7 Hz, 2H), 2.78 (s, 2H), 3.69 (t, J=4.9 Hz, 4H), 4.02 (s, 2H), 4.14 (t, J=5.7 Hz, 2H), 6.73 (d, J=2.1 Hz, 1H), 7.16-7.29 (m, 5H), 7.57 (d, J=2.1 Hz, 1H). MS (ES⁺) m/z 466.0 (M+H⁺).

Example 57

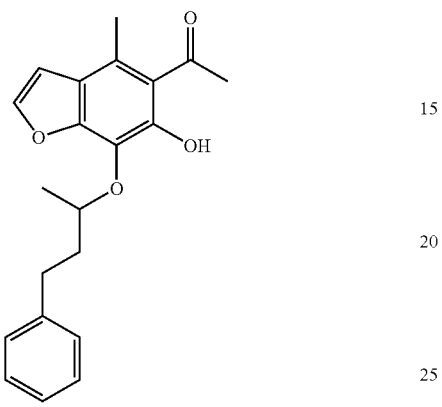

57a) 1-[6-Hydroxy-4-methyl-7-(1-RS-methyl-3-phenyl-propoxy)-benzofuran-5-yl]-ethanone To a suspension of Example 43a) (92 mg, 0.40 mmol) in dichloromethane/tetrahydrofuran (1:1, 4 mL) was added polymer-bound triphenylphosphine (1.0 mmol loading, 600 mg, 0.60 mmol), RS-4-phenylbutan-2-ol (92 μL, 0.60 mmol) and diethylazodicarboxylate (94 μL, 0.60 mmol). The reaction mixture was stirred at rt for 16 h then filtered through a Celite pad, washing with dichloromethane and tetrahydrofuran. The solvent was concentrated in vacuo and the crude product was purified by flash chromatography eluting with ethyl acetate:petroleum ether (1:9, 1:4) to offer the intermediate chromenone in 73% yield. This compound was treated as described under General Procedure B and the crude product was purified by flash chromatography eluting with ethyl acetate:petroleum ether (1:9) to afford the title compound in 64% yield. ¹H NMR (300 MHz, CDCl₃): δ 1.34 (d, J=6.2 Hz, 3H), 1.93-2.18 (m, 2H), 2.51 (s, 3H), 2.63 (s, 3H), 2.75-2.88 (m, 2H), 4.74-4.80 (m, 1H), 6.73 (d, J=2.3 Hz, 1H), 7.14-7.48 (m, 5H), 7.48 (d, J=2.3 Hz, 1H), 8.74 (s, 1H).

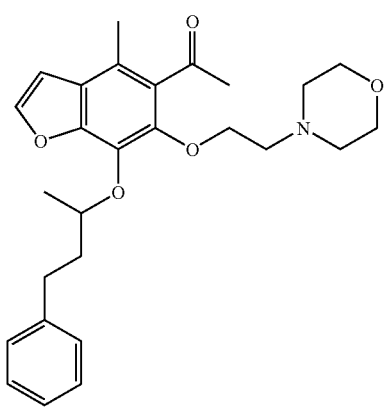

57b) 1-[4-Methyl-7-(1-RS-methyl-3-phenyl-propoxy)-6-(2-morpholin-4-yl-ethoxy)-benzofuran-5-yl]-ethanone Example 57a) was treated with 4-(2-chloroethyl)morpholine hydrochloride as described under General Procedure I and the crude product was purified by flash chromatography with methanol:ethylacetate:dichloromethane (1:29:70) to give the title compound in 56% yield. ¹H-NMR (300 MHz, CDCl₃) δ 1.33 (d, J=6.2 Hz, 3H), 1.92-2.09 (m, 2H), 2.31 (s, 3H), 2.48-2.50 (m, 4H), 2.55 (s, 3H), 2.66 (t, J=5.8 Hz, 2H), 3.67-3.70 (m, 4H), 4.12 (t, J=5.8 Hz, 2H), 4.80-4.86 (m, 1H), 6.73 (d, J=2.2 Hz, 1H), 7.14-7.28 (m, 5H), 7.55 (d, J=2.2 Hz, 1H).

Example 58

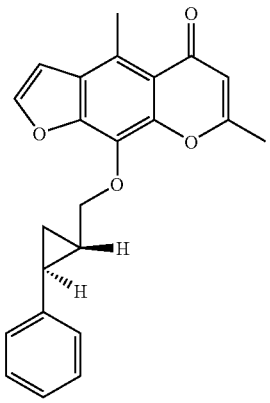

58a. rac-4,7-Dimethyl-9-(1S,2S-2-phenyl-cyclopropylmethoxy)-furo[3,2-g]chromen-5-one Example 58a) was prepared by reacting Example 43a) with trans-(2-bromomethyl-cyclopropyl)-benzene (Eur. Patent App. 445013, 4 Sep. 1991) as described in General Procedure A except the reaction was performed at rt. The title compound was furnished in 94% yield. ¹H NMR (300 MHz, CDCl₃): δ 0.96-1.02 (m, 2H), 1.60-1.63 (m, 1H), 1.74-1.80 (m, 1H), 2.23 (s, 3H), 2.96 (s, 3H), 4.22 (dd, J=10.9, 7.6 Hz, 1H), 4.48 (dd, J=10.9, 6.2 Hz, 1H), 5.97 (s, 1H), 6.88-6.90 (m, 3H), 7.08-7.23 (m, 3H), 7.59 (d, J=2.2 Hz, 1H). MS (ES⁺) m/z 360.9 (M+H⁺).

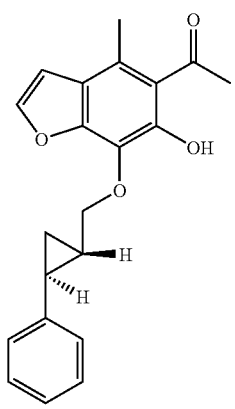

58b) rac-1-[6-Hydroxy-4-methyl-7-(1S,2S-2-phenyl-cyclopropylmethoxy)-benzofuran-5-yl]-ethanone The title compound was prepared from Example 58a) as described under General Procedure B in 46% yield. $^1$H NMR (300 MHz, CDCl$_3$): δ 0.96-1.05 (m, 2H), 1.54-1.62 (m, 1H), 1.82-1.88 (m, 1H), 2.51 (s, 3H), 2.60 (s, 3H), 4.28-4.34 (m, 2H), 6.72 (d, J=2.2 Hz, 1H), 6.95-6.98 (m, 2H), 7.09-7.23 (m, 3H), 7.47 (d, J=2.2 Hz, 1H), 9.02 (s, 1H). MS (ES$^+$) m/z 358.9 (M+Na$^+$).

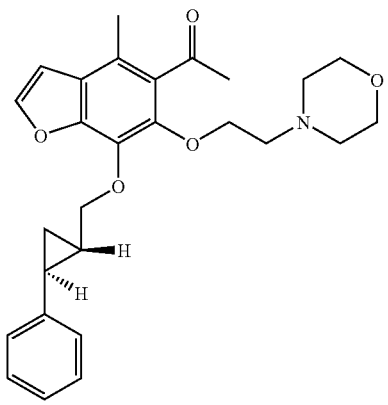

58c) 1-[4-Methyl-6-(2-morpholin-4-yl-ethoxy)-7-(1S,2S-2-phenyl-cyclopropylmethoxy)-benzofuran-5-yl]-ethanone The title compound was prepared from Example 58b) in 77% yield over two steps in the same manner as described for Example 43e). $^1$H NMR (300 MHz, CDCl$_3$): δ 0.99-1.04 (m, 2H), 1.58-1.65 (m, 1H), 1.85-1.91 (m, 1H), 2.30 (s, 3H), 2.44-2.47 (m, 4H), 2.51 (s, 3H), 2.63 (t, J=5.6 Hz, 2H), 3.66-3.69 (m, 4H), 4.13 (t, J=5.6 Hz, 2H), 4.28 (dd, J=10.5, 7.3 Hz, 1H), 4.37 (dd, J=10.5, 6.6 Hz, 1H), 6.71 (d, J=2.2 Hz, 1H), 6.98-7.00 (m, 2H), 7.10-7.21 (m, 3H), 7.54 (d, J=2.2 Hz, 1H). MS (ES$^+$) m/z 449.9 (M+H$^+$).

Example 59

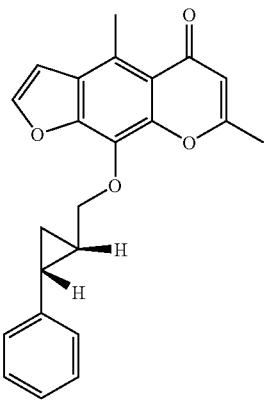

59a) rac-4,7-Dimethyl-9-(1S,2R-2-phenyl-cyclopropylmethoxy)-furo[3,2-g]chromen-5-one Example 59a) was prepared by reacting Example 43a) with cis-(2-bromomethyl-cyclopropyl)-benzene (prepared by triphenylphosphine/bromine bromination of the known alcohol precursor—JACS, 117 (43), p 10672, 1995) as described in General Procedure A except the reaction was performed at rt. The title compound was furnished in 64% yield. $^1$H NMR (300 MHz, CDCl$_3$): δ 0.88-0.94 (m, 1H), 1.08-1.16 (m, 1H), 1.70-1.77 (m, 1H), 2.26-2.30 (m, 1H), 2.30 (s, 3H), 2.92 (s, 3H), 4.07 (dd, J=10.9, 8.0 Hz, 1H), 4.15 (dd, J=10.9, 6.6 Hz, 1H), 6.00 (s, 1H), 6.87 (d, J=2.2 Hz, 1H), 7.06-7.16 (m, 5H), 7.58 (d, J=2.2 Hz, 1H). MS (ES$^+$) m/z 360.9 (M+H$^+$).

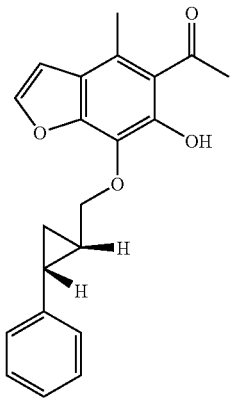

59b) rac-1-[6-Hydroxy-4-methyl-7-(1S,2R-2-phenyl-cyclopropylmethoxy)-benzofuran-5-yl]-ethanone The title compound was prepared from Example 59a) as described in Example 43 step iii in 46% yield. $^1$H-NMR (300 MHz, CDCl$_3$) δ 0.94-1.00 (m, 1H), 1.08-1.16 (m, 1H), 1.66-1.77 (m, 1H), 2.27-2.38 (m, 1H), 2.43 (s, 3H), 2.56 (s, 3H), 3.87-3.93 (m, 1H), 4.17-4.23 (m, 1H), 6.67 (d, J=2.1 Hz, 1H), 7.16-7.29 (m, 5H), 7.43 (d, J=2.1 Hz, 1H), 7.75 (s, 1H, OH).

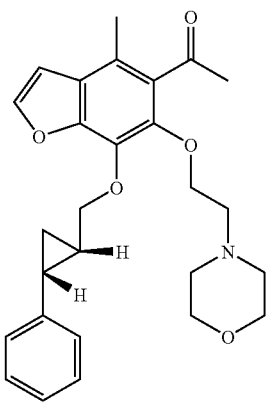

59c) 1-[4-Methyl-6-(2-morpholin-4-yl-ethoxy)-7-(1S,2R-2-phenyl-cyclopropylmethoxy)-benzofuran-5-yl]-ethanone The title compound was prepared from Example 59b) as described in Example 43 step iv, v in 62% yield (over 2 steps). ¹H-NMR (300 MHz, CDCl₃) δ 0.92-0.98 (m, 1H), 1.09-1.16 (m, 1H), 1.66-1.73 (m, 1H), 2.27-2.37 (m, 4H), 2.42-2.52 (m, 7H), 2.60 (t, J=5.6 Hz, 2H), 3.69 (t, J=4.6 Hz, 4H), 3.92-4.15 (m, 4H), 6.67 (d, J=2.1 Hz, 1H), 7.10-7.23 (m, 5H), 7.48 (d, J=2.1 Hz, 1H).

Example 60

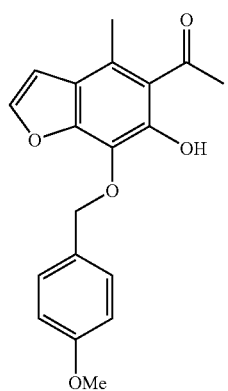

60a) 5-Acetyl-6-hydroxy-4-methyl-7-(4-methoxybenzyloxy)benzofuran

Example 43a) was treated with 4-methoxybenzyl chloride according to General Procedure A, followed by hydrolysis according to General Procedure B to offer the title compound in 46% yield (over 2 steps). ¹H NMR (300 MHz, CDCl₃): δ 2.50 (s, 3H), 2.60 (s, 3H), 3.79 (s, 3H), 5.28 (s, 2H), 6.73 (d, J=2.1 Hz, 1H), 6.86 (d, J=8.5 Hz, 2H), 7.36 (d, J=8.5 Hz, 2H), 7.53 (d, J=2.1 Hz, 1H), 8.69 (s, 1H). MS (ES⁺) m/z 348.8 (M+Na⁺).

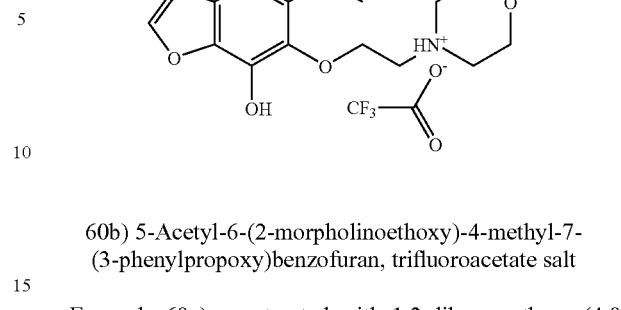

60b) 5-Acetyl-6-(2-morpholinoethoxy)-4-methyl-7-(3-phenylpropoxy)benzofuran, trifluoroacetate salt Example 60a) was treated with 1,2-dibromoethane (4.0 eqs) according to General Procedure A, followed by reaction with morpholine according to General Procedure E. The corresponding morpholino derivative (439 mg, 1.0 mmol) was dissolved in dichloromethane (20 mL) and cooled to 0° C. Then, anisole (5 mL) and TFA (5 mL) were added successively to the reaction mixture, which was allowed to stir at room temperature overnight. The solvents were removed under vacuum and the crude was sonicated in 5 ml of diethyl ether:hexane (1:1) to offer the trifluoroacetate salt as an off-white solid in 45% yield. ¹H NMR (300 MHz, CDCl₃): δ 2.30 (s, 3H), 2.50 (s, 3H), 3.00-3.60 (m, 6H), J=4.7 Hz, 4H), 4.18 (t, J=4.7 Hz, 2H), 6.72 (d, J=2.1 Hz, 1H), 7.62 (d, J=2.1 Hz, 1H). MS (ES⁺) m/z 348.8 (M+Na⁺).

Step iv

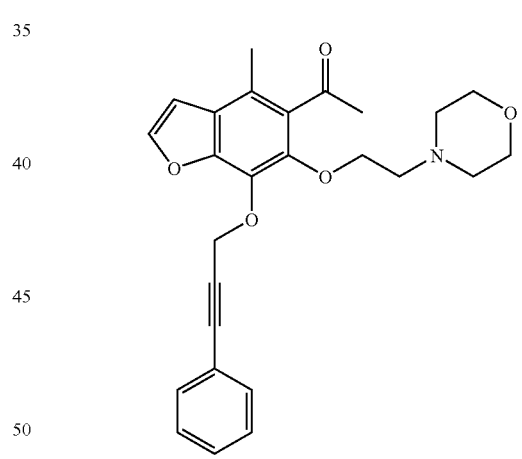

60c) 1-[4-Methyl-6-(2-morpholin-4-yl-ethoxy)-7-(3-phenyl-prop-2-ynyloxy)-benzofuran-5-yl]-ethanone To a solution of Example 60b) (40 mg, 0.092 mmol) in dry DMF (1 mL) was added a solution of (3-bromopropyn-1-yl)benzene (22 mg, 0.11 mmol) in minimum DMF) and Cs₂CO₃ (60 mg, 0.18 mmol) and the resulting suspension was stirred at room temperature for 2 h. The reaction was quenched with water and extracted with EtOAc. The organic layer was washed with water (×2) and brine, dried over MgSO₄ and concentrated under vacuum. The crude residue was purified by silica-gel flash chromatography. Yield=45%. ¹H NMR (300 MHz, CDCl₃): δ 2.33 (s, 3H), 2.55 (s, 3H), 2.53-2.56 (m, 4H), 2.70-2.74 (m, 2H), 3.67-3.70 (m, 4H), 4.21 (t, J=5.6 Hz, 2H), 6.75 (d, J=2.2 Hz, 1H), 7.20-7.35 (m, 5H), 7.61 (d, J=2.2 Hz, 1H). MS (ES⁺) m/z 433.9 (M+H⁺).

Example 61

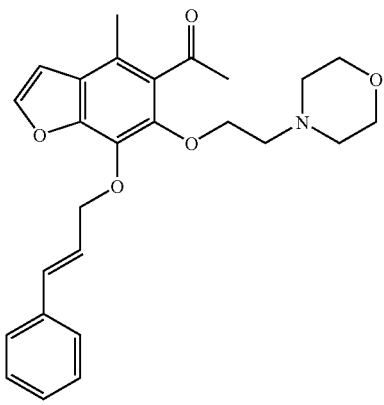

1-[4-Methyl-6-(2-morpholin-4-yl-ethoxy)-7-(E-3-phenyl-allyloxy)-benzofuran-5-yl]-ethanone Example 61 was prepared from Example 60b) and ((E)-3-Bromo-propenyl)benzene as described for Example 60 Step iv) in 65% yield. ¹H NMR (300 MHz, CDCl₃): δ 2.31 (s, 3H), 2.47-2.50 (m, 4H), 2.55 (s, 3H), 2.68 (t, J=5.6 Hz, 2H), 3.65-3.68 (m, 4H), 4.15 (t, J=5.6 Hz, 2H), 5.00 (d, J=6.2 Hz, 2H), 6.47 (dt, J=15.9, 6.2 Hz, 1H), 6.72 (d, J=15.9 Hz, 1H), 6.74 (d, J=2.2 Hz, 1H), 7.21-7.39 (m, 5H), 7.60 (d, J=2.2 Hz, 1H). MS (ES⁺) m/z 435.9 (M+H⁺).

Example 62

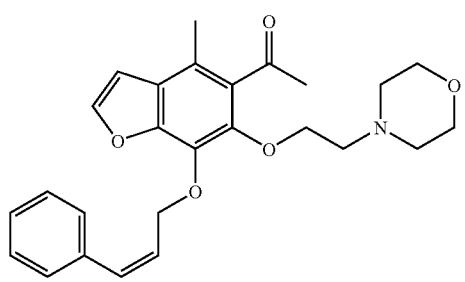

1-[4-Methyl-6-(2-morpholin-4-yl-ethoxy)-7-(Z-3-phenyl-allyloxy)-benzofuran-5-yl]-ethanone Example 62 was prepared from Example 60b) and ((Z)-3-Bromo-propenyl)benzene as described for Example 60 Step iv) in 11% yield. ¹H NMR (300 MHz, CDCl₃): δ 2.31 (s, 3H), 2.46-2.49 (m, 4H), 2.54 (s, 3H), 2.64 (t, J=5.6 Hz, 2H), 3.66-3.70 (m, 4H), 4.11 (t, J=5.6 Hz, 2H), 5.13 (d, J=6.4 Hz, 2H), 6.05 (dt, J=11.7, 6.4 Hz, 1H), 6.65 (d, J=11.7 Hz, 1H), 6.72 (d, J=2.2 Hz, 1H), 7.14-7.35 (m, 5H), 7.53 (d, J=2.2 Hz, 1H). MS (ES⁺) m/z 435.9 (M+H⁺).

Example 63

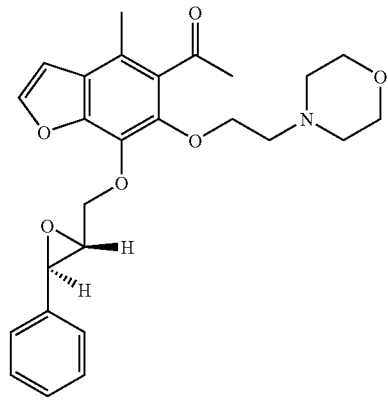

1-[4-Methyl-6-(2-morpholin-4-yl-ethoxy)-7-(2R,3R-3-phenyl-oxiranylmethoxy)-benzofuran-5-yl]-ethanone The title compound was prepared from Example 60b) and trans-2-bromomethyl-3-phenyl-oxirane (Tet Lett, 45 (46), p 8579, 2004) as described for Example 58 Step iv) except the reaction was heated to 60° C. Example 63 was furnished in 53% yield. ¹H NMR (300 MHz, CDCl₃): δ 2.32 (s, 3H), 2.48-2.51 (m, 4H), 2.55 (s, 3H), 2.68 (t, J=5.6 Hz, 2H), 3.41-3.45 (m, 1H), 3.68-3.71 (m, 4H), 3.88 (d, J=1.9 Hz, 1H), 4.15 (t, J=5.6 Hz, 2H), 4.45 (dd, J=11.4, 5.6 Hz, 1H), 4.66 (dd, J=11.4, 3.3 Hz, 1H), 6.74 (d, J=2.2 Hz, 1H), 7.22-7.37 (m, 5H), 7.57 (d, J=2.2 Hz, 1H). MS (ES⁺) m/z 451.9 (M+H⁺).

Example 64

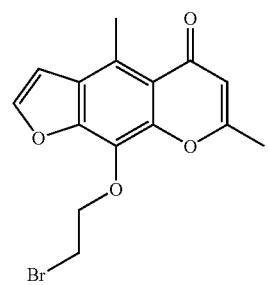

64a) 9-(2-Bromo-ethoxy)-4,7-dimethyl-furo[3,2-g]chromen-5-one 9-(2-Bromo-ethoxy)-4,7-dimethyl-furo[3,2-g]chromen-5-one was prepared as described in PCT/AU2006/000333.

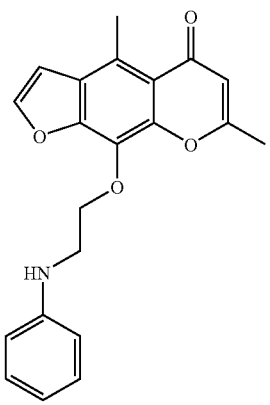

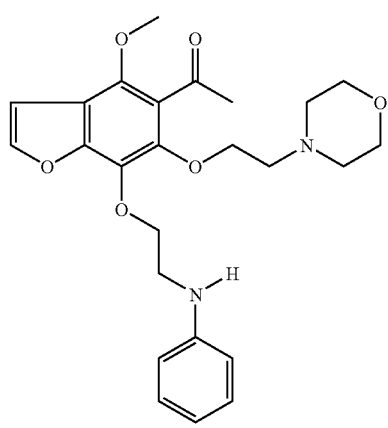

64b) 4,7-Dimethyl-9-(2-phenylamino-ethoxy)-furo[3,2-g]chromen-5-one

Aniline (0.60 mmol) was added to a solution of the bromide (70 mg, 0.199 mmol) in N-methylpyrrolidinone (0.5 mL) and the reaction was stirred at 90° C. overnight. After cooling, water (20 mL) and $CH_2Cl_2$ (30 mL) were added and the organic layer was washed with water (20 mL) and brine (20 mL), dried over $MgSO_4$ and concentrated under vacuum. The crude residue was purified by flash chromatography (silica-gel, $CH_2Cl_2$/EtOAc, 9:1) to afford the product as a white solid (53 mg, 73%). $^1$H-NMR (300 MHz, $CDCl_3$) δ 2.31 (s, 3H), 3.53 (t, J=4.9 Hz, 2H), 4.05 (s, 3H), 4.52 (t, J=4.8 Hz, 2H), 6.03 (s, 1H), 6.66-6.75 (m, 3H), 7.00 (dd, J=0.8, 2.2 Hz, 1H), 7.19 (t, J=7.6 Hz, 2H), 7.60 (dd, J=0.8, 2.2 Hz, 1H). MS ($ES^+$) m/z 365.9 ($M+H^+$).

64d) 1-[4-Methoxy-6-(2-morpholin-4-yl-ethoxy)-7-(2-phenylamino-ethoxy)-benzofuran-5-yl]ethanone Example 64c) was treated with 4-(2-chloroethyl)morpholine hydrochloride as described under General Procedure I and the crude product was purified by flash chromatography with methanol:ethylacetate:dichloromethane (1:29:70) to give the title compound in 99% yield. $^1$H-NMR (300 MHz, $CDCl_3$) δ 2.48-2.54 (m, 7H), 2.66-2.70 (m, 2H), 3.47 (t, J=5.1 Hz, 2H), 3.68-3.73 (m, 4H), 3.98 (s, 3H), 4.16 (t, J=5.5 Hz, 2H), 4.47 (t, J=5.1 Hz, 2H), 4.64 (br s, 1H), 6.64-6.72 (m, 3H), 6.87 (d, J=2.3 Hz, 1H), 7.17 (t, J=7.4 Hz, 2H), 7.56 (d, J=2.3 Hz, 1H).

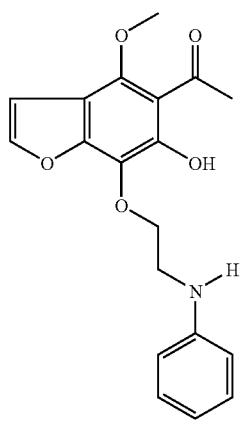

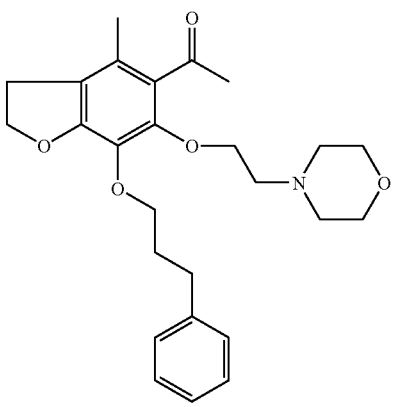

Example 65

64c) 1-[6-Hydroxy-4-methoxy-7-(2-phenylamino-ethoxy)-benzofuran-5-yl]-ethanone The title compound was prepared from Example 64b) as described under General Procedure B in 43% yield. $^1$H-NMR (300 MHz, $CDCl_3$) δ 2.71 (s, 3H), 3.42 (t, J=5.0 Hz, 2H), 4.13 (s, 3H), 4.40 (t, J=5.1 Hz, 2H), 4.72 (br s, 1H), 6.65-6.71 (m, 3H), 6.88 (d, J=2.3 Hz, 1H), 7.16 (t, J=8.4 Hz, 2H), 7.47 (d, J=2.3 Hz, 1H). $^{13}$C NMR (75 MHz, $CDCl_3$) δ 205.2, 153.8, 152.8, 152.0, 148.3, 143.8, 129.1, 127.1, 117.4, 113.2, 110.6, 110.4, 105.9, 72.1, 60.4, 43.7, 33.2. MS ($ES^+$) m/z 341.9 ($M+H^+$).

5-Acetyl-6-(2-morpholinoethoxy)-4-methyl-7-(3-phenylpropoxy)-2,3-dihydrobenzofuran The title compound was prepared from Example 19 as described under General Procedure F in 60% yield. $^1$H-NMR (300 MHz, $CDCl_3$) δ 1.98-2.07 (m, 5H), 2.46 (t J=4.2 Hz, 4H), 2.52 (s, 3H), 2.62 (t, J=5.6 Hz, 2H), 2.79 (t, J=8.1 Hz, 2H), 3.07 (t, J=8.7 Hz, 2H), 3.67 (t, J=4.7 Hz, 4H), 4.08 (q, J=6.5 Hz, 4H), 4.60 (t, J=8.7 Hz, 2H), 7.14-7.29 (m, 5H). MS (ES+) m/z 440.0 (M+H+).

Example 66

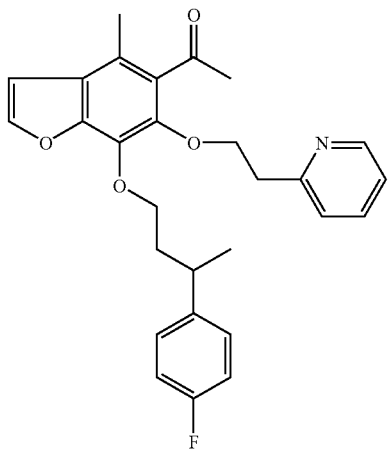

1-[7-[3-(4-Fluoro-phenyl)-butoxy]-4-methyl-6-(2-pyridin-2-yl-ethoxy)-2,3-dihydro-benzofuran-5-yl]-ethanone The title compound was prepared from Example 44d) as described under General Procedure F in 40% yield. $^1$H-NMR (300 MHz, CDCl$_3$) δ 1.24 (d, J=7.0 Hz, 3H), 1.75-1.93 (m, 2H), 2.02 (s, 3H), 2.24 (s, 3H), 2.94-3.14 (m, 5H), 3.84-3.93 (m, 2H), 4.35 (t, J=6.6 Hz, 2H), 4.56 (t, J=8.7 Hz, 2H), 6.92 (t, J=8.7 Hz, 1H), 7.13-7.24 (m, 4H), 7.57 (dt, J=1.7 Hz, 7.6 Hz, 1H), 8.51 (d, J=4.4 Hz, 1H).

Example 67

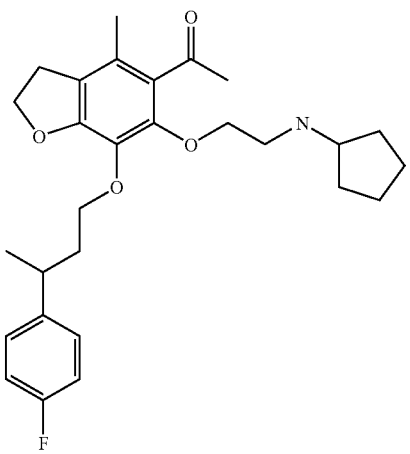

1-{6-(2-Cyclopentylamino-ethoxy)-7-[3-RS-(4-fluorophenyl)-butoxy]-4-methyl-2,3-dihydro-benzofuran-5-yl}-ethanone The title compound was prepared from Example 45b) as described under General Procedure F in 57% yield. $^1$H-NMR (300 MHz, CDCl$_3$) δ 1.27-1.38 (m, 5H), 1.50-1.49-1.72 (m, 5H), 1.78-1.86 (m, 2H), 1.92-2.04 (m, 2H), 2.07 (s, 3H), 2.48 (s, 3H), 2.84 (t, J=5.3 Hz, 2H), 2.96-3.10 (m, 4H), 3.92-4.01 (m, 2H), 4.08 (t, J=5.3 Hz, 2H), 4.58 (t, J=8.7 Hz, 2H), 6.93-6.98 (m, 2H), 7.15-7.20 (m, 2H).

Example 68

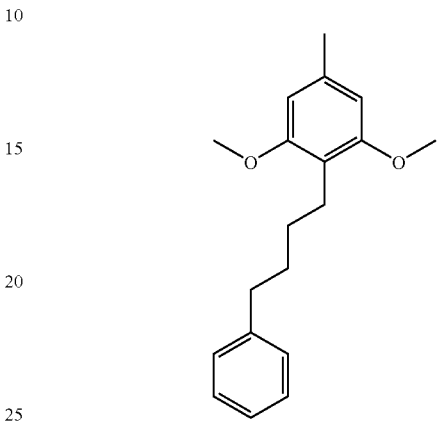

68a)
1,3-Dimethoxy-5-methyl-2-(4-phenylbutyl)benzene

A solution of nBuLi in hexanes (1.7 M, 14 mL, 24 mmol) was added over 15 min to a solution of 3,5-dimethoxytoluene (2.93 mL, 20 mmol) in THF (20 mL) at 0° C. The reaction mixture was stirred at 0° C. for 1 h then at room temperature for 3 h. The reaction was cooled to 0° C. and a solution of the 4-phenylbutylbromide (4.13 mL, 1.2 mmol) in toluene (15 mL) was added over 5 min. The reaction mixture was allowed to warm to room temperature and heated to 80° C. for 3-4 h. The reaction was quenched slowly with water and partitioned over Et$_2$O (100 mL) and water (100 mL). The phases were separated and the aqueous phase was extracted with Et$_2$O (3×100 mL). The pooled organics were washed with brine (120 mL), dried over Na$_2$SO$_4$, and concentrated under vacuum and the crude product was purified by flash chromatography (silica-gel, petroleum ether/EtOAc 200:1) to afford the product as a clear oil (4.6 g, 81%). $^1$H NMR (CDCl$_3$): δ 1.53-1.67 (m, 4H), 2.31 (s, 3H), 2.60-2.64 (m, 4H), 3.76 (s, 6H), 6.34 (s, 2H), 7.13-7.22 (m, 5H).

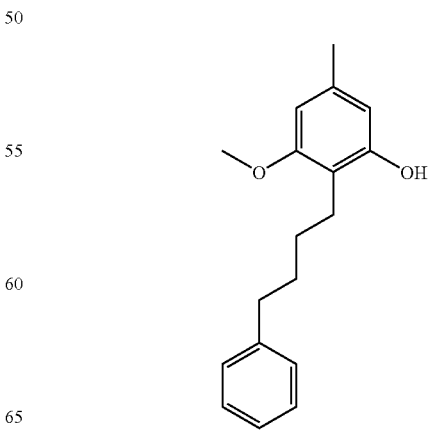

68b) 3-Methoxy-5-methyl-2-(4-phenyl-butyl)-phenol

To a solution of NaH (60% in oil, 1.20 g, 30 mmol) in DMF (60 mL) at 0° C. was added ethanethiol (2.22 mL, 30 mmol) over 5 min. The reaction mixture was stirred at room temperature for 30 min and then a solution of the Example 68a) (2.13 g, 7.5 mmol) in DMF (45 mL) was added. The reaction mixture was stirred at 160° C. for 3.5 h. Upon cooling the solution was partitioned over ethyl acetate (100 mL) and HCl$_{(aq)}$ (2M, 100 mL) and the aqueous phase was extracted with ethyl acetate (2×150 mL). The pooled organics were washed with brine (200 mL), dried over MgSO$_4$ and concentrated under vacuum. The crude product was purified by flash chromatography (silica-gel, petroleum ether/ethyl acetate, 9:1) to afford the product as a clear oil (2.2 g, 99%). $^1$H NMR (CDCl$_3$): δ 1.53-1.71 (m, 4H), 2.27 (s, 3H), 2.60-2.67 (m, 4H), 3.78 (s, 3H), 5.84 (br s, 1H), 6.26 (s, 1H), 6.29 (s, 1H) 7.16-7.29 (m, 5H).

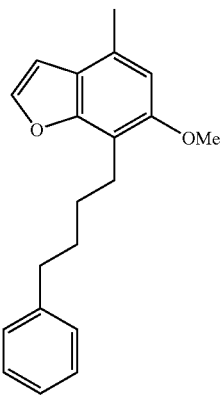

68c) 6-Methoxy-4-methyl-7-(4-phenyl-butyl)-benzofuran

To a mixture of Example 68c) (946 mg, 3.5 mmol) and K$_2$CO$_3$ (967 mg, 7.0 mmol) in DMF (7 mL) was added bromoacetaldehyde diethyl acetal (1.08 mL, 7.0 mmol) and the reaction mixture was stirred at 150° C. for 3.5 h. Upon cooling, further bromoacetaldehyde diethyl acetal (0.54 mL, 3.5 mmol) was added and reaction mixture was stirred at 150° C. for 2.5 h, Upon cooling the reaction mixture was partitioned over ethyl acetate and water (1:1, 200 mL) and the aqueous phase was extracted with ethyl acetate (2×150 mL). The pooled organics were washed with brine (200 mL), dried over MgSO$_4$ and concentrated under vacuum. The crude product was heated at 50° C. under high vacuum for 3 h then purified by flash chromatography (silica-gel, petroleum ether/ethyl acetate, 100:1, 50:1) to afford the intermediate acetal (0.99 g, 73%). The acetal (0.50 g, 1.3 mmol) was added to a stirred mixture of polyphosphoric acid (3.5 g) in toluene (10 mL) at 100° C. The reaction mixture was stirred at 100° C. for 3 h then cooled on an ice-bath and water (50 mL) was added. The organics were extracted with ethyl acetate (3×50 mL) and the pooled ethyl acetate phases were washed with brine (100 mL), dried over MgSO$_4$ and concentrated under vacuum. The crude product was purified by flash chromatography (silica-gel, petroleum ether/ethyl acetate, 200:1) to afford the title compound (0.22 g, 57%). $^1$H NMR (300 MHz, CDCl$_3$) δ 1.67-1.72 (m, 4H), 2.48 (s, 3H), 2.66 (t, J=7.2 Hz, 2H), 2.90 (t, J=7.2 Hz, 2H), 3.85 (s, 3H), 6.69 (d, J=2.3 Hz, 1H), 7.16-7.28 (m, 5H), 7.53 (d, J=2.3 Hz, 1H).

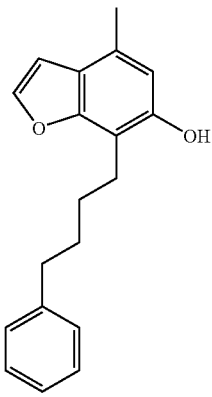

68d) 4,6-Dimethyl-7-(4-phenylbutyl)-benzofuran

Example 68c) (205 mg, 0.72 mmol) was treated in a similar manner as described for the preparation of Example 68b) to give the title compound (199 mg, 99%) as a straw-coloured solid. $^1$H NMR (300 MHz, CDCl$_3$) δ 1.69-1.74 (m, 4H), 2.42 (s, 3H), 2.67 (m, 2H), 2.88 (m, 2H), 4.85 (br s, 1H), 6.55 (s, 1H), 6.68 (d, J=2.3 Hz, 1H), 7.15-7.28 (m, 5H), 7.50 (d, J=2.3 Hz, 1H).

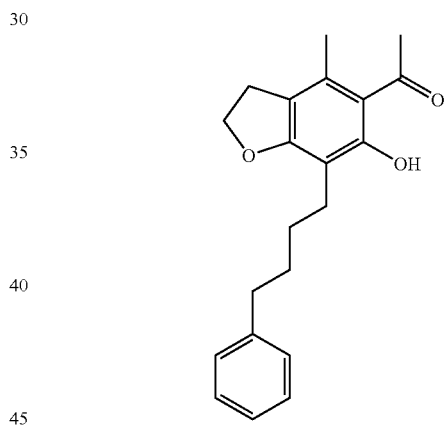

68e) 1-[6-Hydroxy-4-methyl-7-(4-phenyl-butyl)-2,3-dihydro-benzofuran-5-yl]-ethanone Example 68d) (150 mg, 0.53 mmol) was treated as described under General Procedure F to give the intermediate dihydrofuran (136 mg, 90%). A mixture of the intermediate (64 mg, 0.20 mmol) and zinc chloride (60 mg, 0.44 mmol) in ether (2.25 mL) and acetonitrile (1.75 mL) at 0° C. was treated with HCl for 15 min. The mixture was stirred at room temperature for 16 h and then diluted with ether and petroleum ether, which caused an oil to separate. The reaction mixture decanted and the remaining oil was dissolved in water (10 mL) and heated at 80° C. for 2 h. On cooling the water was extracted with ethyl acetate (2×20 mL). The organics were dried over Na$_2$SO$_4$ and concentrated under vacuum to give the title compound (28 mg, 44%). $^1$H NMR (300 MHz, CDCl$_3$) δ 1.60-1.69 (m, 4H), 2.43 (s, 3H), 2.59-2.67 (m, 6H), 3.10 (t, J=8.2 Hz, 2H), 4.59 (t, J=8.2 Hz, 2H), 7.12-7.28 (m, 5H), 13.80 (s, 1H).

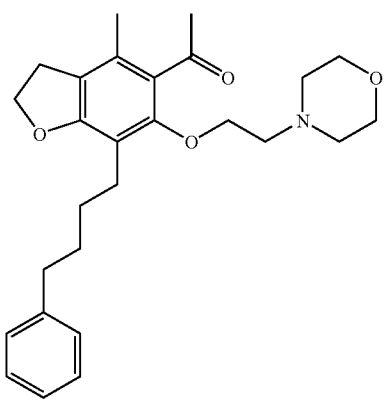

68f) 1-[4-Methyl-6-(2-morpholin-4-yl-ethoxy)-7-(4-phenyl-butyl)-2,3-dihydro-benzofuran-5-yl]-ethanone The title compound was prepared from Example 68e) and 4-(2-chloroethyl)morpholine hydrochloride as described under General Procedure I in 39% yield. $^1$H-NMR (300 MHz, CDCl$_3$) δ 1.61-1.70 (m, 4H), 2.10 (s, 3H), 2.49-2.67 (m, 11H), 3.09 (t, J=8.7 Hz, 2H), 3.72-3.80 (m, 6H), 4.59 (t, J=8.2 Hz, 2H), 7.16-7.29 (m, 5H).

BIOLOGICAL DATA

Potency of compounds to inhibit the human Kv1.3 ion channel were determined as follows:

EC50 values for inhibition of Kv1.3 currents were determined by the method according to Schmitz et al (2005) Molecular Pharmacology 68, 1254-1270 with the following differences:
1. Human Jurkat cells (which endogenously express hKv1.3) were used in place of rat L929 cells.
2. All electrophysiology was performed using planar patch clamp (Port-A-Patch, Nanion Technologies Gmbh, Munich) in contrast to conventional patch clamp.
3. EC50 values shown were determined from averaged dose response data obtained from 3 or more cells.

TABLE 1

| Example No. | EC$_{50}$ Kv1.3 microM |
|---|---|
| 1 | 0.29 |
| 2 | 0.42 |
| 3 | 0.184 |
| 4 a) | 0.79 |
| 4 b) | — |
| 4 c) | 0.225 |
| 5 a) | — |
| 5 b) | 0.88 |
| 6 a) | — |
| 6 b) | 0.72 |
| 7 | 0.68 |
| 8 | 0.75 |
| 9 | 2.42 |
| 10 | 1.51 |
| 11 | 0.98 |
| 12 | 0.69 |
| 13 b) | 0.48 |
| 14 b) | — |
| 14 c) | 0.91 |
| 15 a) | 0.27 |
| 15 b) | 0.16 |
| 16 | 0.11 |
| 17 | 0.081 |
| 18 a) | 0.114 |
| 18 b) | 0.300 |
| 18 c) | 0.42 |
| 19 | 0.051 |
| 20 a) | — |
| 20 b) | 0.068 |
| 21 a) | 0.023 |
| 21 b) | 0.16 |
| 22 c) | 0.61 |
| 23 d) | 0.174 |
| 29 | 0.136 |
| 26 | 0.140 |
| 25 | 0.60 |
| 30 | 0.12 |
| 24 | 0.59 |
| 27 b) | 0.43 |
| 28 b) | 0.64 |
| 31b | 0.081 |
| 32 | 0.049 |
| 33 | 0.343 |
| 34 | 0.223 |
| 35 | 0.100 |
| 36 | 0.122 |
| 37 | 0.074 |
| 38 | — |
| 39 | 0.576 |
| 40 | 0.066 |
| 41 | 0.215 |
| 42 | 0.480 |
| 43b | 0.229 |
| 43c | 0.954 |
| 43e | 0.286 |
| 44d | 0.022 |
| 45b | 0.043 |
| 46b | 0.198 |
| 47a | 0.531 |
| 47b | 0.074 |
| 48 | 0.047 |
| 49 | — |
| 50a | 0.423 |
| 50b | 0.016 |
| 51 | 0.018 |
| 52 | — |
| 53 | 0.023 |
| 54a | 0.16 |
| 54b | 1.6 |
| 55 | 6.6 |
| 56b | 0.362 |
| 57b | 0.159 |
| 58a | 0.165 |
| 58b | 0.512 |
| 58c | 0.100 |
| 59a | 0.215 |
| 59c | — |
| 60c | 0.331 |
| 61 | 0.221 |
| 62 | — |
| 63 | 0.600 |
| 64c | 0.340 |
| 64d | — |
| 65 | 0.200 |
| 66 | 0.014 |
| 67 | 0.008 |
| 68 | 0.020 |

Effect of appending L-R$_6$ on Potency of Kv1.3 Inhibition

| Example number | Structure | EC$_{50}$ Kv1.3 micromol |
|---|---|---|
| 47a | 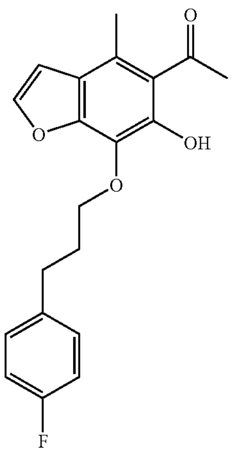 | 0.531 |
| 47b | 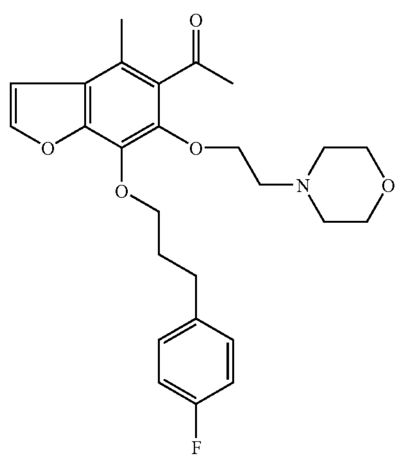 | 0.074 |
| 43c | 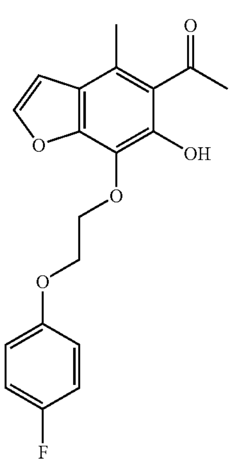 | 0.954 |
| 43e | | 0.286 |
| 50a | | 0.423 |
| 50b | | 0.016 |

| Example number | Structure | EC$_{50}$ Kv1.3 micromol |
|---|---|---|
| 53 | 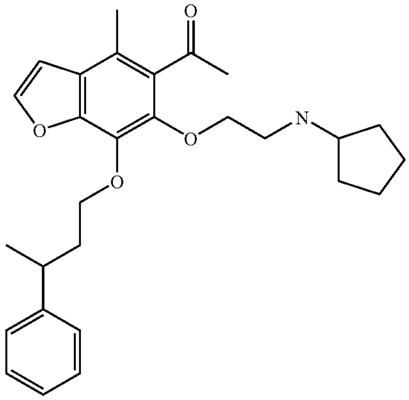 | 0.023 |
| 58b | 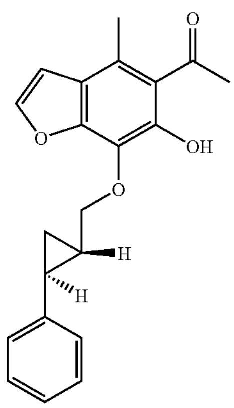 | 0.512 |
| 58c | 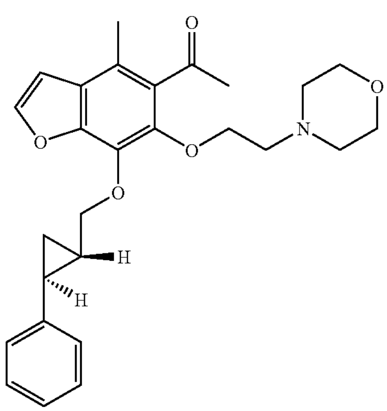 | 0.100 |

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The claims defining the invention are as follows:

1. A compound represented by formula (Ia) or a salt thereof,

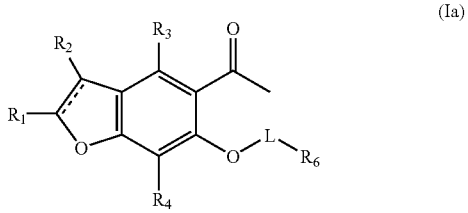

(Ia)

wherein

- - - is an optional double bond;

$R_1$ is chloro or hydrogen;

$R_2$ is hydrogen;

$R_3$ is methyl or methoxy;

$R_4$ is selected from lower alkyl, lower alkoxy, $C_{2-6}$ alkenyl, $C_{2-6}$ alkenyloxy, $C_{2-6}$ alkynyl, or $C_{2-6}$ alkynyloxy, each substituted by optionally substituted aryl, optionally substituted aryloxy, optionally substituted heteroaryl, optionally substituted heteroaryloxy, optionally substituted heterocyclyl, optionally substituted heterocyclyloxy, or NR'R" (where R' and R" are independently selected from hydrogen and lower alkyl);

L is a divalent linker group of 1-6 atoms in length selected from optionally substituted alkylene, optionally substituted alkenylene, optionally substituted alkynylene; and $R_6$ is selected from halo, CN, optionally substituted $C_{3-7}$ cycloalkyl, optionally substituted aryl, optionally substituted heteroaryl, optionally substituted heterocyclyl, —C(O)-heterocyclyl, —C(O)NR'''R''', —NR'''R''', —OR''', —S(O)R''', —S(O)$_2$R''', —Se(O)R''', and —Se(O)$_2$R''' (where each R''' is independently selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl).

2. A compound of formula (Ia) or salt thereof, according to claim 1 wherein L is an optionally substituted alkylene group.

3. A compound of formula (Ia) or salt thereof, according to claim 2 wherein L is an unsubstituted alkylene group.

4. A compound of formula (Ia) or salt thereof, according to claim 3 wherein L is an unsubstituted ethylene, propylene, or butylene group.

5. A compound of formula (Ia) or salt thereof, according to claim 1 wherein $R_6$ is CN, optionally substituted aryl, optionally substituted heteroaryl, optionally substituted heterocyclyl, —C(O)-heterocyclyl, —C(O)NR'''R''', —NR'''R''', —OR''', —S(O)R''', or —S(O)$_2$R''' (where each R''' is independently selected from optionally substituted alkyl, optionally substituted $C_{3-7}$ cycloalkyl, optionally substituted heterocyclyl, optionally substituted heteroaryl and optionally substituted aryl).

6. A compound of formula (Ia) according to claim 1 or a salt thereof wherein

- - - is a double bond;

$R_3$ is methyl or methoxy;

$R_4$ is a lower alkyl or lower alkoxy terminally substituted by aryl, aryloxy, heteroaryl, heteroaryloxy, heterocyclyl, heterocyclyloxy, or NR'R" (where R' and R" are independently selected from hydrogen and lower alkyl);

L is a divalent linker group of 2-4 atoms in length selected from a ethylene, propylene or butylene; and $R_6$ is CN, optionally substituted aryl, optionally substituted heteroaryl, optionally substituted heterocyclyl, —C(O)-heterocyclyl, —C(O)NR'''R''', —NR'''R''', —OR''', —SR''', —S(O)R''', or —S(O)$_2$R''' (where R' is selected from optionally substituted alkyl, optionally substituted $C_{3-7}$ cycloalkyl, optionally substituted heterocyclyl, optionally substituted heteroaryl and optionally substituted aryl).

7. A compound selected from:
5-Acetyl-4,7-dimethoxy-6-(3-(phenyl)propoxy)benzofuran;
5-Acetyl-4,7-dimethoxy-6-(4-(phenoxy)butoxy))benzofuran;
5-Acetyl-6-(3-phenylpropoxy)benzofuran;
5-Acetyl-4-methyl-7-methoxy-6-(3-(phenyl)propoxy)benzofuran;
5-Acetyl-4,7-dimethoxy-6-(2-(phenoxy)ethoxy)benzofuran;
5-Acetyl-4,7-dimethoxy-6-(3-(phenoxy)propoxy)benzofuran;
5-Acetyl-4,7-dimethoxy-6-(2-(thiophenoxy)ethoxy)benzofuran;
5-Acetyl-4,7-dimethoxy-6-(3-(phenylthio)propoxy)benzofuran;
5-Acetyl-4,7-dimethoxy-6-(2-(benzenesulfonyl)ethoxy)benzofuran;
5-Acetyl-4,7-dimethoxy-6-(3-(benzenesulfonyl)propoxy)benzofuran;
5-Acetyl-4,7-dimethoxy-6-(2-(phenylamino)ethoxy)benzofuran;
5-Acetyl-4,7-dimethoxy-6-(3-(phenylamino)propoxy)benzofuran;
5-Acetyl-7-N,N-dimethylaminomethyl-4-methoxy-6-(3-(phenyl)propoxy)benzofuran;
5-Acetyl-4-methoxy-7-(2-(N-morpholino)ethoxy-6-(4-(phenoxy)butoxy))benzofuran
5-Acetyl-6-(2-dimethylaminoethoxy)-4-methoxy-7-(3-phenylpropoxy)benzofuran;
5-Acetyl-6-(2-morpholinoethoxy)-4-methoxy-7-(3-phenylpropoxy)benzofuran;
5-Acetyl-6-(2-imidazol-1-ylethoxy)-4-methoxy-7-(3-phenylpropoxy)benzofuran;
5-Acetyl-6-(2-dimethylaminoethoxy)-4-methyl-7-(3-phenylpropoxy)benzofuran;
5-Acetyl-6-(2-morpholinoethoxy)-4-methyl-7-(3-phenyl-propoxy)benzofuran;
5-Acetyl-6-(2-imidazol-1-ylethoxy)-4-methyl-7-(3-phenylpropoxy)benzofuran;
5-Acetyl-6-[2-(5-aminotetrazol-2-yl)ethoxy]-4-methyl-7-(3-phenylpropoxy)benzofuran;
5-Acetyl-6-[2-(5-aminotetrazol-1-yl)ethoxy]-4-methyl-7-(3-phenylpropoxy)benzofuran;
5-Acetyl-6-(2-morpholin-4-yl-ethoxy)-7-(3-phenylpropoxy)benzofuran;
5-Acetyl-6-(2-morpholin-4-yl-ethoxy)-4-(4-phenoxybutoxy)benzofuran;
3-[6-(2-Morpholin-4-ylethoxy)-4-(4-phenoxybutoxy)benzofuran-5-yl]-3-oxo-propionic acid ethyl ester;
5-Acetyl-6-(2-dimethylamino-ethoxy)-4-(4-phenoxybutoxy)benzofuran;
5-Acetyl-6-(2-methyl-piperazin-1-yl)-4-methyl-7-(3-phenylpropoxy)-benzofuran;
5-Acetyl-6-(3-morpholin-4-yl-propoxy)-4-methyl-7-(3-phenylpropoxy)-benzofuran;
5-Acetyl-6-(4-morpholin-4-yl-butoxy)-4-methyl-7-(3-phenylpropoxy)-benzofuran;
5-Acetyl-6-(3-imidazol-1-yl-propoxy)-4-methyl-7-(3-phenylpropoxy)-benzofuran;
5-Acetyl-6-(4-imidazol-1-yl-butoxy)-4-methyl-7-(3-phenylpropoxy)-benzofuran;
1-{4-Methyl-7-(3-phenyl-propoxy)-6-[2-(pyrazin-2-yloxy)-ethoxy]-benzofuran-5-yl}-ethanone;
1-[6-(2-Cyclopentylamino-ethoxy)-4-methyl-7-(3-phenyl-propoxy)-benzofuran-5-yl]-ethanone;
1-[4-Methyl-7-(3-phenyl-propoxy)-6-(2-piperidin-1-yl-ethoxy)-benzofuran-5-yl]-ethanone;
1-[4-Methyl-7-(3-phenyl-propoxy)-6-(2-pyrrolidin-1-yl-ethoxy)-benzofuran-5-yl]-ethanone;
1-[4-Methyl-7-(3-phenyl-propoxy)-6-(2-[1,2,3]triazol-2-yl-ethoxy)-benzofuran-5-yl]-ethanone;
1-[4-Methyl-7-(3-phenyl-propoxy)-6-(2-[1,2,3]triazol-1-yl-ethoxy)-benzofuran-5-yl]-ethanone;
1-[4-Methyl-7-(3-phenyl-propoxy)-6-(2-[1,2,4]triazol-1-yl-ethoxy)-benzofuran-5-yl]-ethanone;
4-{2-[5-Acetyl-4-methyl-7-(3-phenyl-propoxy)-benzofuran-6-yloxy]-ethyl}-morpholin-3-one;
5-Acetyl-6-(2-(2-Hydroxy-ethylamino)-ethoxy)-4-methyl-7-(3-phenylpropoxy)-benzofuran;
5-Acetyl-4-methyl-7-(3-phenylpropoxy)-6-(2-pyridin-2-yl-ethoxy)benzofuran;
1-[2-Chloro-4-methyl-6-(2-morpholin-4-yl-ethoxy)-7-(3-phenyl-propoxy)-benzofuran-5-yl]-ethanone;
2-[5-Acetyl-4-methyl-7-(3-phenyl-propoxy)-benzofuran-6-yloxy]-1-morpholin-4-yl-ethanone;
1-[7-[2-(4-Fluoro-phenoxy)-ethoxy]-4-methyl-6-(2-morpholin-4-yl-ethoxy)-benzofuran-5-yl]-ethanone;
5-Acetyl-7-(3-[4-fluorophenyl]butoxy)-4-methyl-6-(2-pyridin-2-yl-ethoxy)benzofuran;
5-Acetyl-7-(3-[4-fluorophenyl]butoxy)-4-methyl-6-(2-Cyclopentylamino-ethoxy)benzofuran;
rac-1-[4-Methyl-7-(3-methyl-3-phenyl-butoxy)-6-(2-morpholin-4-yl-ethoxy)-benzofuran-5-yl]-ethanone,
5-Acetyl-7-(3-(4-fluorophenyl)propoxy)-6-hydroxy-4-methylbenzofuran;
5-Acetyl-7-(3-(4-fluorophenyl)propoxy)-4-methyl-6-(2-morpholinoethoxy)benzofuran;
1-[6-(2-Cyclopentylamino-ethoxy)-4-methyl-7-(3-(4-fluoro-phenyl)-propoxy)-benzofuran-5-yl]-ethanone;
1-[7-[3-(4-Fluoro-phenyl)-propoxy]-4-methyl-6-(2-pyridin-2-yl-ethoxy)-benzofuran-5-yl]-ethanone;
1-[4-Methyl-6-(2-morpholin-4-yl-ethoxy)-7-(3-phenyl-butoxy)-benzofuran-5-yl]-ethanone;
1-[4-Methyl-6-(2-morpholin-4-yl-ethoxy)-7-(3-phenyl-butoxy)-benzofuran-5-yl]-ethanone;
rac-1-[4-Methyl-7-(3-phenyl-butoxy)-6-(2-pyridin-2-yl-ethoxy)-benzofuran-5-yl]-ethanone;
1-[6-(2-Cyclopentylamino-ethoxy)-4-methyl-7-(3-phenyl-butoxy)-benzofuran-5-yl]-ethanone;
5-Acetyl-6-(3-cyanopropoxy)-4-methyl-7-(3-phenylpropoxy)benzofuran;
5-Acetyl-6-(3-(1H-tetrazol-5-yl)-propoxy)-4-methyl-7-(3-phenylpropoxy)benzofuran;
5-Acetyl-6-(3-(1H-tetrazol-5-yl)-ethoxy)-4-methyl-7-(3-phenylpropoxy)benzofuran;
5-Acetyl-7-(2,2-dimethyl-3-phenylpropoxy)-4-methyl-6-(2-morpholinoethoxy)benzofuran;
1-[4-Methyl-7-(1-RS-methyl-3-phenyl-propoxy)-6-(2-morpholin-4-yl-ethoxy)-benzofuran-5-yl]-ethanone;
1-[4-Methyl-6-(2-morpholin-4-yl-ethoxy)-7-(1S,2S-2-phenyl-cyclopropylmethoxy)-benzofuran-5-yl]-ethanone;

1-[4-Methyl-6-(2-morpholin-4-yl-ethoxy)-7-(1S,2R,2-phenyl-cyclopropylmethoxy)-benzofuran-5-yl]-ethanone;

1-[4-Methyl-6-(2-morpholin-4-yl-ethoxy)-7-(3-phenyl-prop-2-ynyloxy)-benzofuran-5-yl]-ethanone;

1-[4-Methyl-6-(2-morpholin-4-yl-ethoxy)-7-(E-3-phenyl-allyloxy)-benzofuran-5-yl]-ethanone;

1-[4-Methyl-6-(2-morpholin-4-yl-ethoxy)-7-(Z-3-phenyl-allyloxy)-benzofuran-5-yl]-ethanone;

1-[4-Methyl-6-(2-morpholin-4-yl-ethoxy)-7-(2R,3R-3-phenyl-oxiranylmethoxy)-benzofuran-5-yl]-ethanone;

1-[4-Methoxy-6-(2-morpholin-4-yl-ethoxy)-7-(2-phenylamino-ethoxy)-benzofuran-5-yl]-ethanone;

5-Acetyl-6-(2-morpholinoethoxy)-4-methyl-7-(3-phenyl-propoxy)-2,3-dihydrobenzofuran;

1-[7-[3-(4-Fluoro-phenyl)-butoxy]-4-methyl-6-(2-pyridin-2-yl-ethoxy)-2,3-dihydro-benzofuran-5-yl]-ethanone;

1-{6-(2-Cylcopentylamino-ethoxy)-7-[3-RS-(4-fluorophenyl)-butoxy]-4-methyl-2,3-dihydro-benzofuran-5-yl}-ethanone 1-[4-Methyl-6-(2-morpholin-4-yl-ethoxy)-7-(4-phenyl-butyl)-2,3-dihydro-benzofuran-5-yl]-ethanone, or a salt thereof.

8. A pharmaceutical composition comprising one or more compounds of formula (Ia) according to claim 1 or a salt thereof, and optionally a pharmaceutically acceptable carrier or diluent.

9. The compound of formula (Ia) according to claim 1 or a salt thereof wherein $R_1$ and $R_2$ are both hydrogen or $R_1$ is chloro and $R_2$ is hydrogen.

* * * * *